(12) United States Patent
Li et al.

(10) Patent No.: US 11,883,800 B2
(45) Date of Patent: *Jan. 30, 2024

(54) REDOX CATALYSTS FOR THE OXIDATIVE CRACKING OF HYDROCARBONS, METHODS OF MAKING, AND METHODS OF USE THEREOF

(71) Applicant: North Carolina State University, Raleigh, NC (US)

(72) Inventors: Fanxing Li, Raleigh, NC (US); Luke Michael Neal, Raleigh, NC (US); Junshe Zhang, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/332,509

(22) PCT Filed: Sep. 12, 2017

(86) PCT No.: PCT/US2017/051157
§ 371 (c)(1),
(2) Date: Mar. 12, 2019

(87) PCT Pub. No.: WO2018/049389
PCT Pub. Date: Mar. 15, 2018

(65) Prior Publication Data
US 2019/0262804 A1     Aug. 29, 2019

Related U.S. Application Data

(60) Provisional application No. 62/393,411, filed on Sep. 12, 2016.

(51) Int. Cl.
*B01J 23/83* (2006.01)
*B01J 23/94* (2006.01)
(Continued)

(52) U.S. Cl.
CPC ............ *B01J 23/83* (2013.01); *B01J 23/002* (2013.01); *B01J 23/8892* (2013.01); *B01J 23/94* (2013.01);
(Continued)

(58) Field of Classification Search
CPC ...... B01J 23/002; B01J 23/83; B01J 23/8892; B01J 2523/00; B01J 2523/24; B01J 2523/3706; B01J 2523/842
See application file for complete search history.

(56) References Cited

U.S. PATENT DOCUMENTS 6,770,256 B1 * 8/2004 Kaliaguine ........ C01G 45/1264
423/593.1
9,150,476 B1 * 10/2015 Shekhawat .......... C07C 29/153
(Continued)

FOREIGN PATENT DOCUMENTS

EP       0832056 B1     5/2001
JP   H08067645 A  *  3/1996  .............. Y02P 20/52
(Continued)

OTHER PUBLICATIONS

Cadigan Nanoscale(111) faceted rock-salt metal oxides in Catalysis, Catal. Sci. Technol. 2013, 3, p. 900-911).*

(Continued)

*Primary Examiner* — Jun Li
(74) *Attorney, Agent, or Firm* — THOMAS | HORSTEMEYER, LLP

(57) ABSTRACT

A variety of redox catalysts, methods of making, and methods of using thereof are provided. Surface modified redox catalysts are provided having an oxygen carrier core with an outer surface that has been modified to enhance the selectivity of the redox catalyst for oxidative dehydrogenation. The surface modification can include forming a redox catalyst outer layer on the outer surface and/or suppressing sites
(Continued)

that form nonselective electrophilic oxygen sites on the outer surface of the oxygen carrier. A variety of methods are provided for making the surface modified redox catalysts, e.g. modified Pechini methods. A variety of methods are provided for using the catalysts for oxidative cracking of light paraffins. Methods are provided for oxidative cracking of light paraffins by contacting the paraffin with a core-shell redox catalyst described herein to convert the paraffins to water and olefins, diolefins, or a combination thereof.

5 Claims, 49 Drawing Sheets

(51) Int. Cl.
C07C 5/48 (2006.01)
B01J 23/00 (2006.01)
B01J 37/03 (2006.01)
B01J 37/14 (2006.01)
B01J 35/00 (2006.01)
B01J 38/04 (2006.01)
B01J 23/889 (2006.01)
B01J 35/10 (2006.01)

(52) U.S. Cl.
CPC ........... B01J 35/008 (2013.01); B01J 37/036 (2013.01); B01J 37/14 (2013.01); B01J 38/04 (2013.01); C07C 5/48 (2013.01); B01J 35/1009 (2013.01); B01J 2523/00 (2013.01); B01J 2523/24 (2013.01); B01J 2523/3706 (2013.01); B01J 2523/842 (2013.01); C07C 2523/24 (2013.01); C07C 2523/83 (2013.01); Y02P 20/10 (2015.11); Y02P 20/52 (2015.11)

(56) References Cited

U.S. PATENT DOCUMENTS

| | | | |
|---|---|---|---|
| 10,138,182 B2 | 11/2018 | Sofranko et al. | |
| 10,486,143 B2* | 11/2019 | Li | B01J 38/12 |
| 2003/0198582 A1* | 10/2003 | Golden | F01N 3/281 |
| | | | 423/213.2 |
| 2007/0213208 A1* | 9/2007 | Tanaka | C01G 51/006 |
| | | | 502/302 |
| 2014/0128252 A1* | 5/2014 | Hosono | C01G 23/003 |
| | | | 502/350 |
| 2014/0256966 A1* | 9/2014 | Dumesic | B01J 35/002 |
| | | | 549/503 |
| 2017/0089571 A1* | 3/2017 | Orlovskaya | B01J 23/6522 |

FOREIGN PATENT DOCUMENTS

| | | | | |
|---|---|---|---|---|
| JP | 2003267705 A | * | 9/2003 | ............ G03B 17/02 |
| JP | 2010110671 A | * | 5/2010 | |
| WO | 2006063230 A1 | | 6/2006 | |
| WO | WO-2009071463 A2 | * | 6/2009 | ............ C07C 11/02 |
| WO | 2013113743 A1 | | 8/2013 | |

OTHER PUBLICATIONS

Tanaka (XPS and UPS studies on electronic structure of Li2O, Journal of Nuclear Materials 283-287 (2000) p. 1405-1408).*
Machine translation of JP2010110671, publication date May 20, 2010.*
Machine translation of JPH08067645A, publication date Mar. 1996.*
Gao et al., Li-Promoted LaxSr2-xFeO4-δ Core-Shell Redox Catalysts for Oxidative Dehydrogenation of Ethane under a Cyclic Redox Scheme, ACS Catal. 2016, 6, 11, 7293-7302, Publication Date:Sep. 14, 2016.*
International Search Report and Written Opinion for PCT/US2017/051157 dated Dec. 21, 2017.
Dai, H.X. et al., "Perovskite-Type Halo-oxide La1-xSrxFeO3-(delta)X(sigma) (X=F, Cl) Catalysts Selective for the Oxidation of Ethane to Ethene," 2000, Journal of Catalysis, 189:52-62.
Neal, L.M. et al., "Oxidative Dehydrogenation of Ethane: A Chemical Looping Approach," 2016, Energy Technol., 4:1200-1208.
Neal, Luke et al. "Effect of core and shell compositions on MeOx@LaySr 1 _yfe03 core-shell redox catalysts for chemical looping reforming of methane" Applied Energy 157 (2015) 391-398 http://dx.doi.org/10.1016/j.apenergy.2015.06.028.
Zhang, Leilei et al. "Selective Hydrogenation over Supported Metal Catalysts: From Nanoparticles to Single Atoms" Chem. Rev. 2020, 120, 683-733. DOI: 10.1021/acs.chemrev.9b00230.
ZHU Xing, et al. "Perovskites as Geo-inspired Oxygen Storage Materials for Chemical Looping and Three-Way Catalysis: A Perspective" ACS Catal. 2018, 8, 8213-8236. DOI: 10.1021/acscatal.8b0197.
Yusuf, Seif et al. "Effects of Sodium and Tungsten Promoters on Mg6MnO8-Based Core-Shell Redox Catalysts for Chemical Looping-Oxidative Dehydrogenation of Ethane" ACS Catal. 2019, 9, 3174-3186. DOI: 10.1021/acscatal.9b00164.
R. Burch et al. "Investigation of the synthesis of oxygenates from carbon monoxide/hydrogen mixtures on supported rhodium catalysts" Catalysis Research Group, Chemistry Department, University of Reading, Whiteknights, Reading, 1992. Elsevier Science Publishers B.V., Amsterdam.
Mishra, Amit et al. "Rh promoted perovskites for exceptional "low temperature" methane conversion to syngas" Deptarment of Chemical and Biomolecular Engineering, North Carolina State University. 2019 https://doi.org/10.1016/j.cattod.2019.05.036.
Diagne, C. et al. "Promoting Effects of Lithium on Pd/Ce02 Catalysts in Carbon Monoxide-Hydrogen Reactions" 1989. p. 165-180 Elsevier Science Publishers B.V., Amsterdam.
Orita, Hideo et al. "Improvement of Selectivity for C2-Oxygenated Compounds in CO—H2 Reaction Over TiO2-SUPPORTED Rh Catalysts by Doping Alkali Metal Cations" Chemistry Letters, pp. 1161-1164, 1983. The Chemical Society of Japan.
Ye, Run-Ping et al. "CO2 hydrogenation to high-value products via heterogeneous catalysis" Nature Communications. https://doi.org/10.1038/s41467-019-13638-9 (2019).
Shafiefarhood, Ayra et al. "Rh-promoted mixed oxides for "low-temperature" methane partial oxidation in the absence of gaseous oxidants" 2017. J. Mater. Chem. A, 2017, 5, 11930. DOI: 10.1039/c7ta01398a.
Kitco. Vault Chain Chart "Rhodium Chart" Oct. 19, 2021 http://www.kitco.com/charts/rhodium.html.
Kagami, S. et al. Formation of C(2)-Oxygenated Compounds from the Reaction of CO and H, over Alkali-metal Doped Rhodium Catalysts under Mild Conditions. (1983) p. 256-257. J. Chem. Soc., Chem. Commun.
Nathan Galinsky, et al., "Ca1-xAxMnO3 (A=Sr and Ba) perovskite based oxygen carriers for chemical looping with oxygen uncoupling (CLOU)", Applied Energy 157 (2015), pp. 358-367.
Feng He, et al., "Perovskite promoted iron oxide for hybrid watersplitting and syngas generation with exceptional conversion", Energy Environ. Sci., 2015, vol. 8, pp. 535.
Nathan Galinsky, et al., "CaMn1-xBxO3-∂ (B=Al, V, Fe, Co, and Ni) perovskite based oxygen carriers for chemical looping with oxygen uncoupling (CLOU)", Applied Energy 174 (2016), pp. 80-87.
Amit Mishra, et al., "Perovskite-structured AMnxB1-xO3 (A=Ca or Ba;B=Fe or Ni) redox catalysts for partial oxidation of methane", Catal. Sci. Technol. 2016, vol. 6, pp. 4535-4544.
Seif Yusuf, et al., "Effect of Promoters on Manganese-Containing Mixed Metal Oxides for Oxidative Dehydrogenation of Ethane via a Cyclic Redox Scheme", .ACS Catalysis, 2017, vol. 7, pp. 5163-5173.
Chinese Office Action CN Application No. 201780057258.7 dated Sep. 5, 2022.

* cited by examiner

REDOX CATALYSTS FOR THE OXIDATIVE CRACKING OF HYDROCARBONS, METHODS OF MAKING, AND METHODS OF USE THEREOF

CROSS-REFERENCE TO RELATED APPLICATIONS

This application is the 35 U.S.C. 0.371 national stage application of PCT Application No. PCT/US/2017/051157, filed Sep. 12, 2017, where the PCT claims priority to, and the benefit of, U.S. provisional application entitled "REDOX CATALYSTS FOR OXIDATIVE CRACKING OF HYDROCARBONS, METHODS OF MAKING, AND METHODS OF USE THEREOF" having Ser. No. 62/393, 411, filed Sep. 12, 2016, both of which are incorporated herein by reference in their entireties.

STATEMENT REGARDING FEDERALLY SPONSORED RESEARCH OR DEVELOPMENT

This invention was made with government support under grant number 1254351 awarded by the National Science Foundation. The government has certain rights in this invention.

TECHNICAL FIELD

The present disclosure generally relates to metal oxide redox catalysts.

BACKGROUND

Olefins and di-olefins such as ethylene, propene, 1-butene, and 1,3 butadiene are major feedstocks for the petrochemical industry, particularly in the production of plastics and synthetic rubbers. Olefins are typically produced from the "cracking" or thermal decomposition of light hydrocarbons such as natural gas liquids (mostly saturated C2-C5 hydrocarbons) which are low value byproducts of natural gas production and naphtha, a low boiling point fraction of petroleum (~30-145° C.) that is rich in highly-volatile, linear paraffins that are not suitable for liquid fuel use without extensive processing. The high temperature decomposition process, referred to as pyrolysis, or (steam) cracking, is highly energy intensive, leading to large fuel demands and concomitant $CO_2$ and $NO_x$ emissions.

The production of ethylene and other olefins from natural gas liquids and naphtha, is very attractive as olefins are important feedstocks for many commodity chemicals such as various types of polyethylene, polyvinyl chloride, ethylene oxide styrene, and synthetic rubbers. Compared to conventional steam cracking which is energy and pollutant intensive, the oxidative dehydrogenation (ODH) represents a promising alternative due to the exothermicity of the reaction and its potential to achieve high single-pass ethane conversion.

A number of catalyst systems are shown to be active for the ODH reaction. These include supported V and Mo based oxides, rare-earth-metal oxides, Pt group metals, and many other mixed oxides. Most ODH reactions are carried out in the presence of gaseous oxygen between 400 and 700° C. While still remaining a focal research area, catalytic ODH with oxygen co-feed faces several challenges: (i) Co-feeding gaseous oxygen with ethane leads to potential safety hazards; (ii) Oxygen produced from cryogenic air separation is costly and energy-intensive; (iii) Electrophilic surface oxygen species such as $O^-$ and $O_2^-$ formed from adsorbed gaseous oxygen can limit the selectivity of the ODH reaction.[13,14] Due to these issues, alternative schemes that are capable of converting ethane in absence of gaseous oxygen are highly desirable.

In addition to oxidation reactions in the presence of gaseous oxygen, a cyclic reduction-oxidation (redox) scheme has been investigated for both combustion and selective oxidation reactions under a so-called chemical looping process.[15,16] Such an approach can circumvent the needs for air separation by splitting an oxidation reaction into two steps: In step one, hydrocarbon feedstock is oxidized with the lattice oxygen of an oxygen carrier, also known as redox catalyst. The (partially) reduced redox catalyst is subsequently regenerated with air in step two, regaining its lattice oxygen while producing heat. One such example is the vanadium pyrophosphate (VPO) redox catalyst developed by DuPont for oxidation of butane to maleic anhydride.[13] A major challenge for this process was the low activity and oxygen capacity of the redox catalysts.[17] Supported vanadium oxides were also investigated for ethane ODH under the redox mode: a study using $VO_x/c\text{-}Al_2O_3$ redox catalyst under the fluidized bed condition achieved an ethylene selectivity of 84.51% at 6.47% ethane conversion. The selectivity decreased with increasing conversion due to CO and $CO_2$ formation (57.6% ethylene selectivity at 27.6% ethane conversion). Attempts have also been made through the addition of promoters such as $MoO_x$[20] or $ZrO_2$[21] to the $VO_x$-based redox catalysts. Although slightly improved performances were obtained, the selectivity/conversions were still unsatisfactory due to the lack of activity for the redox catalysts.

First row transition metal oxides such as those containing Fe and Mn are frequently investigated for chemical looping processes due to their satisfactory oxygen carrying capacity and low cost. However, they tend to be non-selective, leading to complete oxidation of hydrocarbons. One strategy to improve the selectivity of redox catalyst is to encapsulate iron oxide particles within a selective and mixed-conductive perovskite shell.[25,26] As such, oxide core is used to store and supply lattice oxygen without direct contact with the fuel. Since the selectivity of this redox catalyst is determined by surface chemistry rather than the oxide core, higher syngas selectivity from methane oxidation can be achieved. In addition to methane oxidation, perovskites can catalyze a number of other oxidation reactions.[27,28,29] Dai et al. doped chloride into LSF to occupy oxygen vacancies and achieved good selectivity for ODH reaction under an oxygen co-feed mode.[29] However, this catalyst was not found to be stable and was not demonstrated under a chemical-looping mode. In addition to halides, alkali metals are also widely studied for ODH reactions. Lunsford et al. investigated chloride and lithium promoted MgO and achieved an ethylene yield of 45% in the presence of gaseous oxygen.[30] Chloride was reported to reduce the charge on $O^-$ centers and increase the selectivity. The active center in this system was generally ascribed to $[Li^+O^-]$.[31] Gartner et al. reported a $MgO/Dy_2O_3$ supported molten alkali metal chloride with ethylene selectivity up to 95%.[32] The active center was proposed to be $OCl^-$ rather than coordinatively unsaturated cations.[32,33]

There remains a need for improved redox catalysts and methods of making and using thereof that overcome the aforementioned deficiencies.

SUMMARY

A variety of redox catalysts, methods of making, and methods of using thereof are provided that overcome the aforementioned deficiencies.

In various embodiments, surface modified redox catalysts are provided having an oxygen carrier core with an outer surface that has been modified to enhance the selectivity of the redox catalyst for oxidative dehydrogenation, e.g. to provide improved selectivity for oxidative dehydrogenation as compared to the otherwise same catalyst under the otherwise same conditions except without the surface modification. The surface modification can include forming a redox catalyst outer layer on the outer surface, e.g. to form a core-shell structure or more generally an oxygen carrier with a modified/promoted surface. In some embodiments, the surface modification includes suppressing sites that form nonselective electrophilic oxygen sites on the outer surface of the oxygen carrier, e.g. by providing a dopant or promoter to modify the surface chemistry of outer layer e.g. the a perovskite such as $La_{0.6}Sr_{1.4}FeO_4$ (which alone is selective for deep oxidization of light olefins) $LiFeO_2$ causing the formation of a $Li_2O/LiFeO_2$ shell that suppresses deep oxidation.

The oxygen carrier or oxygen carrier core can contain a metal oxide having a defected rock salt structure such as metal oxides having the chemical formula $M_{1-x}O$ where M is Mg, Ca, Sr, Ba, Mn, Fe, Ni, or a combination thereof. For example, the oxygen carrier can include $Mg_6MnO_8$. The oxygen carrier can include a $Mg_6MnO_8$ phase, a $Mn_2O_3$ phase, a mixed manganese-magnesia oxide phase such as $(Mn,Mg)_3O_4$, an alkaline-manganese oxide phase such as $Li_{1-x}MnO_{2-\delta}$ or a combination thereof.

The oxygen carrier or oxygen carrier core can include a perovskite. The perovskite can have the chemical formula $ABO_{3-\delta}$ where A is Ca, Sr, Ba, Sc, Y, La, Ce, or a combination thereof, and where B is a transition metal such as Fe, Ni, Mn, or a combination thereof. The perovskite can be $CaMnO_{3-\delta}$.

The included perovskite can be a B-site deficient perovskite having a Ruddlesden-Popper/Brownmillrite structure. The B-site deficient perovskite can have the chemical formula $(La,A)_n(Fe,B)_n(Fe,B)_{n-1}O_{3n-1}$, where A is selected from the group consisting of Ca, Sr, Ba, Sc, Ce, and a combination thereof, B is selected from the group consisting of Ti, Ni, Mn, and a combination thereof, and n is an integer from 1 to 3. The B-site deficient perovskite can be $La_{0.6}Sr_{1.4}FeO_4$ or $Sr_3Fe_2O_7$.

In various embodiments, the surface modification includes a dopant or promoter on the outer surface such as Li, Na, K, Cs, Rb, P, S, B, Cr, Pt, Sn, Pd, Mo, W, Ta, V, Ce, La, Pr, Sm, Y, Bi, Sb, Pb, Sr, Ba, Ca, Cl, Br, and/or F alone or in combination that suppress deep oxidation and or catalytically enhance the dehydrogenation of hydrocarbons.

A variety of redox catalysts can be used in the compositions and methods described herein. In various embodiments, the redox catalyst has a core-shell structure with a redox catalyst outer layer, and the redox catalyst outer layer includes a mixed-metal-oxide redox catalyst such as $LiFeO_2$, $CaMnO_3$, and $Sr_3Fe_2O_7$.

In some embodiments a co-catalyst that has activity for non-oxidative dehydrogenation of paraffins is used. This may be produced by the wet incipient impregnation of an inert porous support with suitable precursor solutions, such as platinum nitrate and tin chloride or chrome nitrate. The support may be based on alumina or basic materials such as zinc aluminate and promoters such as Sn can be added. After the sample is dried and then calcined at or above 500° C., the metal oxide is left on the inert support. This co-catalyst may be used either mixed with the oxygen carrier (composite bed mode), or place before and after an oxygen carrier bed (triple bed mode) that selectively combusts hydrogen. Under the former mode, hydrogen is burned on-site, whereas under the latter mode, hydrogen is selectively burned in the oxygen carrier bed. For both modes, a conversion higher than the equilibrium conversion could be achieved at a given reaction temperature.

The redox catalysts can be made in a variety of sizes, although in some embodiments the catalysts are nanoparticles having a diameter of about 50 nm to about 500 nm. In some embodiments, where the catalyst has a core-shell catalyst structure, the outer layer on the core-shell redox catalyst can be very thin, e.g. having a thickness of about 25 nm, about 15 nm, about 10 nm, about 5 nm, or less. In some embodiments, where the catalyst has a core-shell catalyst structure, the redox catalyst outer layer and the oxygen carrier can be present at a molar ratio (redox catalyst/oxygen carrier) of about 0.5 to 2.5.

A variety of methods are provided for making the surface modified redox catalysts. The methods can include modified Pechini methods. For example, the methods can include dissolving a mixture of metal citrate salts in an aqueous solution to form a chelating solution, adding ethylene glycol to the chelating solution to form a gel, drying the gel, and calcining the gel at an elevated temperature for a period of time to produce the core-shell redox catalyst. The mixture of metal citrate salts can include oxygen carrier metal precursors. In some embodiments, the chelating solution can include redox catalyst metal precursors that can form a redox catalyst shell on the outer surface of the oxygen carrier core. In some embodiments, the methods can include impregnating the outer surface of the oxygen carrier with a redox catalyst, dopant, and/or promoter. The methods can include forming a gel by the addition of ethylene glycol at a molar ratio of about 2:1 based upon the amount of citric acid in the metal citrate salts. To produce a redox catalyst outer shell, the molar ratio of the redox catalyst metal precursors to the oxygen carrier metal precursors can be about 0.5 to 2.5. The calcining step can be performed, in some aspects, at an elevated temperature of about 900° C. to 1100° C. and/or for a period of time from about 8 to 20 hours.

In some embodiments the redox catalyst catalysts, or oxygen carrier core can be prepared by the slurry method in which the solid metal precursors and soluble precursor salts are physically mixed with water, and milled in a ball mill. The resulting slurry can be dried and calcined from 900 to 1100° C. In other embodiments a metal oxide, or a previously make oxygen carrier is impregnated with a solution of another metal nitrate precursor or other suitable salt. The sample can be calcined from 900 to 1100° C.

A variety of methods are provided for using the catalysts provided herein for oxidative cracking of light paraffins. In various embodiments, methods are provided for oxidative cracking of light paraffins by contacting the paraffin with a core-shell redox catalyst described herein to convert the paraffins to water and olefins, diolefins, or a combination thereof. The light paraffins can include paraffins having from 2 to 7 carbon atoms. For example, the paraffins can include ethane, propane, or a combination thereof. In some embodiments, the light paraffins include ethane that is converted into ethylene at a temperature of about 750° C. or less. In some embodiments, the light paraffins include propane that is converted into propylene without producing or while producing an insignificant amount of ethylene byproducts. Steam and/or $CO_2$ can, in some aspects, be added to provide additional oxygen when the paraffin is contacted with the core-shell redox catalyst.

The oxygen consumed in the oxidative cracking can be replenished by a variety of methods. In some embodiments, the methods include regenerating the redox catalyst by contacting the core-shell redox catalyst with an oxidizing gas, thereby regenerating oxygen in the core-shell redox catalyst and producing heat, $H_2$, CO, or a combination thereof. The oxidizing gas can include air, $CO_2$ steam, or a combination thereof.

The oxidative cracking methods provided herein can be performed in a circulating fluidized bed reactor. In some embodiments, the methods are performed in a reactor having two or more parallel beds containing the redox catalyst to maintain heat transfer between the two or more parallel beds, wherein when half of the beds are being contacted with the paraffins, the other half are being contacted with oxidizing gas to regenerate the oxygen in the core-shell redox catalyst, and wherein the heat produced from the oxygen regeneration is provided to assist the cracking of the light paraffins to produce the water and olefins, diolefins, or a combination thereof.

In various embodiments, the ability of the redox-catalyst to selectively oxidize saturated light hydrocarbons such as ethane, propane and hexane, and/or the hydrogen produced from separate dehydrogenation reactions at these temperatures allows high per-pass conversions relative to non-oxidative processes by eliminating thermodynamic equilibrium limits. In various embodiments, the redox catalyst is sufficiently selective to the formation of water over $CO_2$ and CO, such that at least 20% (>50% more typical for NGL's) of the energy produced in regeneration is supplied from the regeneration of oxygen that produces water, in contract to CO or $CO_2$ or from the burning of coke. In some embodiments, the hydrogen formed from paraffin dehydrogenation is selectively combusted by an oxygen carrier which is either physically mixed with a hydrogenation catalyst or placed between two hydrogenation catalyst beds. In either case, the lattice oxygen of the oxygen carrier selectively burns hydrogen and has little activity toward paraffin oxidation. In some embodiments, the per-pass yield of valuable products, such as olefins, di-olefins and aromatics, are comparable or higher than steam cracking, with consumption of less valuable paraffins providing heat generation through $CO_x$ formation. In some embodiments, the methods include recycling of methane, CO, and or $CO_2$ into the reactor, wherein the formation of undesired byproducts is partially or fully suppressed.

For example, in some embodiments, lithium promoted perovskite redox catalysts are synthesized and characterized for CL-ODH of ethane. The redox catalysts are tested under both a transient pulse mode as well as a step redox mode, up to 61% ethane conversion and 90% ethylene selectivity is achieved. Powder X-ray diffraction (XRD) characterization shows that the redox catalyst is a composite of B-site deficient $La_xSr_{2-x}FeO_{4-\delta}$ (LSF) perovskite and $LiFeO_2$. X-ray photoelectron spectroscopy (XPS) analysis indicates lithium enrichment on the redox catalyst surface, which is determined to be $Li_2O$ by transmission electron microscopy (TEM). The XPS O 1s spectra and $O_2$-TPD (temperature-programmed desorption) show a suppression of surface oxygen species after Li addition. This suppression is likely to be due to a Li cation enriched surface layer. Under reactive conditions, surface enrichment of Li cation decreases the rate of $O^{2-}$ conduction from the bulk and its evolution into the non-selective electrophilic (surface) oxygen species. Broadened ethane pulse with sharp oxygen pulse injection is further performed to confirm the non-selective nature of surface oxygen species in ODH reaction.

The findings indicate that that ODH selectivity can potentially be improved by surface modification and controlling the $O^{2-}$ conduction and evolution in redox catalysts. The catalyst and methods provided herein can be highly selective for oxidative dehydrogenation of light paraffins. In some embodiments, the selectivity for dehydrogenation of light paraffins greater than the selectivity of the otherwise same catalyst except without the surface modifications, e.g. when used in the otherwise same method and under the otherwise same conditions.

Other systems, methods, features, and advantages of redox catalysts and methods of making and using thereof will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

(FIG. 1B) product eluted from $CaMnO_3$ contacted with 5% ethane; (FIG. 1C) inert free product of 5% ethane over $Cr/Al_2O_3$; (FIG. 1D) inert free product of 5% ethane over bifunctional catalytic bed containing $CaMnO_3$ and $Cr/Al_2O_3$ co-catalysts.

FIG. 3A is a diagram of two parallel packed beds with manifolds switching from hydrocarbon to air feeds. FIG. 3B is a side view cross-section of multiple packed beds in same reactor, FIG. 3C is an overhead view of paralleled packed beds showing the manifold switching beds between purge, oxidation/regeneration, and oxy-cracking.

(FIG. 20B) Instantaneous selectivity/conversion/yield (Left Y-axis) and cumulative oxygen release (Right Y-axis) obtained on LSF; and (FIG. 20C) Conversion profile for 2.5LiFeO$_2$-LSF under a 3 min reduction half-cycle: Temperature=700° C.; Cycle number=8.

FIG. 32B is a high magnification TEM micrograph of 2.5K—LaSrFe for the square area depicted in the TEM image from FIG. 32A.

DETAILED DESCRIPTION

Figure 1A:
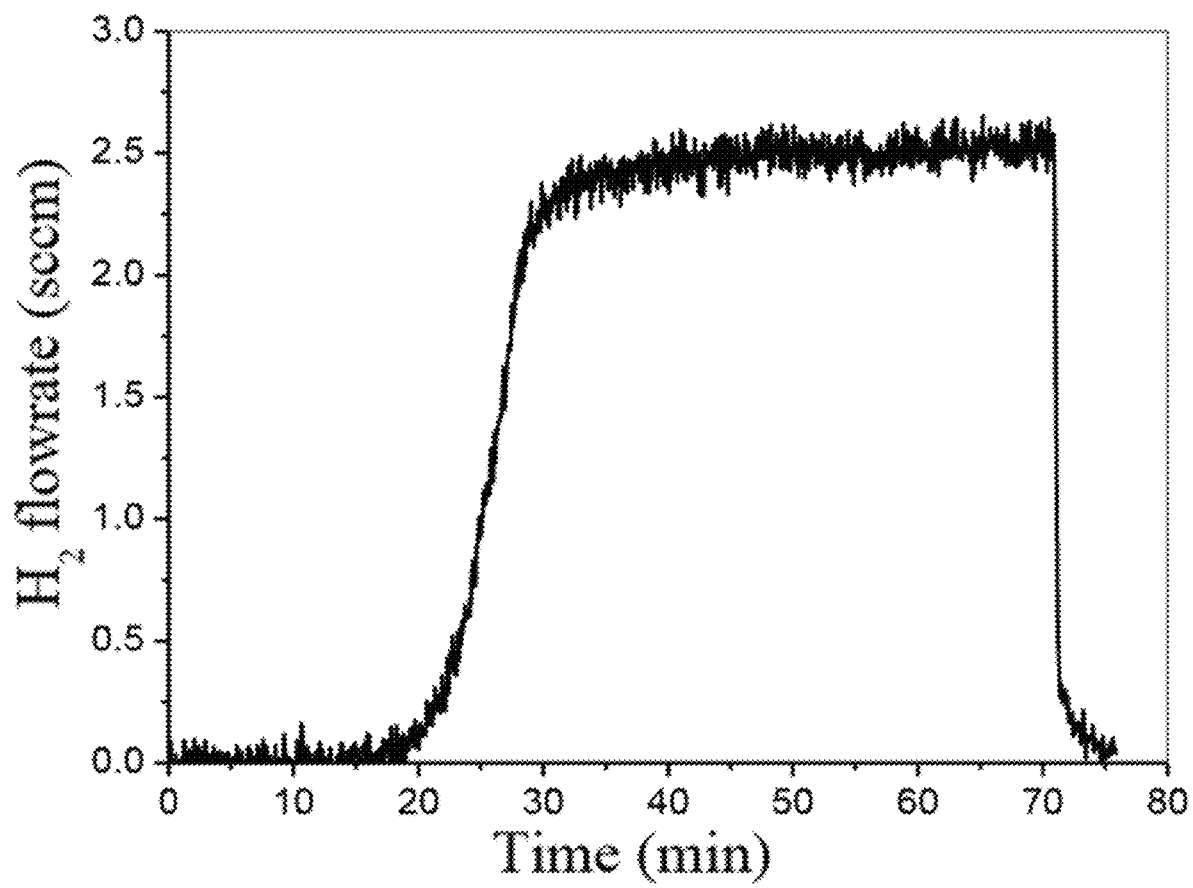
FIGS. 1A-1D show a Mass Spectroscopy response of (FIG. 1A) hydrogen eluted from 0.5 g of $CaMnO_3$ contacted with 5% hydrogen.
Figure 1B:
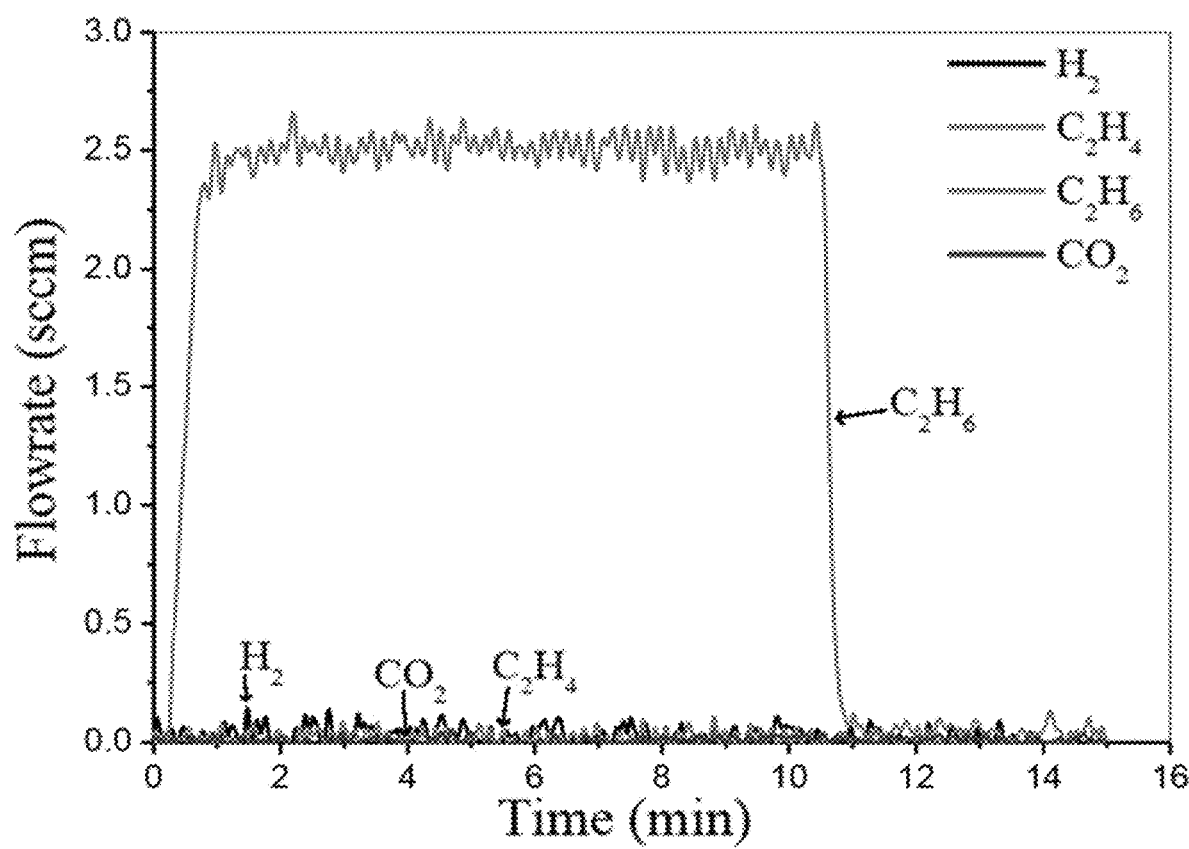
Figure 1C:
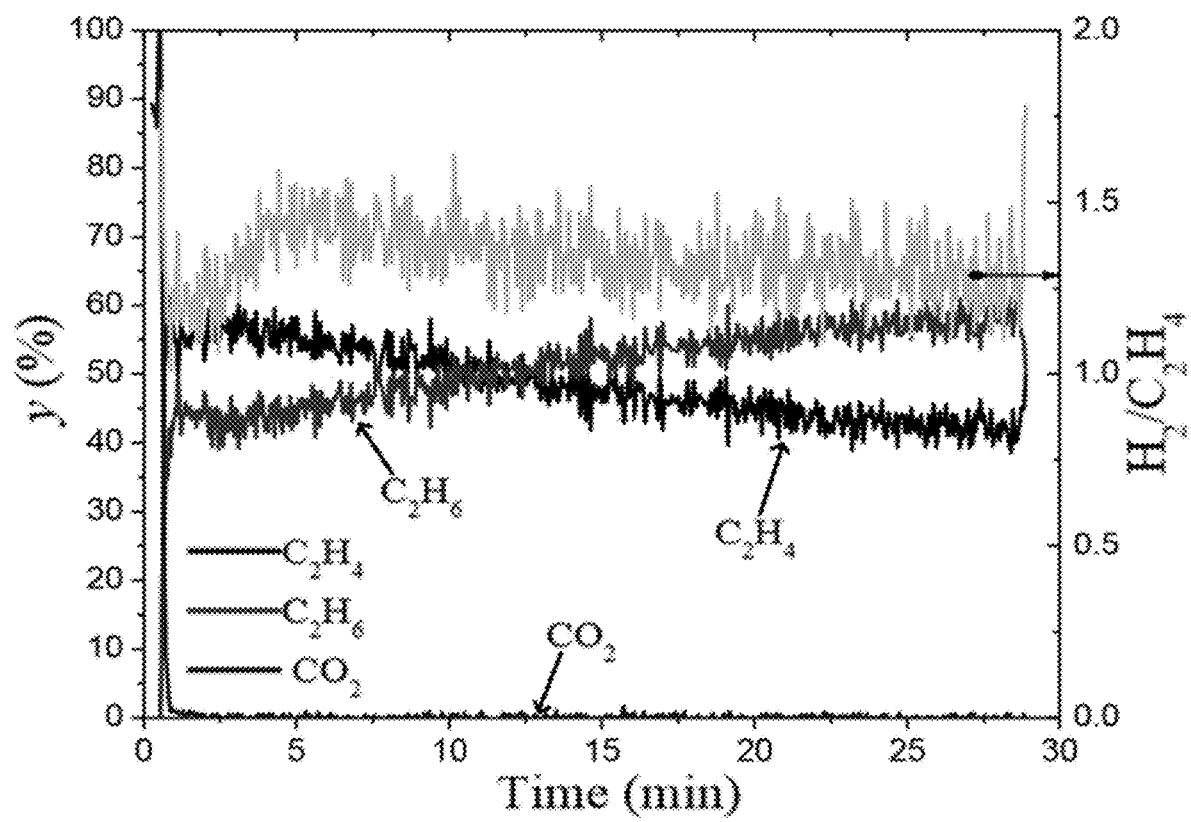
Figure 1D:
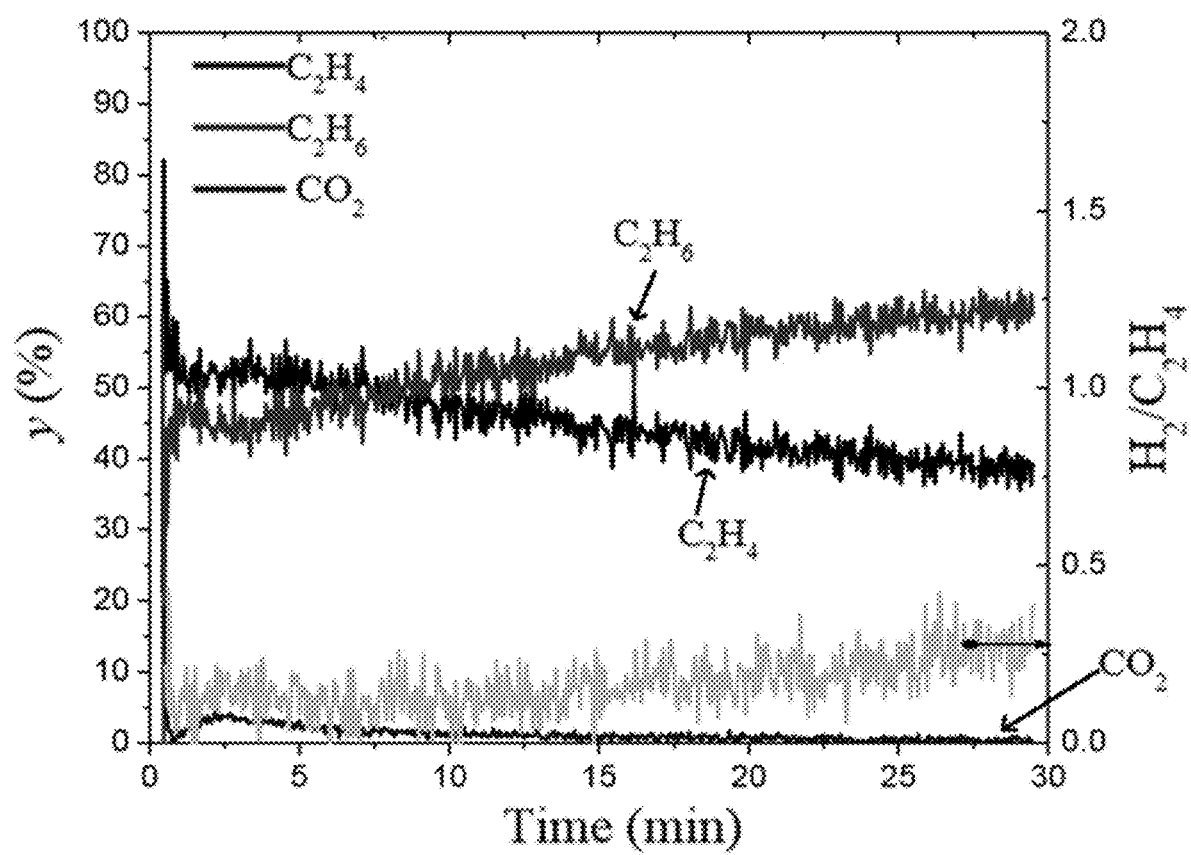
Figure 2:
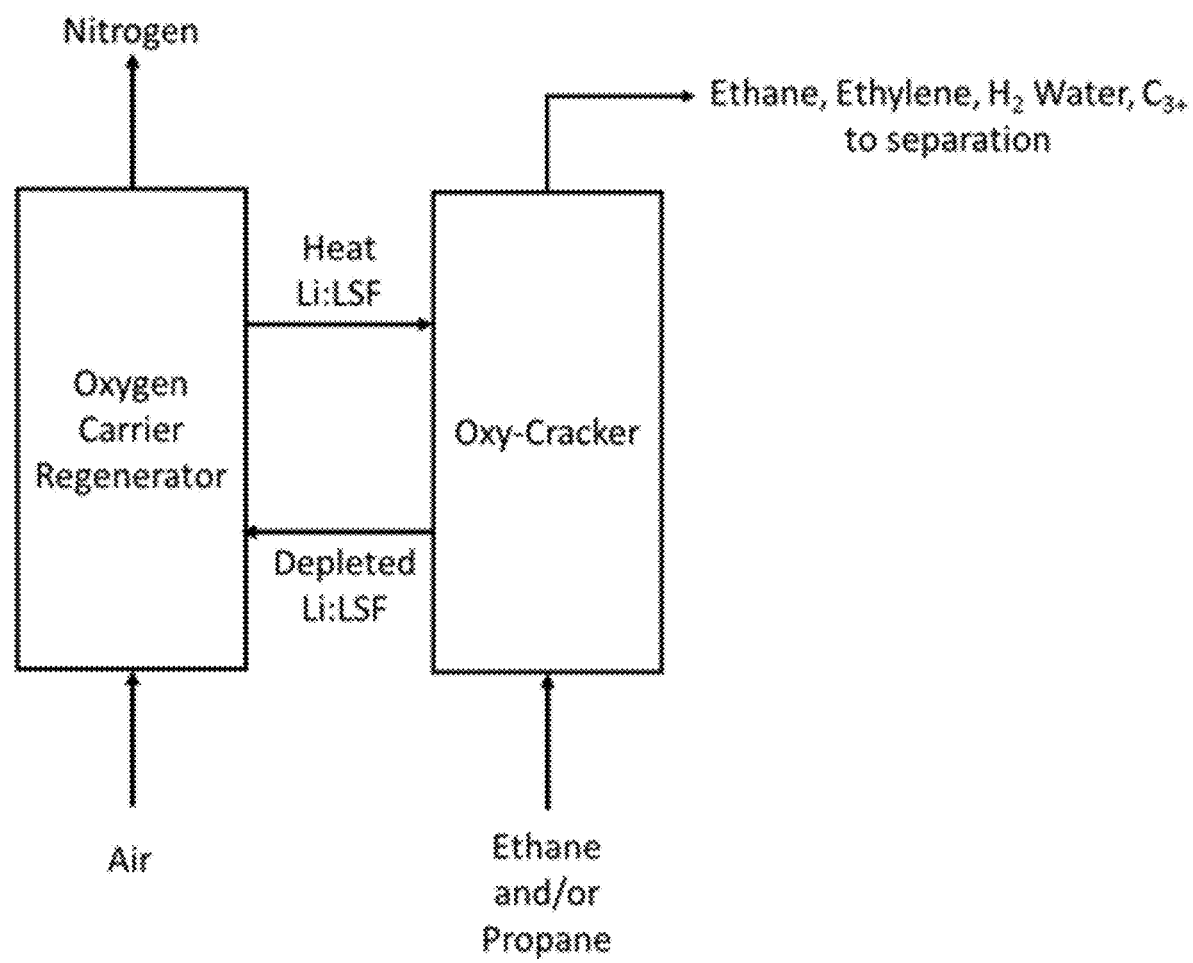
FIG. 2 shows a circulating fluidized bed configuration of oxy-cracking/ODH.

Olefins and di-olefins such as ethylene, propene, 1-butene, and 1,3 butadiene are major feedstocks for the petrochemical industry, particularly in the production of plastics and synthetic rubbers. Olefins are typically produced from the "cracking" or decomposition of light hydrocarbons such as natural gas liquids (mostly saturated C2-C5 hydrocarbons) which are low value byproducts of natural gas production and light naphtha, a low boiling point fraction of petroleum (~30-145° C.) that is rich in highly-volatile, linear paraffins that are not suitable for liquid fuel use without extensive processing. The high temperature decomposition process, referred to as pyrolysis, or (steam) cracking, is highly energy intensive, leading to large fuel demands and concomitant CO$_2$ and NO$_x$ emissions. In various embodiments provided herein, a system of catalysts for oxidative cracking (also known as oxy-cracking or oxidative dehydrogenation) in which the saturated hydrocarbons are selectively oxidized to produce olefins and water. In this redox catalytic system, the oxygen is provided by an oxygen carrier (a.k.a redox catalyst). In some embodiments, this redox catalyst is designed to supply its lattice oxygen to paraffin conversion reactions at temperatures lower than 800° C. and/or maintains high selectivity at temperatures higher than 800° C. The lattice oxygen can be replenished with air or other suitable oxidizing gas such as CO$_2$ or steam.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

Redox Catalysts

In various embodiments, redox catalysts are provided having an oxygen carrier core with one or more surface modifications to enhance the selectivity of the redox catalyst for oxidative dehydrogenation. The surface modifications can include forming a redox catalyst outer layer on the outer surface of the oxygen carrier core to form a catalyst having a core-shell structure. The surface modification can include suppressing sites that form nonselective electrophilic oxygen sites on the outer surface, e.g with dopants or promoters. The redox catalyst can have a surface that is doped and/or surrounded by a selective redox catalyst outer layer. The oxygen carrier core can contain a metal oxide having a defected rock salt structure such as metal oxides having the chemical formula $M1_nM2_mO_{1-x}$ where M1 and M2 are Mg, Ca, Sr, Ba, Mn, Fe, Ni, or a combination thereof. For example, the oxygen carrier can include $Mg_6MnO_8$. The oxygen carrier can include a $Mg_6MnO_8$ phase, a $Mn_2O_3$ phase, a mixed manganese-magnesia oxide phase such as $(Mn,Mg)_3O_4$, an alkaline-manganese oxide phase such as $Li_{1-x}MnO_{2-\delta}$, or a combination thereof.

The oxygen carrier or oxygen carrier core can include a perovskite. The perovskite can have the chemical formula $ABO_{3-\delta}$ where A is Ca, Sr, Ba, Sc, Y, La, Ce, or a combination thereof, and where B is a transition metal such as Fe, Ni, Mn, or a combination thereof. The perovskite can be $CaMnO_{3-\delta}$.

The perovskite can be a B-site or oxygen deficient perovskite having a Ruddlesden-Popper/Brownmillrite structure. The B-site deficient perovskite can have the chemical formula $(La,A)_n(Fe,B)_{n-1}O_{3n-1}$, where A is selected from the group consisting of Ca, Sr, Ba, Sc, Ce, and a combination thereof, B is selected from the group consisting of Ti, Ni, Mn, and a combination thereof, and n is an integer from 1 to 3. The B-site deficient perovskite can be $La_{0.6}Sr_{1.4}FeO_4$ or $Sr_3Fe_2O_7$.

In various embodiments, the surface modification includes a dopant or promoter on the outer surface such as Li, Na, K, Cs, Rb, P, S, B, Cr, Mo, W, Ta, V, Ce, La, Pr, Sm, Y, Bi, Sb, Pb, Sr, Ba, Ca, Cl, Br, and/or F alone or in combination that suppress deep oxidation and or catalytically enhance the dehydrogenation of hydrocarbons.

A variety of redox catalysts can be used in the compositions and methods described herein. In various embodiments, the redox catalyst outer layer includes a mixed-metal-oxide redox catalyst such as $LiFeO_2$, $CaMnO_3$, and $SrFe_2O_7$. The redox catalysts can be made in a variety of sizes, although in some embodiments the catalysts are nanoparticles having a diameter of about 50 nm to about 500 nm. In some embodiments, where the redox catalyst has a core-shell catalyst structure, the outer layer can be very thin, e.g. having a thickness of about 25 nm, about 15 nm, about 10 nm, about 5 nm, or less. The redox catalyst outer layer and the oxygen carrier can be present at a molar ratio (redox catalyst/oxygen carrier) of about 0.5 to 2.5.

Methods of Making Redox Catalysts

A variety of methods are provided for making the redox catalysts. The methods of making the redox catalyst can include a sol-gel method, a co-precipitation method, a solid state reaction method, a freeze granulation method, a spray drying method, or a combination thereof.

The methods can include modified Pechini methods. The methods can include dissolving a mixture of metal citrate salts in an aqueous solution to form a chelating solution, adding ethylene glycol to the chelating solution to form a gel, drying the gel, and calcining the gel at an elevated temperature for a period of time to produce the core-shell redox catalyst. The mixture of metal citrate salts can include oxygen carrier metal precursors. In some embodiments, the chelating solution can include redox catalyst metal precursors that can form a redox catalyst shell on the outer surface of the oxygen carrier core. In some embodiments, the methods can include impregnating the outer surface of the oxygen carrier with a redox catalyst, dopant, and/or promoter.

The methods can include forming a gel by the addition of ethylene glycol at a molar ratio of about 2:1 based upon the amount of citric acid in the metal citrate salts. To produce a redox catalyst outer shell, the molar ratio of the redox catalyst metal precursors to the oxygen carrier metal precursors can be about 0.5 to 2.5. The calcining step can be performed, in some aspects, at an elevated temperature of about 900° C. to 1100° C. and/or for a period of time from about 8 to 20 hours.

Other methods can also be used to prepare the redox catalysts. These methods include the solid-state reaction method which involves mixing solids precursors in dry or slurry form followed with mixing, grinding, annealing, etc. The redox catalysts can also be prepared using co-precipitation, spray drying, or freeze granulation methods. Promoters or dopants can be added through blending, wet/dry impregnation, etc. In general the oxygen carriers in the redox catalysts are often in their stable thermodynamic states and any general methods that allow thorough mixing among metal cations followed with annealing will likely to result in suitable oxygen carriers.

Oxidative Cracking of Paraffins Using Redox Catalysts

A variety of methods are provided for using the catalysts provided herein for oxidative cracking of paraffins, especially light paraffins. In various embodiments, methods are provided for oxidative cracking of paraffins by contacting the paraffin with a redox catalyst described herein to convert the paraffins to water and olefins, diolefins, or a combination thereof. The paraffins can be light paraffins, heavy paraffins, or a combination thereof. The light paraffins can include paraffins having from 2 to 7 carbon atoms. For example, the paraffins can include ethane, propane, or a combination thereof. In some embodiments, the light paraffins include ethane that is converted into ethylene at a temperature of about 750° C. or less. In some embodiments, the light paraffins include propane that is converted into propylene without producing or while producing an insignificant amount of ethylene byproducts. Steam and/or $CO_2$ can, in some aspects, be added to provide additional oxygen when the paraffin is contacted with the core-shell redox catalyst. We note that a similar method can be used to convert liquid hydrocarbon in general via the oxy-cracking approach described herein.

The oxygen consumed in the oxidative cracking can be replenished by a variety of methods. In some embodiments, the methods include regenerating the redox catalyst by contacting the redox catalyst with an oxidizing gas, thereby regenerating oxygen in the redox catalyst and producing heat, $H_2$, CO, or a combination thereof. The oxidizing gas can include air, $CO_2$ steam, or a combination thereof.

The oxidative cracking methods provided herein can be performed in a circulating fluidized bed reactor. In some embodiments, the methods are performed in a reactor having two or more parallel beds containing the core-shell redox catalyst to maintain heat transfer between the two or more parallel beds, wherein when half of the beds are being contacted with the paraffins, the other half are being contacted with oxidizing gas to regenerate the oxygen in the core-shell redox catalyst, and wherein the heat produced from the oxygen regeneration is provided to assist the cracking of the paraffins to produce the water and olefins, diolefins, or a combination thereof.

In various embodiments, the ability of the redox-catalyst to selectively oxidize saturated light hydrocarbons such as ethane, propane and hexane, and/or the hydrogen produced from separate dehydrogenation reactions at these temperatures allows high per-pass conversions relative to non-oxidative processes by eliminating thermodynamic equilibrium limits. In various embodiments, the redox catalyst is sufficiently selective to the formation of water over $CO_2$ and CO, such that at least 20% (>50% more typical for NGL's) of the energy produced in regeneration is supplied from the regeneration of oxygen that produces water, in contract to CO or $CO_2$ or from the burning of coke. In some embodiments, the hydrogen formed from paraffin dehydrogenation is selectively combusted by an oxygen carrier which is either physically mixed with a hydrogenation catalyst or placed between two hydrogenation catalyst beds. In either case, the lattice oxygen of the oxygen carrier selectively burns hydrogen and has little activity toward paraffin oxidation. In some embodiments, the per pass yield of valuable products, such as olefins, di-olefins and aromatics, are comparable or higher than steam cracking, with consumption of less valuable paraffins providing heat generation through $CO_x$ formation. In some embodiments, the methods include recycling of methane, CO, and or $CO_2$ into the reactor, wherein the formation of undesired byproducts is partially or fully suppressed.

In one embodiment of the reaction a circulating fluidized bed with is used to contact a redox catalyst provided herein with ethane in a low temperature (<800° C.) ODH reactor giving high yields of ethylene and water along with other valuable hydrocarbons. The catalyst may be deposited onto a ceramic support. After reduction the redox catalyst is circulated into a regenerator/air reactor where it is re-oxidized producing heat. The sensible heat of the regenerated catalyst is transferred back into the hydrocarbon reactor.

In another embodiments, a catalyst described herein is circulated but contacted with propane instead of ethane temperatures in the range of 600-750° C. In this embodiment propane is selectively converted to propylene with or without a significant ethylene byproduct, while water is formed by selective oxidation of the hydrogen coproduct. In this and other embodiments, sufficient heat may be generated when the catalyst is re-oxidized in air, that the system is thermally sufficient.

Figure 3A:
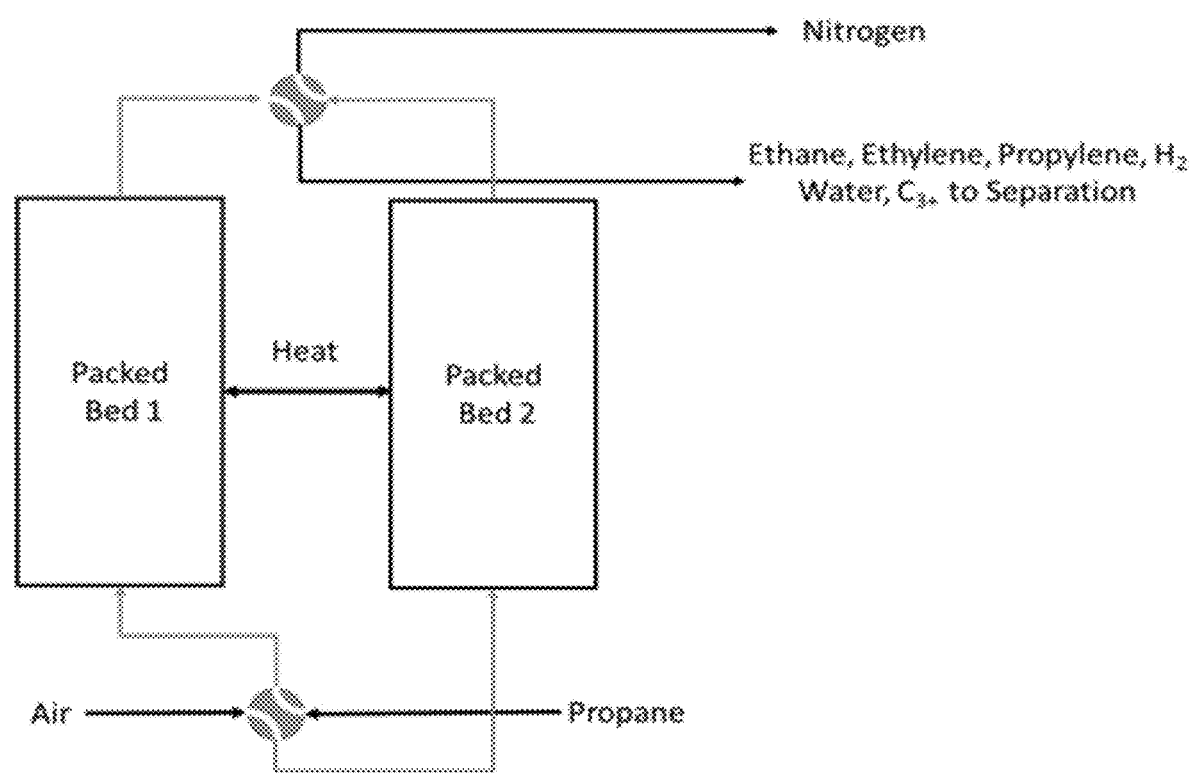
FIGS. 3A-3C show parallel packed bed configuration of chemical looping oxy-cracking reactors.
Figure 3B:
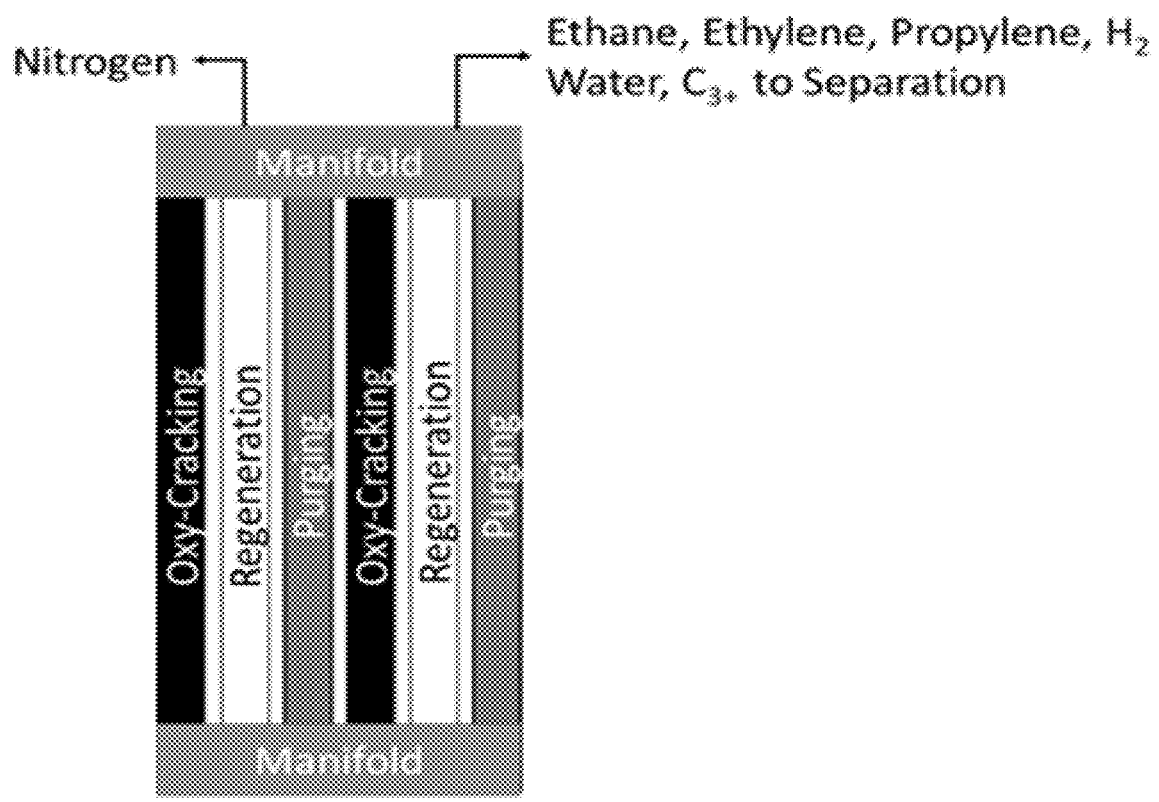
Figure 3C:
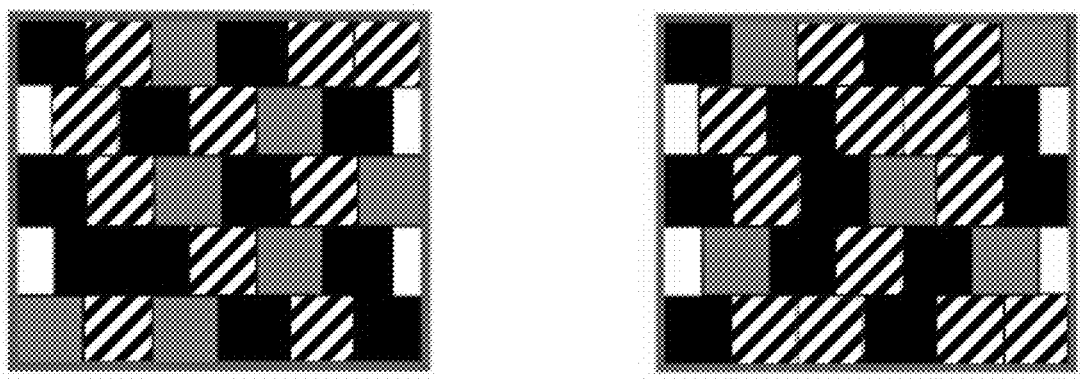

In another embodiment a catalyst described herein is packed into 2 or more parallel beds configured in a way to maintain facile heat transfer between the beds (FIGS. 3A-3C). While one or more bed undergoes reduction upon contact with propane forming high yields of propylene and water, an adjacent bed of reduced catalyst is regenerated in air. The heat from the exothermic regeneration bed flows into the endothermic hydrocarbon bed, maintaining the temperature of all of the reactors block. After the beds are depleted they are purged quickly then switched to the opposite environment (hydrocarbon to air and air to hydrocarbon). By continually switching the reactor is capable of operating under auto thermal conditions.

In another embodiment a configuration as described above is packed with a selective hydrogen combustion catalyst and a co-catalysts. The co-catalyst promote the non-oxidative dehydrogenation of propane, while the oxygen carrier selectively oxidizes the hydrogen. This configuration allows higher conversion at lower temperatures by both enhancing cracking kinetics and increasing equilibrium conversion to propylene. This may contain a physical mixture of co-catalysts, a bi-functional selective hydrogen combustion (SHC) and hydrogenation (DH) catalyst packed sequentially in the same bed, or in paralleled beds, with the valve manifold directing the gas flow between dehydrogenation and hydrogen oxidation beds sequentially.

A parallel packed bed configuration described herein can be placed upstream of an oligomerization unit to produce liquid feedstocks or fuels.

A circulating fluidized bed configuration, can be loaded with a catalyst described herein. In the hydrocarbon reactor the catalyst is contacted with heated naphtha. The paraffins such as n-pentane, n-hexane, and n-heptane, as well cycle hydrocarbons can be cracked to light olefins such as propylene and 1,3 butadiene. The hydrogen produced by the cracking reaction is consumed by the catalyst, while some of the paraffins (<20% of naphthalene mass) in the feed is oxidized. A high yield of valuable olefins and pyrolysis gasoline can be recovered.

In reactors configured such as described embodiment above, $CO_2$ (2-10 vol. % feed) and methane (1.5-20 vol % feed) byproducts can be recycled into the system and can result in suppressing the formation of undesirable products.

The catalyst and methods provided herein can be highly selective for oxidative dehydrogenation of paraffins, especially light paraffins. In some embodiments, the selectivity for dehydrogenation of paraffins is greater than the selectivity of the otherwise same catalyst except without the surface modifications, e.g. when used in the otherwise same method and under the otherwise same conditions.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1: Li Promoted $La_xSr_{2-x}FeO_{4-\delta}$ Core-Shell Redox Catalysts for Oxidative Dehydrogenation of Ethane Under a Cyclic Redox Scheme Chemical looping oxidative dehydrogenation (CL-ODH) of ethane utilizes a transition metal oxide based oxygen carrier, a.k.a. redox catalyst, to convert ethane into ethylene under an autothermal cyclic redox scheme. This example presents a Li promoted $La_xSr_{2-x}FeO_{4-\delta}$ (LSF) redox catalyst for CL-ODH reactions. While LSF without Li promoter exhibits low ethylene selectivity, addition of Li leads to high selectivity/yield and good regenerability. Up to 61% ethane conversion and 90% ethylene selectivity are achieved with Li promoted LSF. Further characterization indicates that the Li promoted LSF redox catalyst consists of $LiFeO_2$ (disordered rocksalt) and LSF (Ruddlesden-Popper) phases. Moreover, the surface of the redox catalysts is enriched with Li cation. It is also determined the LSF phase contributes to oxygen storage and donation whereas activity and selectivity of the redox catalysts are modified by the Li promoter: while oxygen for the CL-ODH reaction is supplied from the lattice of the LSF phase, the enrichment of Li cation on the surface increases the resistance for $O^{2-}$ diffusion from the bulk and its subsequent evolution into electrophilic oxygen species on the surface. The non-selective nature of the surface oxygen species and the inhibition effects of Li promoter on $O^{2-}$ diffusion are further confirmed by pulse experiments. The results demonstrate that Li promoted $La_xSr_{2-x}FeO_{4-\delta}$ is an effective redox catalyst for ethane ODH in absence of gaseous oxygen. Moreover, the selectivity of the redox catalysts can be enhanced by the alkali metal oxide promoters.

Experimental

Redox Catalysts Preparation

Addition of Li to $La_xSr_{1-x}FeO_{3-\delta}$ perovskites leads to formation of a B-site deficient $La_xSr_{2-x}FeO_{4-\delta}$ phase and a $LiFeO_2$ phase. To ensure comparability of the redox catalyst samples, Li-promoted redox catalysts are synthesized with varying ratios of $LiFeO_2$ and $La_xSr_{2-x}FeO_4$—. All redox catalysts were prepared by a modified Pechini method[25]. To synthesize LSF, stoichiometric amounts of $Fe(NO_3)_3 \cdot 9H_2O$ (98%, Sigma-Aldrich), $La(NO_3)_3 \cdot 6H_2O$ (99.9%, Sigma-Aldrich), $Sr(NO_3)_2$(99%, Noah chemical) were dissolved in deionized water under stirring at 30° C. Citric acid was then added to the solution at a 3:1 molar ratio to total metal ions ($Fe^{3+}$, $La^{3+}$ and $Sr^{2+}$). The solution was kept stirring at 50° C. for 0.5 h to form a chelating solution. Ethylene glycol was then added to the solution to promote gel formation. The molar ratio between ethylene glycol and citric acid was 2:1. The solution was kept at 80° C. under stirring until a viscous gel formed. The gel was dried overnight at 130° C. in a convection oven. The sample was then calcined in a tube furnace at 950° C. for 12 h under continuous air flow. In synthesis of Li promoted LSF, an additional amount of $LiNO_3$ (99.9%, Sigma-Aldrich) was added to the solution with stoichiometric amounts of $Fe(NO_3)_3 \cdot 9H_2O$, $La(NO_3)_3 \cdot 6H_2O$, $Sr(NO_3)_2$. As mentioned earlier, the amount of lithium precursor was expressed on the basis of the molar ratio between $LiFeO_2$ and LSF phases. The Li promoted redox catalysts were named as x-$LiFeO_2$/LSF, where x corresponded to the $LiFeO_2$/LSF molar ratio. $LiFeO_2$/$MgAl_2O_4$ was also synthesized as the reference sample. $MgAl_2O_4$ was chosen as the inert support material to increase the mechanical strength of redox catalyst. In the synthesis of $LiFeO_2$/$MgAl_2O_4$, 1 g of $LiFeO_2$ (95%, Sigma-Aldrich) was dissolved in water and incipient wet impregnated onto 1 g of $MgAl_2O_4$(99.9%, Noah Chemicals). The sample was dried in a convection oven at 130° C. overnight and then calcined in a tube furnace at 950° C. for 12 h under continuous air flow.

Redox Catalyst Characterization

XRD was conducted with a Rigaku SmartLab X-ray diffractometer to determine the redox catalyst crystal phases in oxidized and reduced states. The radiation source was a monochromatic CuK$_\alpha$ ($\lambda$=0.1542) with an operating condition at 40 kV and 44 mA. A step size of 0.05° and a scan step time of 1 s at 2θ=15-85° was used to generate the XRD patterns. The XRD patterns were processed using the International Center for Diffraction Data (ICDD) database in HighScore plus software.

XPS was used to analyze the near-surface composition of pure LSF and LSF promoted with different amounts of Li. The sample powder was pressed onto a carbon tape and outgassed at $10^{-5}$ Torr for overnight before it was introduced into the ultrahigh vacuum chamber for scanning. The XPS patterns were recorded on a PHOIBIS 150 hemispherical energy analyzer (SPECS GmbH) equipped with a non-monochromatic MgK$_\alpha$ excitation source (1254 eV). The data treatment was performed with the CasaXPS program (Casa Software Ltd., UK). The C 1s line at 284.6 eV was taken as a reference for binding energy calibration. Near surface compositions were calculated based on characteristic peak areas and their respective atomic sensitivity factors. It is noted that Li 1s and Fe 3p characteristic peaks overlap in the region of 52-59 eV. To calculate Li concentrations, the Fe 3p peak area was first calculated from the area ratio between Fe 2p and Fe 3p peaks of pure LSF. The Li 1s peak area was then obtained by subtracting the calculated Fe 3p peak area from the total peak area in the region of 52-59 eV.

BET surface areas were obtained with a Micromeritics ASAP 2020 accelerated surface area and porosity system via a multipoint physical adsorption measurement. Nitrogen was used as the adsorbate gas at the temperature of 77 K. Prior to analysis, 0.5-1 g of sample was degassed at 200° C. and 10 μm Hg for overnight.

$O_2$-TPD was carried out using a thermogravimetric analyzer (TGA) instrument to study the oxygen uncoupling of the redox catalysts.[34] 50-100 mg of sample was placed in a crucible inside the instrument chamber. Prior to analysis, the sample was pretreated at 850° C. for one hour and cooled down to room temperature under a continuous flow of 20% $O_2$ (100 ml·min$^{-1}$, balance Ar). The chamber was purged with pure Ar for another hour after the oxygen pretreatment. Then, the temperature was ramped up to 950° C. at a rate of 10° C./min under the flow of 100 ml·min$^{-1}$ pure Ar. $H_2$-TPR (temperature-programmed reduction) was also done by using 10% $H_2$ (200 ml·min$^{-1}$, balance Ar) with TGA instrument to determine the reducibility of the redox catalysts.[29] Prior to analysis, sample was pretreated at 850° C. for one hour and cooled down to room temperature under a continuous flow of 20% $O_2$ (100 ml·min$^{-1}$, balance Ar). The chamber was purged with 100 ml·min$^{-1}$ pure Ar for one hour after the oxygen pretreatment. Then, the temperature was ramped up to 750° C. at a rate of 5° C./min under the flow of 10% $H_2$ (200 ml·min$^{-1}$, balance Ar). The average chemical compositions of redox catalysts was determined by inductively couple plasma (ICP). TEM (JEOL JEM 2010F) was also performed at an accelerating voltage of 200 keV to obtain morphological information of the core-shell particle.

Reactive Testing

Reactivity tests were carried out under both a transient pulse mode and a continuous flow mode. In both testing modes, 0.5 g of the redox catalyst was placed in a fixed-bed quartz U-tube reactor (I.D.=⅛ inches) at atmospheric pressure. In order to minimize thermal conversion of ethane, inert silicon carbide or aluminum oxide was loaded on both sides of the U-tube to reduce the void volume.[35]

Transient pulse experiments were performed at 650, 675 and 700° C. The experimental setup was similar to what has been reported before.[36] 25 ml·min$^{-1}$ of helium was used as carrier gas, giving a space velocity of 3000 h$^{-1}$. Other space velocities were also tested. Pulses of 37.5% $C_2H_6$ (0.1 mL, balance Ar) were injected with 1 minute loading and 1 minute injection time. To investigate the behavior of the redox catalyst in ODH reaction and to confirm its regenerability, each $C_2H_6$ pulse was followed with a regeneration step of 37.5% oxygen (15 ml·min$^{-1}$, balance Ar) for 1 minute. Five reduction pulses and five oxygen regeneration steps were conducted on each redox catalyst to test its regenerability and repeatability. To study the evolution of catalytic performances, 10 consecutive ethane pulse were injected to reduce the redox catalysts, followed with a final step of oxygen regeneration. Finally, a broadened $C_2H_6$ pulse (broadened by sending a 0.1 mL injection through a 150 mL broadening tube) was injected coupled with a sharp pulse injection of $O_2$ (1 mL, balance Ar) to determine the role of gaseous oxygen in ODH reactions. The experimental setup was similar to a previous report.[36]

Continuous flow experiments were performed at 700° C. In reduction steps, the feed gas composition was 15 ml·min$^{-1}$ of ethane and 25 ml·min$^{-1}$ of Ar, giving a space velocity of 4800 h$^{-1}$. An oxidation step was followed with each reduction step, using 10% oxygen (5 ml·min-1, balance Ar). To investigate the on-line redox catalyst behavior and to measure the redox oxygen capacity, each reduction and oxidation step was performed for 5 minutes for 8 cycles, with a 5 minutes of Ar purging in between.

All products formed were monitored by a downstream quadruple mass spectrometer (QMS, MKS Cirrus II). They were quantified by integrating characteristic peaks of each species obtained from quadruple mass spectrometer. $C_2H_4$ formation was calculated by deducting the contribution of $C_2H_6$ to the mass 26 peak calculated by the characteristic ratio of mass 30 to mass 26 before calculating $C_2H_4$ concentration from mass 26. Coke formation was calculated by integrating the amount of CO and $CO_2$ formed during the regeneration step.[26] CO formation was calculated by deducting the contribution of $C_2H_6$, $C_2H_4$, and $CO_2$ characteristic peaks (Mass 30, Mass 26 and Mass 44, respectively) from CO characteristic peak (Mass 28). $H_2$ formation was also monitored by the quadruple mass spectrometer. However, the amount of hydrogen formation in pulse experiments was negligible, i.e. within the noise level of quadruple mass spectrometer measurements. To verify the data obtained from quadruple mass spectrometer, gas chromatography (GC, Agilent Technologies, 7890B) with Ar and He thermal conductivity detector (TCD) channels was also used to examine the formation of $H_2$, CO and coke. It was observed on quadruple mass spectrometer and GC that the amount of CO formation and coke formation were negligible for both pulse and continuous flow experiments. Ethane appears to be converted under two routes, the selective oxidation from ethane to ethylene and the deep oxidation from ethane to $CO_2$. The molar ratio of ethylene and $CO_2$ product formation to redox catalyst active oxygen consumption were stoichiometrically estimated to be 1/1 and 1/3.5, respectively. The oxygen capacity of redox catalysts were calculated by using such an oxygen mass balance. $H_2O$ is calculated from a hydrogen balance. To examine the selective combustion of $H_2$, $H_2O$ selectivity is calculated on the basis of the amount of $H_2O$ formation to the overall $H_2$ formation from cracking.[35] Ethylene selectivity and ethane conversion were calculated from product species distributions.

Results and Discussions

Reactive Testing of the Redox Catalysts

Figure 4:
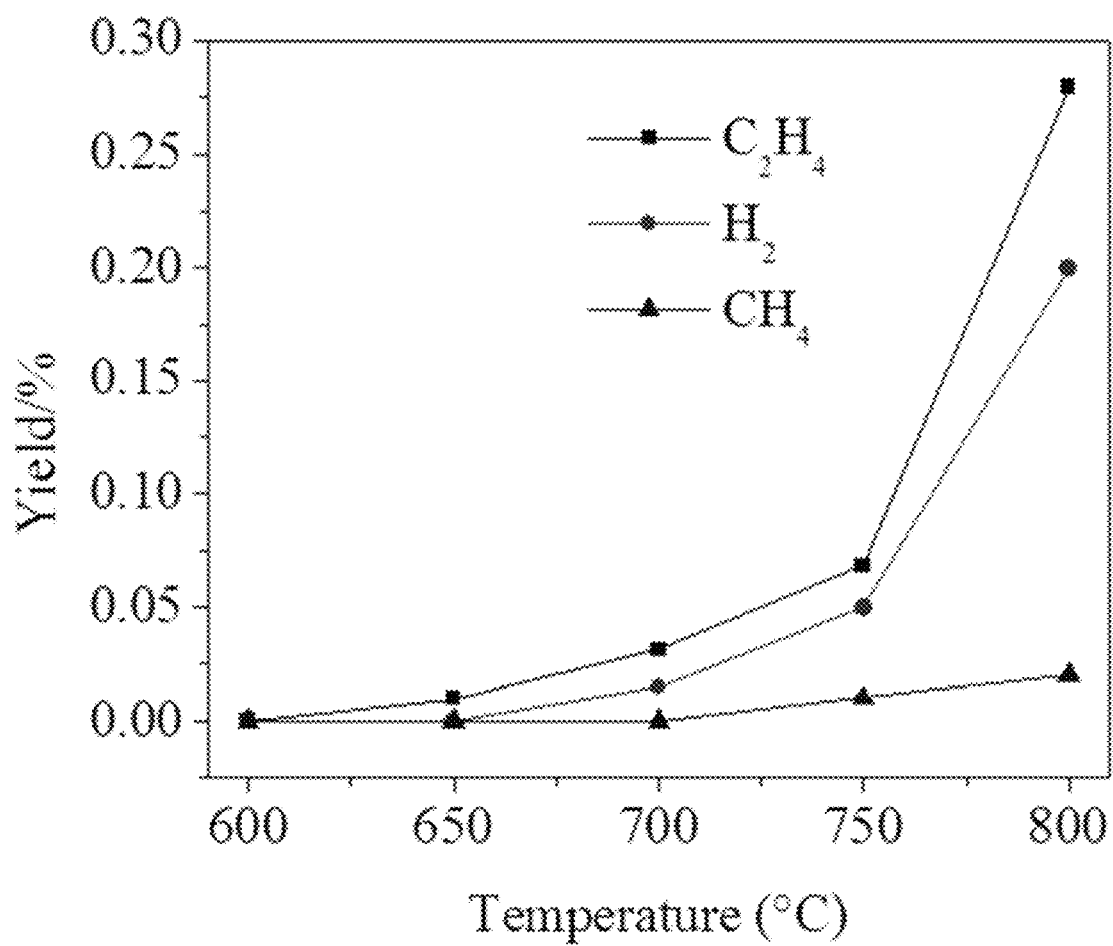
FIG. 4 shows $C_2H_4$, $H_2$ and $CH_4$ yield obtained from thermal conversion at different temperatures.

The primary function of the proposed redox catalysts is to selectively oxidize ethane into ethylene and water in absence of gaseous oxygen. Since ethylene can also be formed via thermal cracking of ethane at high temperature, the reaction temperature in this work is limited to 700° C. Blank experiments indicate that thermal ethane conversion is less than 5% at this temperature. Blank experiments are conducted by flowing 37.5% ethane (40 ml·min$^{-1}$, balance Ar) into U-tube loaded with inert aluminum oxide. Product distributions are obtained at 5 different temperatures: 600, 650, 700, 750 and 800° C. FIG. 4 shows the yield of each species at such temperature. We observe that $CH_4$ formation is insignificant at all temperatures. Above 700° C., we see a dramatic increase in $C_2H_4$ and $H_2$ from thermal cracking.

Figure 5A:
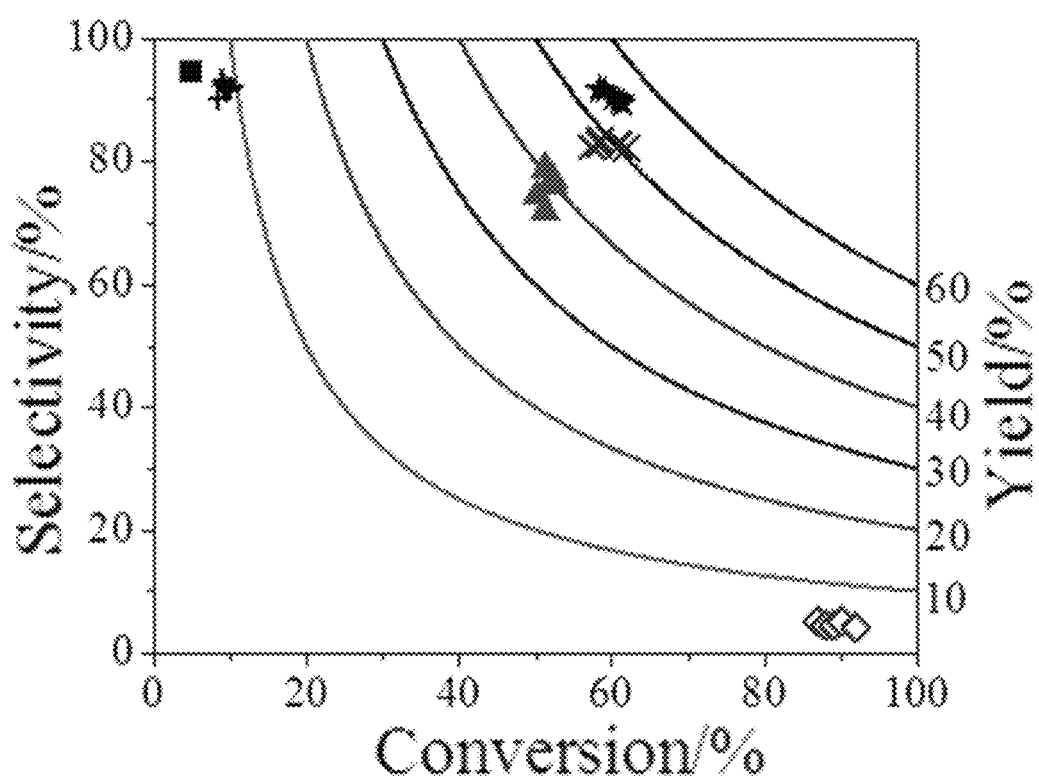
FIGS. 5A-5B show (FIG. 5A) selectivity/conversion/yield of (◊) pure LSF (✤) $0.1LiFeO_2$-LSF (x) $LiFeO_2$-LSF (★) $2.5LiFeO_2$-LSF (+) $LiFeO_2/MgAl_2O_4$ (■) blank experiment obtained in five redox cycles, and (FIG. 5B) gas product profile in a transient pulse on $LiFeO_2$-LSF: Temperature=700° C.; Space velocity=3000 $h^{-1}$.
Figure 5B:
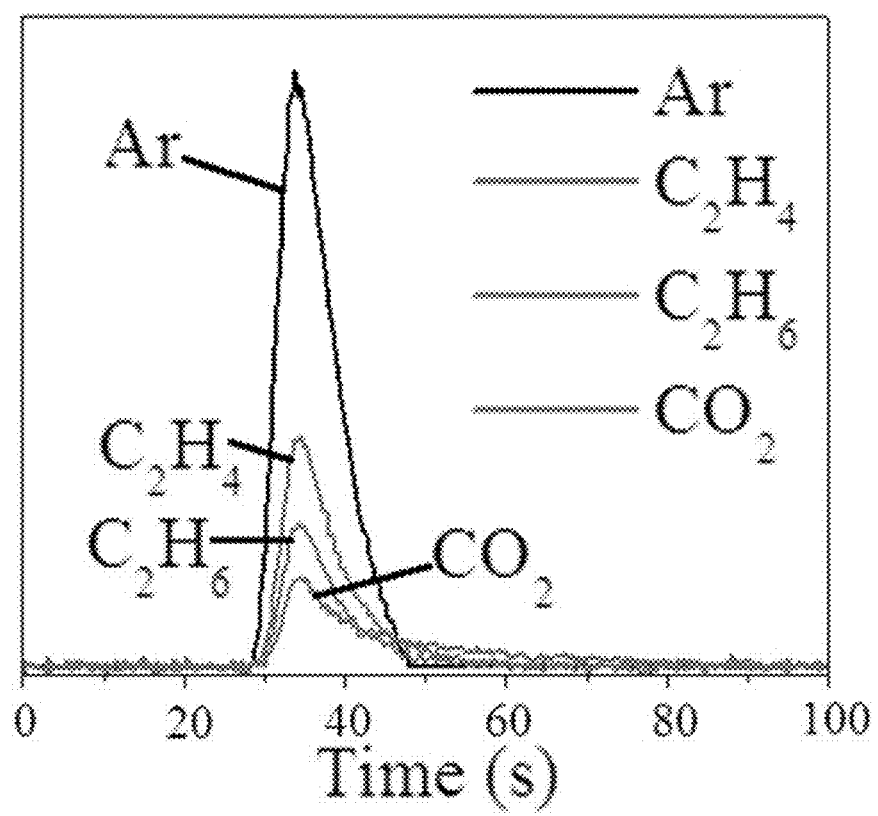

The proposed redox ODH concept relies on active lattice oxygen in the redox catalyst. For the current $LiFeO_2$-LSF system, active lattice oxygen is primarily provided by a B-site deficient LSF phase, which has limited oxygen capacity. This, coupled with the relatively high activity of the redox catalyst, make the redox ODH reaction highly dynamic, i.e. ethane conversion and ethylene selectivity quickly change as active lattice oxygen gets consumed. In order to accurately characterize the redox behavior of the redox catalyst, a transient pulse analysis is performed since it is shown to be particularly effective to characterize reducible oxides.[36,37,38] In such experiments, the amount of ethane in each pulse is small enough such that changes in the bulk and surface properties of the redox catalyst is minimal between consecutive pulses. FIG. 5A shows the reactivity data for LSF with different Li loadings. For comparison purposes, the abovementioned values are also determined for a blank tube, pure LSF, and an inert ($MgAl_2O_4$) supported $LiFeO_2$ under identical conditions. In that figure, we included five discrete dots for each dot shape/color. Each type of dots stands for a distinct redox catalyst and the five dots represent 5 pulses with regenerations. These dots fall into the same region, indicating a stable catalyst regenerability. Blank experiment shows insignificant thermal conversion of ethane at 700° C. (less than 5%) albeit at a high selectivity. In contrast, approximately 95% conversion is achieved with LSF but selectivity towards ethylene is less than 10%, with $CO_2$ being the primary product. This indicates that unpromoted LSF is effective for ethane combustion. In comparison, the Li promoter significantly changes the activity and selectivity of the redox catalysts. Merely 1.42 w.t. % Li promoting in LSF (0.1$LiFeO_2$-LSF) shifts the ethylene selectivity from less than 10% to over 60%. Meanwhile, ethane conversion decreases from 95% to 50-60%. With increasing amounts of Li promoter (from 0.1 $LiFeO_2$-LSF to 2.5$LiFeO_2$-LSF), the selectivity increases from ca. 70% to ca. 90%. The highest ethylene yield (55%) is obtained on 2.5$LiFeO_2$-LSF. Comparable selectivity can also be achieved with $MgAl_2O_4$-supported $LiFeO_2$. However, the conversion is low (12%), which can be explained by the low oxygen carrying capacity and activity of $LiFeO_2$. A typical gas product profile in a transient pulse on $LiFeO_2$-LSF is shown in FIG. 5B. Ethylene, $CO_2$ and unreacted ethane are the main product components with Ar being the dilution gas. At 700° C., the amount of hydrogen formed in all the experiments are negligible based on quadruple mass spectrometer and GC measurements. This indicates close to 100% selectivity towards $H_2O$. A high $H_2O$ selectivity is desired since the effective combustion of $H_2$ in the ODH step results in increased heat release from regeneration and contributes to overall heat balance of the proposed CL-ODH process.[35]

Figure 6:
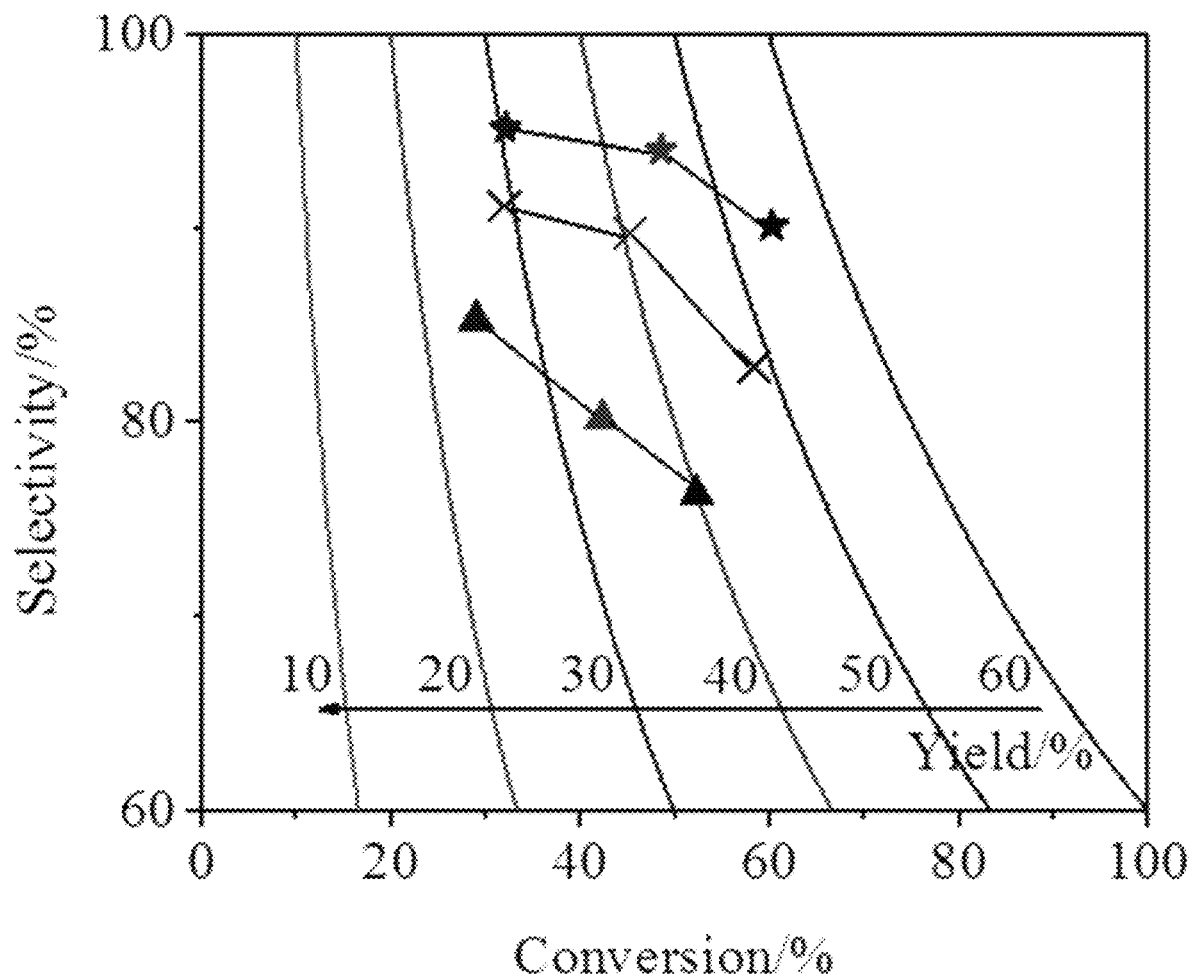
FIG. 6 shows selectivity/conversion/yield of (▲) $0.1LiFeO_2$-LSF (x) $LiFeO_2$-LSF ★) $2.5LiFeO_2$-LSF at 700° C., 675° C. and 650° C.: Space velocity=3000 $h^{-1}$

Temperature effects are investigated for all Li promoted redox catalysts. FIG. 6 shows the catalytic performances of redox catalysts at three different temperatures (650° C., 675° C. and 700° C.). It is observed that the selectivity slightly increases with decreasing temperatures but the corresponding conversion drops more significantly. This indicates that the activity and selectivity of oxygen species in the redox catalysts are highly temperature dependent. At higher temperatures, more lattice oxygen is transported to the redox catalyst surface at higher rates. This leads to increased active oxygen species on the redox catalyst surface for higher ethane conversion. We note that the abundance of oxygen on the surface can lead to increased non-selective surface oxygen species via oxygen evolution ($O^{2-} \rightarrow O^- \rightarrow O_2^{2-} \rightarrow O_2^-$), this can cause deep oxidation as reported by Neal and Shafiefarhood et al. for $Fe_2O_3$@LSF based redox catalysts in methane conversion.[26,36] The effects of oxygen type on redox catalyst selectivity is further discussed in later sections. Higher reaction temperatures are not studied in the current manuscript due to increased thermal cracking at higher temperatures (~15% ethane conversion at 750° C.).

Figure 7:
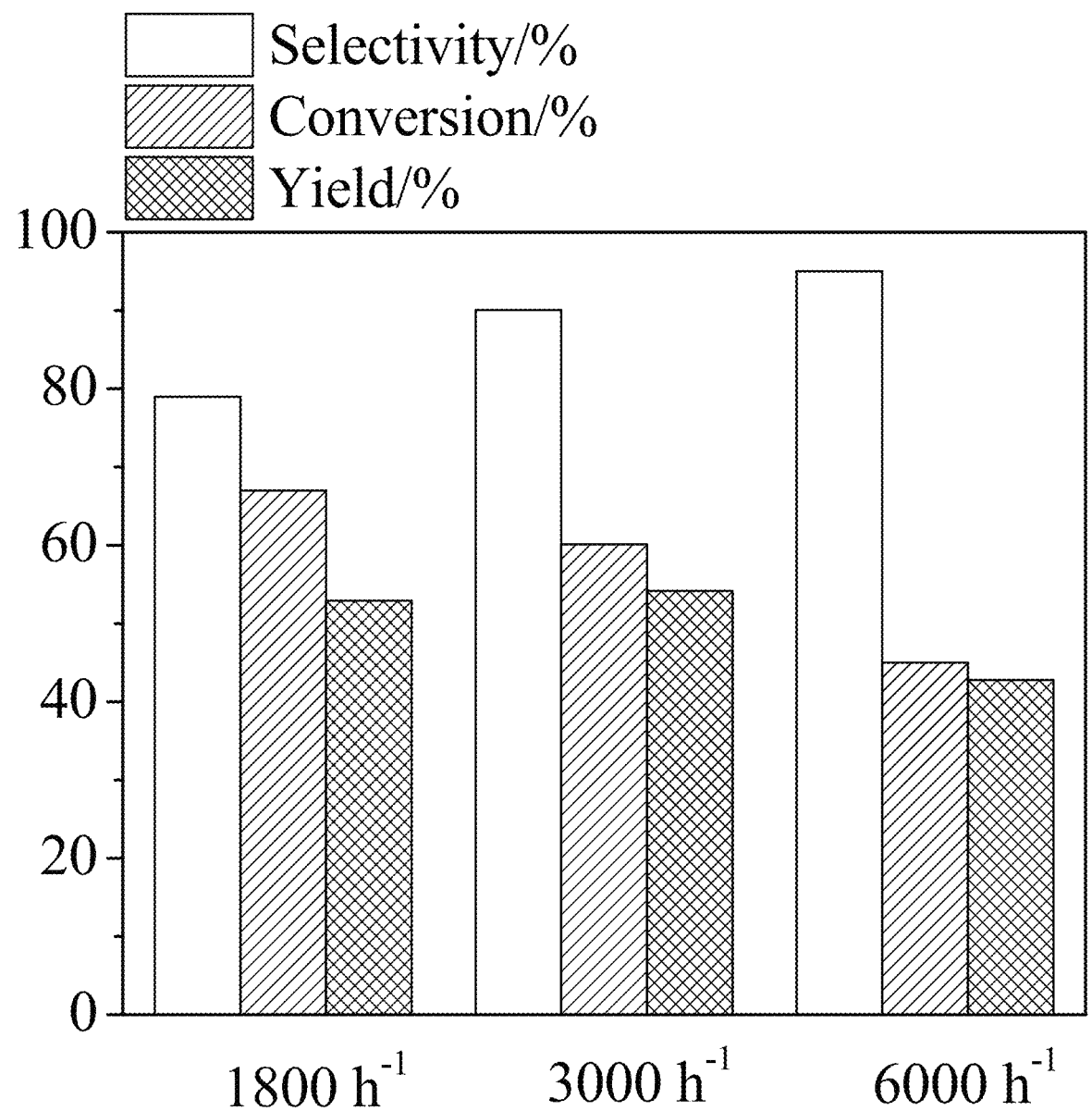
FIG. 7 shows selectivity/conversion/yield obtained on $2.5LiFeO_2$-LSF with different space velocities: Temperature=700° C.

Besides temperature, the effect of space velocity is also studied by varying the gas flow rate. FIG. 7 shows the catalytic performance with different space velocities on 2.5$LiFeO_2$-LSF. As anticipated, a higher conversion can be obtained at a lower space velocity with a decrease in selectivity. The change in conversion/selectivity can be explained by increasing electrophilic oxygen species and readsorption of ethylene species on redox catalyst surface at lower space velocities. The highest ethylene yield is observed at a space velocity of 3000 h$^{-1}$. Such a space velocity is used in most of the reactivity tests.

Figure 8A:
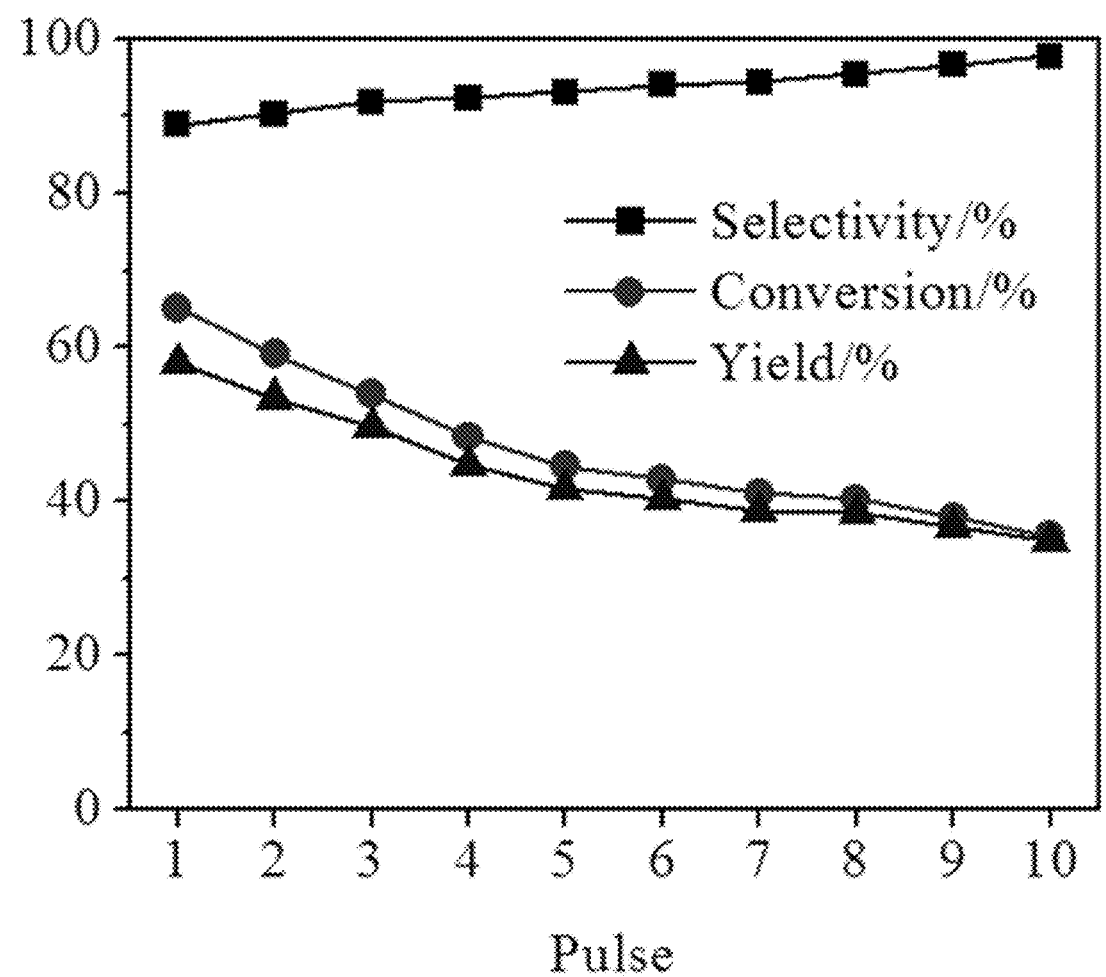
FIGS. 8A-8B show (FIG. 8A) selectivity/conversion/yield on $2.5LiFeO_2$-LSF from consecutive pulse 1 to 10 without regeneration, and (FIG. 8B) cumulative selectivity/conversion/yield for Li promoted LSF in the first 10 pulses: Temperature=700° C.; Space velocity=3000 $h^{-1}$
Figure 8B:
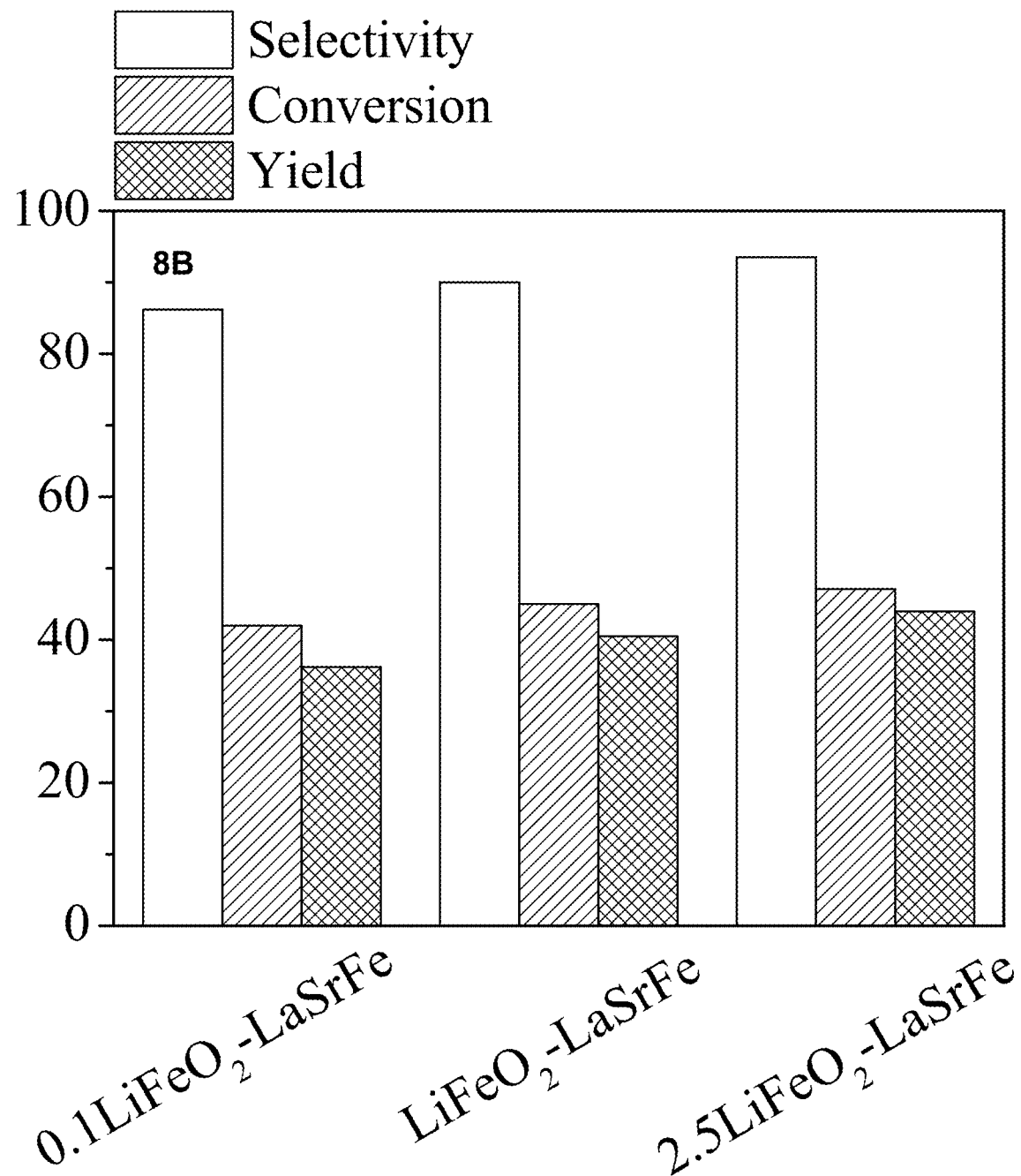

In order to investigate the dynamic conversion/selectivity trend with the consumption of active lattice oxygen, 10 consecutive ethane pulses without regeneration are introduced onto 2.5$LiFeO_2$-LSF (FIG. 8A). With increasing number of pulses, the selectivity gradually increases and conversion decreases. This is consistent with the loss of active lattice oxygen over multiple redox cycles. Overall ethylene yields remain above 35% in all 10 pulses. FIG. 8B shows the average selectivity/conversion/yield obtained within the first 10 pulses for each Li promoted sample. Similar to the results for the first pulse (FIGS. 5A-5B), 2.5$LiFeO_2$-LSF is the best-performing redox catalyst, with an average selectivity of 94% and average yield of 44%.

Figure 9:
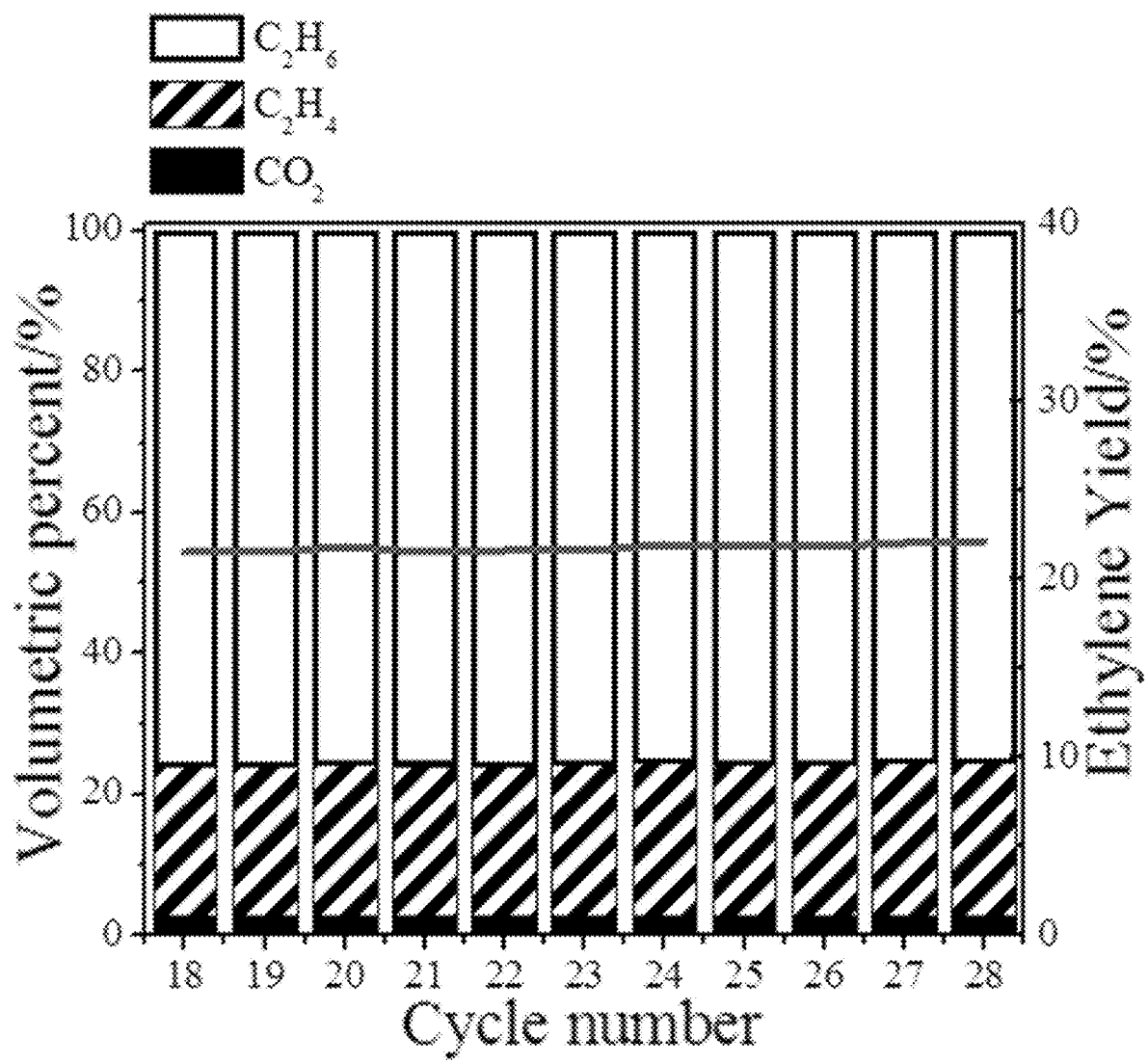
FIG. 9 shows product species distributions and ethylene yields obtained on $LiFeO_2$-LSF. Cycle number from 18 to 28. Temperature=700° C.
Figure 10:
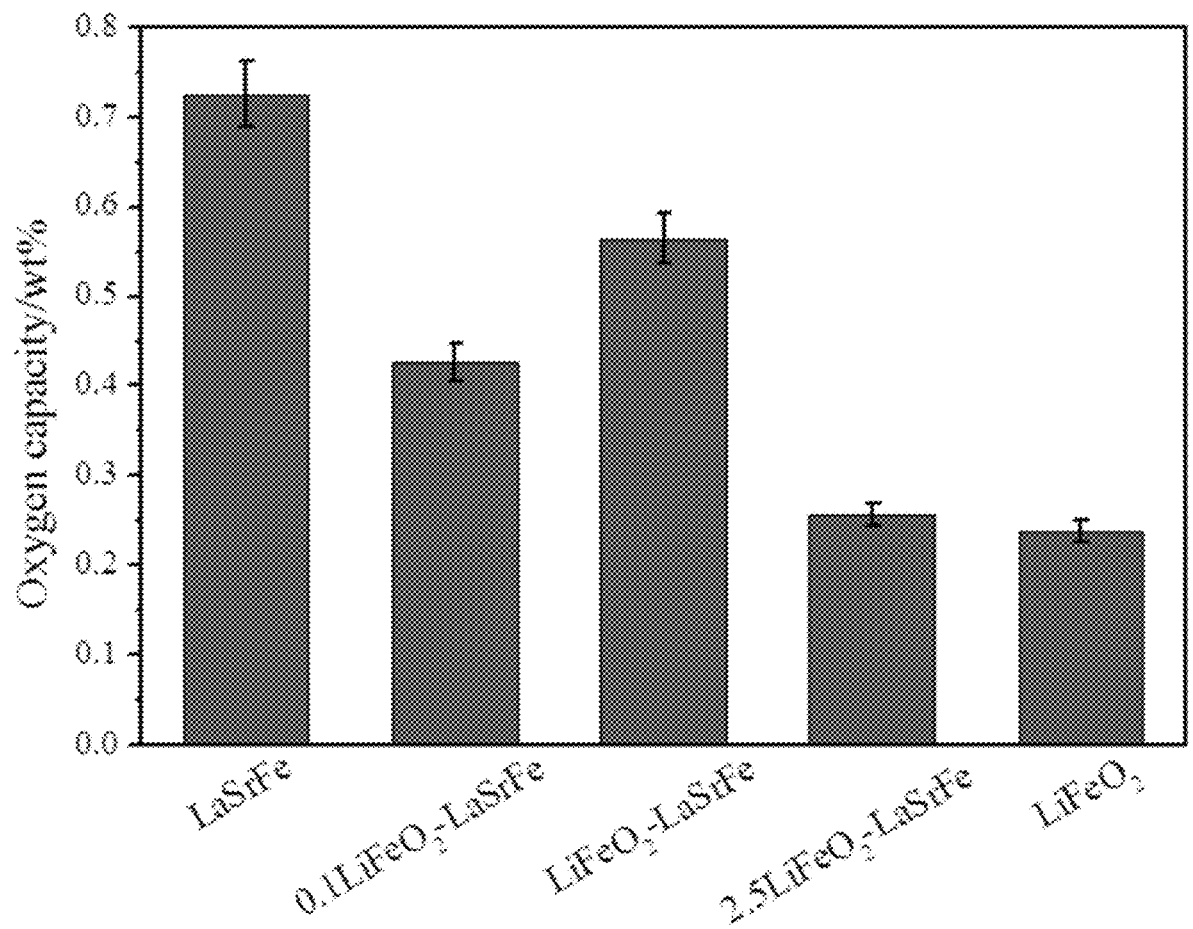
FIG. 10 shows oxygen capacity of pure LSF, 0.1LiFeO2-LSF, LiFeO2-LSF, 2.5LiFeO2-LSF and LiFeO$_2$ at 700° C. Error bars indicate 95% confidence interval from 8 redox cycles.

Oxygen carrying capacity of a redox catalyst is crucial for all cyclic redox processes. The oxygen capacity can be calculated using an oxygen mass balance. Eight redox cycles are repeated to confirm the reproducibility of the calculated oxygen capacity. Negligible change in redox catalyst performance is observed in terms of ethane conversion, ethylene selectivity, and oxygen carrying capacity. FIG. 10 shows the oxygen capacity with each redox catalyst, including pure LSF and $LiFeO_2$. The oxygen capacity of $LiFeO_2$ is obtained on $LiFeO_2$/$MgAl_2O_4$ and normalized to the amount of pure $LiFeO_2$. As shown in the figure, the oxygen capacity decreases from 0.73 w.t. % to 0.26 w.t. % with the increasing of Li promoter amount. It can be explained by the low oxygen carrying capacity of $LiFeO_2$ (0.24 w.t. %). This indicates that the oxygen capacity in Li promoted LSF is mostly contributed by the LSF phase. We note that redox catalyst with 1:1 molar ratio of $LiFeO_2$ and LSF exhibits significantly higher oxygen carrying capacity than the redox catalysts with 1:10 ratio of $LiFeO_2$ and LSF. This may be due to a phase cooperation effect between LSF and $LiFeO_2$ phases. A similar phase cooperation mechanism was also proposed by Ozkan et al. on the basis of contact synergy mechanism.[39] It is noted that the oxygen carrying capacity of the LSF containing redox catalysts are in line with that for $CaMnO_3$ based oxygen carriers for chemical looping with oxygen uncoupling.[40] Such an oxygen carrying capacity range, although relatively low, is practical for the proposed redox operations. The stability of the redox catalysts is further confirmed with 30 redox cycles on $LiFeO_2$-LSF as a model redox catalyst, which shows stable product distributions and ethylene yields (FIG. 9). The stability of the redox catalysts are further confirmed by running 30 redox cycles on $LiFeO_2$-LSF as a model redox catalyst. The redox cycles are in continuous flow mode, with feed conditions identical to those discussed in experimental section. FIG. 9 shows the cumulative product species distributions and ethylene yield within the first 30 seconds of each reduction step. The redox catalyst performance is stable within 30 cycles.

Figure 11A:
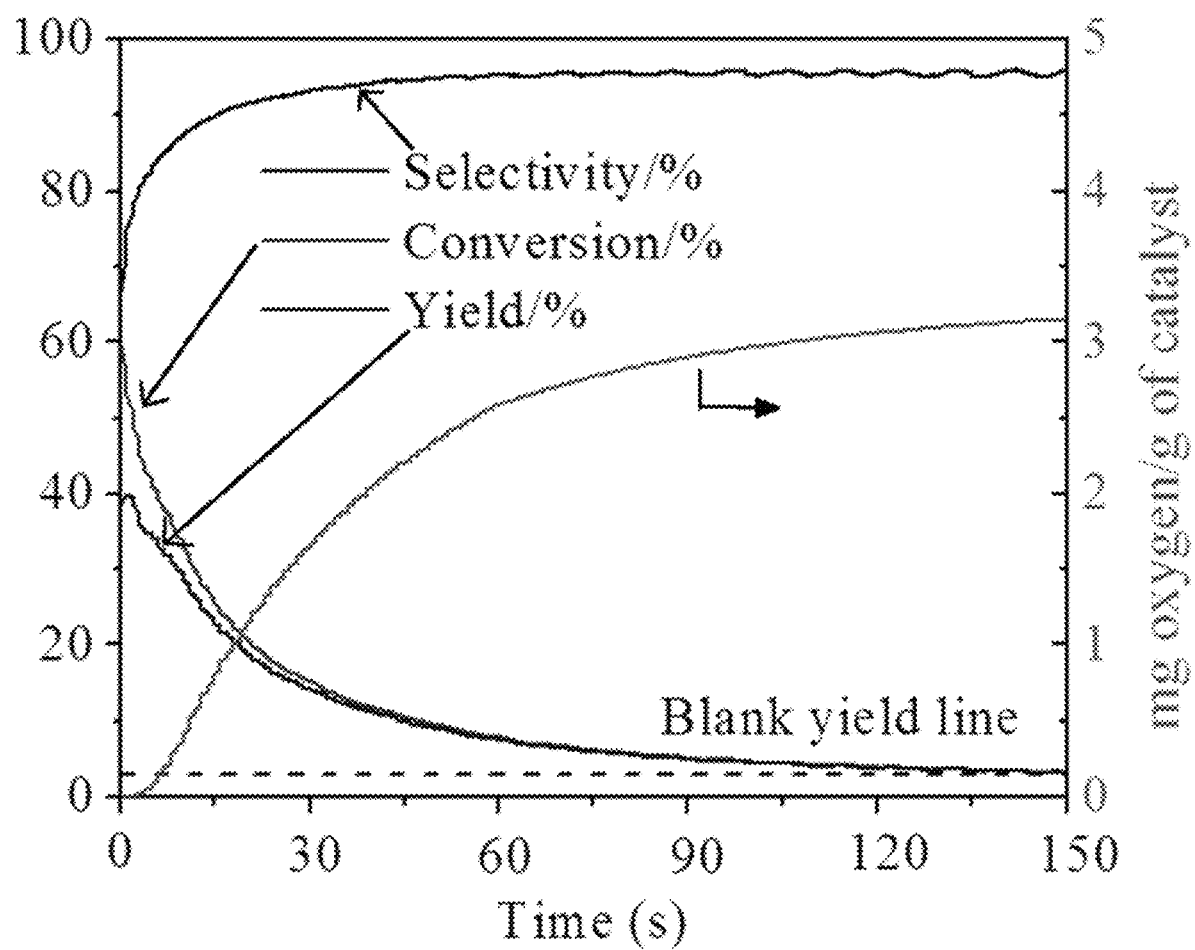
FIGS. 11A-11B show (FIG. 11A) instantaneous selectivity/conversion/yield (Left Y-axis) and cumulative oxygen release (Right Y-axis) obtained and (FIG. 11B) cumulative selectivity/conversion/yield obtained on 2.5LiFeO$_2$-LSF as a function of time: Temperature=700° C.; Cycle number=8.
Figure 11B:
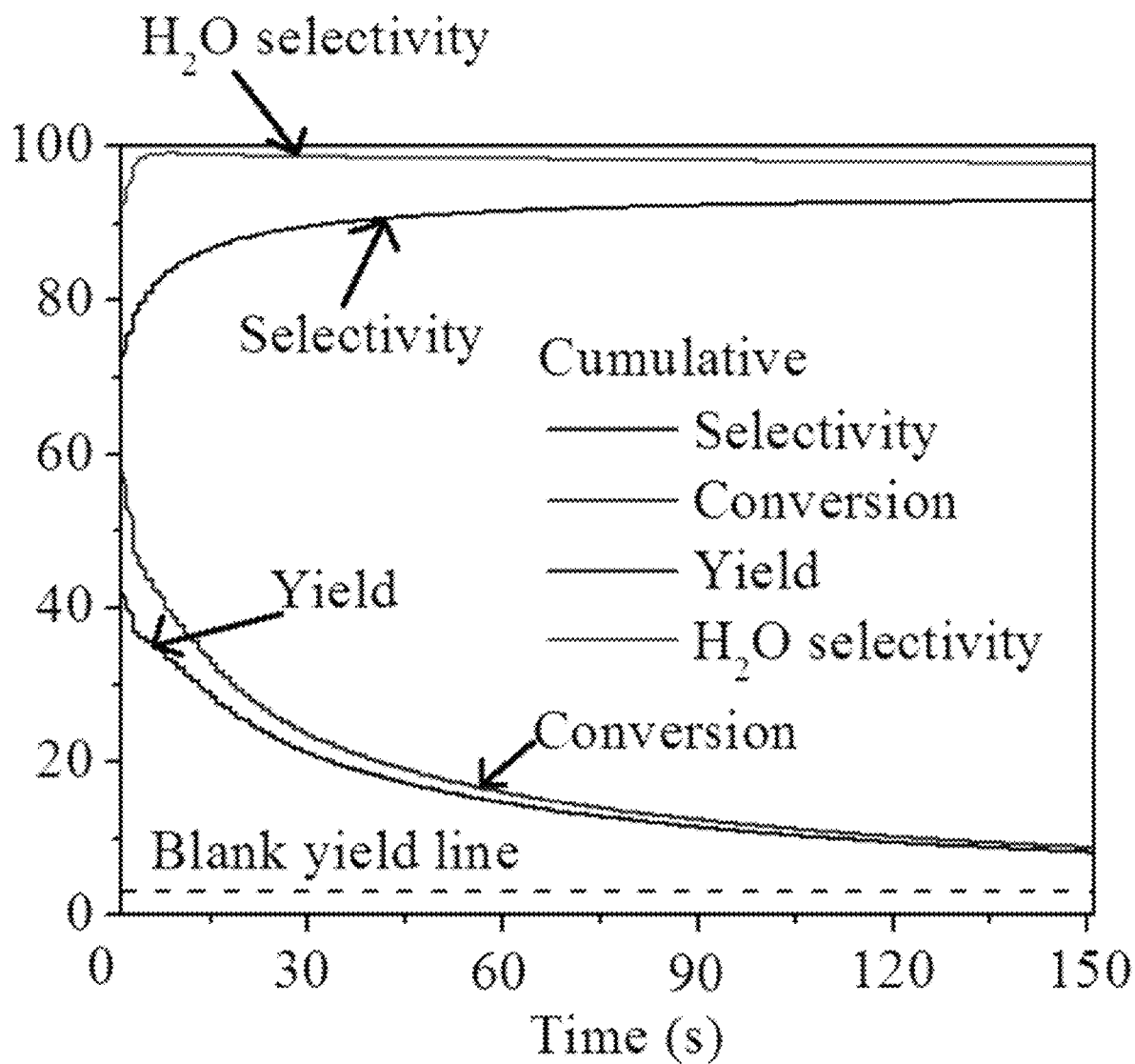

To further investigate the ODH performance of the redox catalysts, 37.5% ethane (40 ml·$min^{-1}$, balance Ar) is used as reducing gas to react with a fixed bed of redox catalysts for a 3 min reduction half-cycle. FIG. 11A illustrates the 2.5$LiFeO_2$-LSF redox catalyst's selectivity/conversion/yield and cumulative oxygen release as a function of reduction time. The dashed line stands for blank yield at 700° C., which represents the background thermal conversion of ethane. As can be seen, selectivity increases from around 70% and remains constant around 90%. Conversion and yield decrease with the consumption of active lattice oxygen and reach the blank yield line at the end of the reduction step. In a practical operation, the redox catalyst residence time can be limited to the first 10, 20 or 30 seconds, which can give cumulative selectivity/conversion/yield of 84.7%/38.3%/32.4%, 88.1%/29.1%/25.6% and 89.7%/23.7%/21.2%, respectively. We note that 70 w.t. % of the available oxygen is released within the first 30 seconds, which indicates fast oxygen release kinetics. FIG. 11B shows the cumulative selectivity/conversion/yield as a function of time. Also, slightly lower ethylene selectivity is observed at the beginning of the reduction half-cycle. A similar phenomenon has been reported by Neal and Shafiefarhood et al.,[26,36] which indicates that the redox catalyst surface contains high concentration of electrophilic oxygen species that accounted for deep oxidation. It is noted that the calculated cumulative $H_2O$ selectivity is close to 100% during the reduction step. This indicates that the redox catalyst is very effective for selectively combusting $H_2$ into $H_2O$.

Redox Catalyst Characterizations

Figure 12:
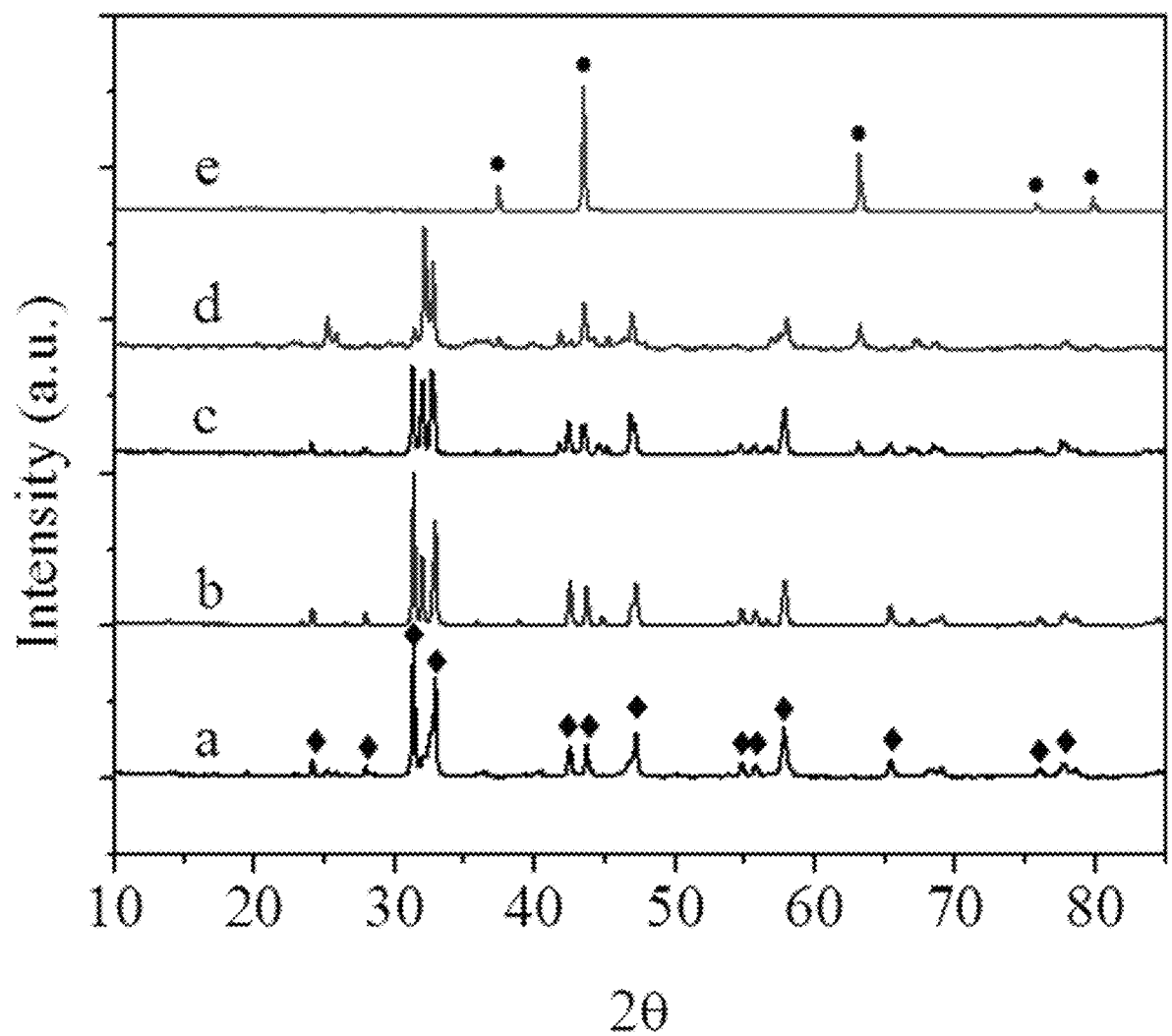
FIG. 12 shows XRD pattern of as-prepared (a) La$_{0.6}$Sr$_{1.4}$FeO$_4$ (b) 0.1LiFeO$_2$-LSF (c) LiFeO$_2$-LSF (d) 2.5LiFeO$_2$-LSF (e) LiFeO$_2$. ●: LiFeO$_2$; ▲: La$_{0.6}$Sr$_{1.4}$FeO$_4$.

In order to further understand the role of Li and corresponding ODH reaction pathways, the redox catalysts are investigated using a number of characterization tools. FIG. 12 illustrates the XRD patterns for all the as-prepared samples. As can be seen, all the Li promoted samples exhibit two crystalline phases, i.e. a B-site deficient perovskite (Ruddlesden-Popper, $La_xSr_{2-x}FeO_{4-\delta}$) phase and a $LiFeO_2$ phase (disordered cubic rocksalt, ICDD PDF #: 00-002-1237). The formation of $LiFeO_2$ and B-site deficient perovskite phases are likely to be due to Li binding with Fe cations within the pristine $La_xSr_{1-x}FeO_3$ phase. For comparison purpose, pure $La_{0.6}Sr_{1.4}FeO_4$ (LSF) and pure a-$LiFeO_2$ samples are also included in this study. The main perovskite phase in $LiFeO_2$-LSF and 0.1$LiFeO_2$-LSF is identified to be $La_{0.6}Sr_{1.4}FeO_4$ (ICDD PDF #: 01-072-7578). This is further confirmed by comparing with the X-ray diffraction pattern with a reference $La_{0.6}Sr_{1.4}FeO_4$ sample. In the case of 2.5$LiFeO_2$-LSF, $LaSr_3Fe_3O_{9.88}$ is determined as the main crystalline phase (ICDD PDF #: 04-007-9523). The formation of a $LaSr_3Fe_3O_{9.88}$ phase may be due to a crystalline distortion of $La_{0.6}Sr_{1.4}FeO_4$ structure.[41] We note that the XRD pattern of $LaSr_3Fe_3O_{9.88}$ shares similar peak positions and relative intensities of the $La_{0.6}Sr_{1.4}FeO_4$ phase. A new peak between 30 and 35 degree forms in the case of $LiFeO_2$-LSF and 0.1$LiFeO_2$-LSF. This new peak can be assigned to a minor strontium ferrite ($SrFeO_3$) phase. The formation of this relatively stable phase is likely to result from the high Sr: La ratio used in the current study. A similar effect was reported by Neal et al.[42] To conclude, the Li promoted LSF sample is characterized to be a composite of $LiFeO_2$ and an Fe-deficient LSF phase. Surface area analyses using BET are also conducted, which shows comparable low surface areas within the range of 1-6 $m^2/g$ for all the as-prepared samples (Table 1).

TABLE 1

BET surface areas for calcined pure LSF, 0.1LiFeO2-LSF, LiFeO2-LSF and 2.5LiFeO2-LSF

| | Pure LSF | 0.1$LiFeO_2$-LSF | $LiFeO_2$-LSF | 2.5$LiFeO_2$-LSF |
|---|---|---|---|---|
| BET surface area ($m^2/g$) | 4.377 | 1.095 | 2.709 | 5.576 |

Figure 13:
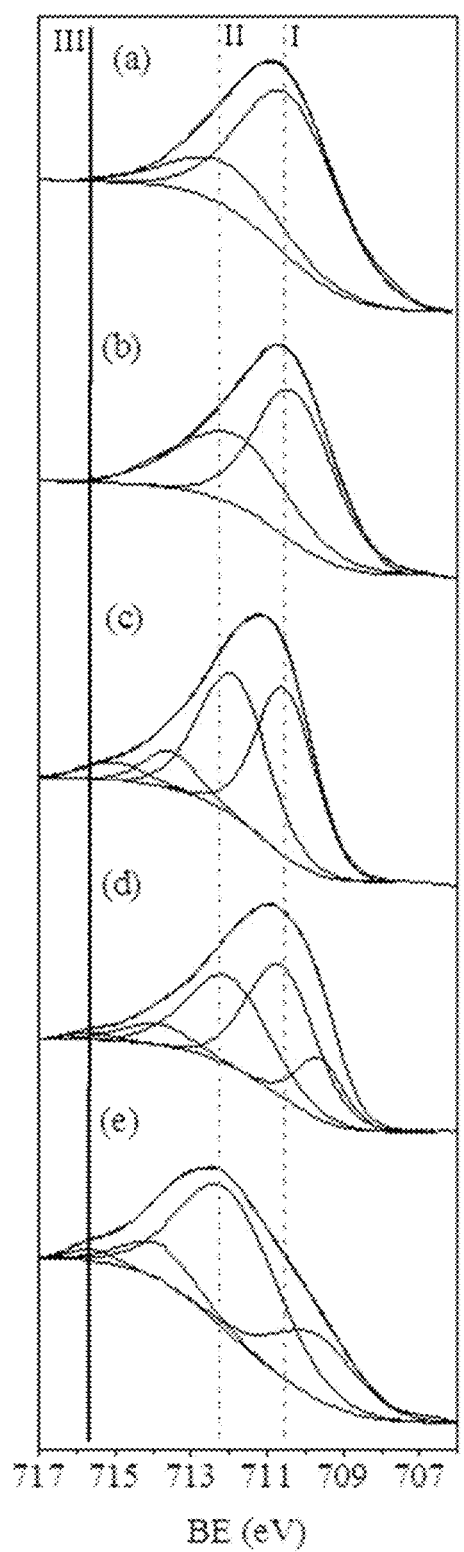
FIG. 13 shows detailed Fe 2p 3/2 XPS scans for (a) LiFeO$_2$, (b) 2.5LiFeO$_2$-LSF, (c) LiFeO$_2$-LSF, (d) 0.1LiFeO$_2$-LSF and (e) LSF. Arbitrary dashed lines (I and II) for major peaks characteristic of LiFeO$_2$. Arbitrary solid line (III) for high B.E. shoulder peak characteristic of LSF.
Figure 14A:
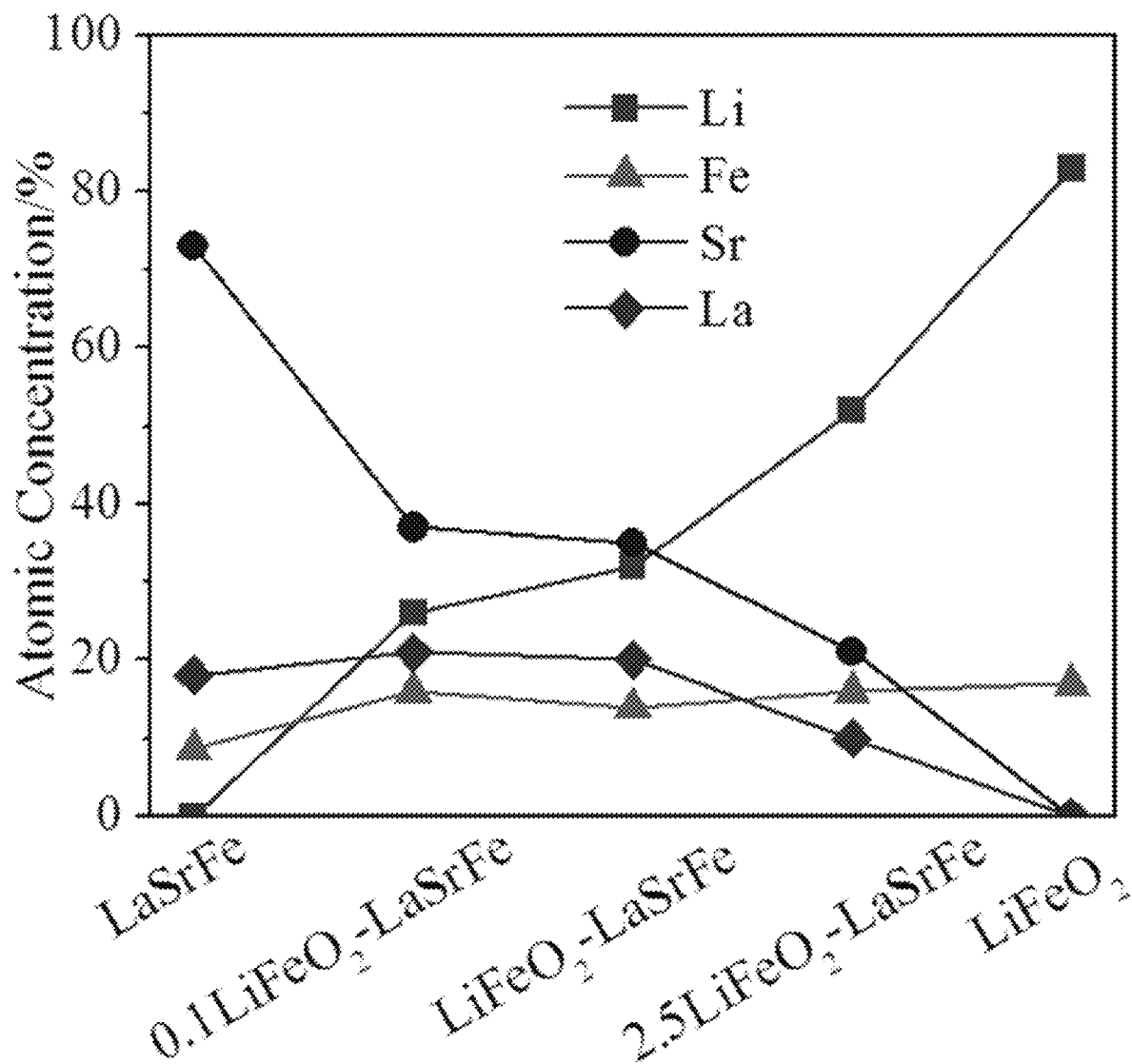
FIGS. 14A-14C show near surface cation concentrations for (FIG. 14A) as-prepared and (FIG. 14B) cycled redox catalysts, and (FIG. 14C) ratios between surface Li concentration relative to bulk cation concentration for cycled 0.1LiFeO$_2$-LSF, LiFeO$_2$-LSF and 2.5LiFeO$_2$-LSF. Dashed line for ratio of 1.
Figure 14B:
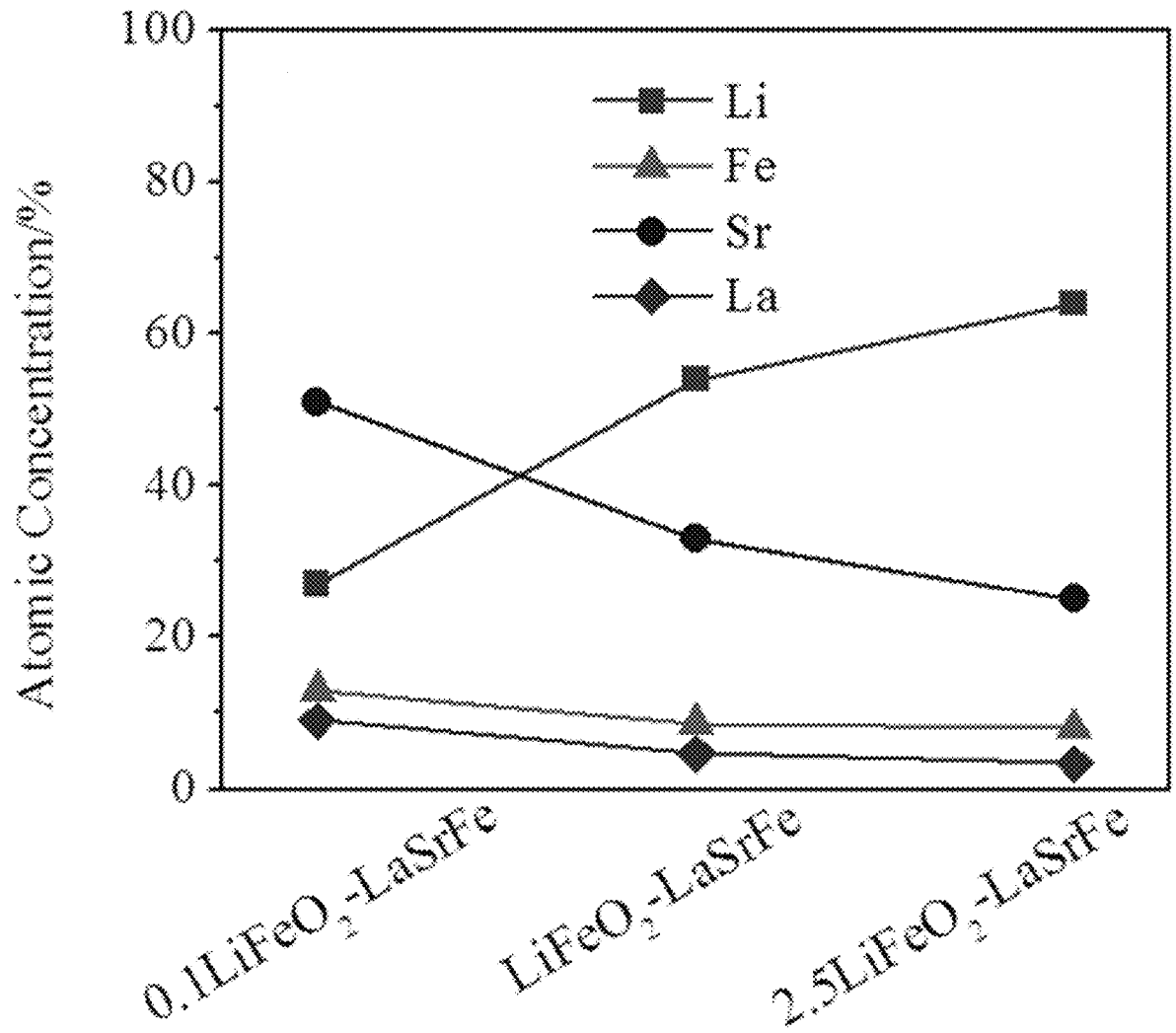

Even though bulk lattice oxygen is a crucial reactant, the ODH reaction occurs on the redox catalyst surface.[29] It is therefore important to investigate the surface properties of the redox catalysts in addition to their bulk structural properties. FIG. 14A shows the near surface cation compositions of the as-prepared redox catalysts as determined by XPS. All concentrations are presented in atomic concentrations and are reported in two significant digits. Pure $LiFeO_2$ is also examined as a reference. Consistent with previous reports on the LSF system[26,42], the surface of LSF shows significant Sr enrichment (73% of cations). Addition of even small amount of lithium, e.g. 0.1$LiFeO_2$-LSF, decreases surface Sr concentration to ~40% with little to no decrease in Fe and La cation concentrations. Such drop in Sr concentration is due to the enrichment of Li on the surface. Near surface Li concentration becomes more pronounced with higher amount of Li addition: Li becomes the largest near surface component on 2.5$LiFeO_2$-LSF (52% of cations) while Sr drops to 21%. Fe and La cation concentration remain similar in all Li promoted redox catalysts except in 2.5$LiFeO_2$-LSF where Fe is slightly higher than La. We note that Fe concentration does not drop much with Li promotion and even increases for 2.5 $LiFeO_2$-LSF sample. This inconsistency with $Li_2O$ enrichment may be attributed to the coexistence of $LiFeO_2$ phase on the surface. It is supported by comparing the detailed Fe $2p_{3/2}$ XPS scan of redox catalysts. The Fe spectra in $LiFeO_2$ is consistent with 2.5$LiFeO_2$-LSF but differs much from LSF (FIG. 13). The coexistence of $LiFeO_2$ with $Li_2O$ on Li promoted LSF surface is confirmed by detailed Fe $2p_{3/2}$ XPS scans. As is shown in FIG. 13, two major peaks are identified on $LiFeO_2$, a lower binding energy (B.E.) peak at 710.4 eV and a higher B.E. peak at 712.1 eV. These characteristic peaks are entirely consistent with 2.5$LiFeO_2$-LSF, indicating that the Fe species in 2.5$LiFeO_2$-LSF are in the form of $LiFeO_2$. Additional peaks show up with lower amount of Li promotor. These additional peaks are characteristic of LSF. We note that a high B.E. shoulder peak around 715 eV to 716 eV exists for LSF, 0.1LiFeO2-LSF and LiFeO2-LSF. Such shoulder peak has been identified as surface low-coordinated Fe species.[1]

In our case, this shoulder peak is characteristic of B-site deficient LSF. These results indicate the LSF surface is gradually covered by $Li_2O$ and $LiFeO_2$ as the amount of Li promotor increases.

Figure 14C:
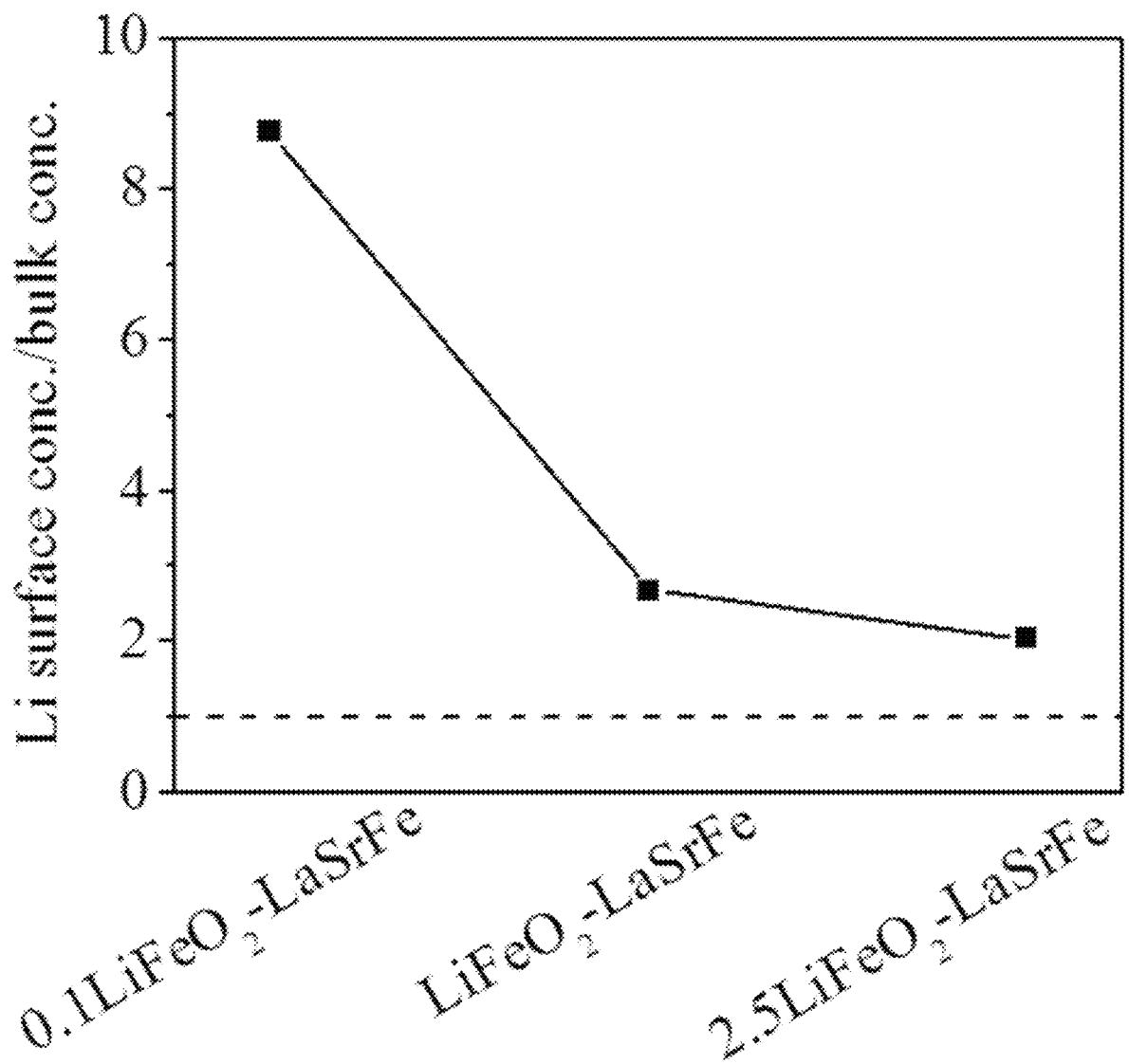

Similar concentration changes are also observed on cycled redox catalysts (after 8 cycles, ending in oxidation) and the near surface lithium concentrations are slightly higher than as-prepared samples. Since redox reactions promotes ionic diffusions[43], further enrichments of Li on the surface after redox cycles indicate that Li cation enrichment reduces surface energy of the redox catalysts. The degree of Li surface enrichment can also be quantified by calculating the near surface Li concentration to bulk concentration ratio. The bulk lithium concentration can be estimated by assuming the redox catalysts to be a homogeneous mixture of $LiFeO_2$ and LSF. Based on the ratio between measured surface concentration and bulk concentration, a surface elemental enrichment (ratio>1) or deficiency (ratio<1) can be obtained. From FIG. 14C, a significant surface enrichment of lithium can be observed on all cycled Li promoted redox catalysts. In fact, near surface Li content is overestimated by as much as 770% for $0.1LiFeO_2$-LSF, showing that Li cation is selectively enriched on the surface. Although surface termination by a Li layer could contribute to Li cation enrichment, it cannot explain the degree of enrichment observed since XPS detects the first several nanometers of the sample.[44] One possible explanation is that the redox catalyst surface is covered with a $Li_2O$ and/or $LiFeO_2$ layer, which is too thin to be detectable by XRD. TEM analysis as discussed later, is used to probe this possibility.

Figure 15:
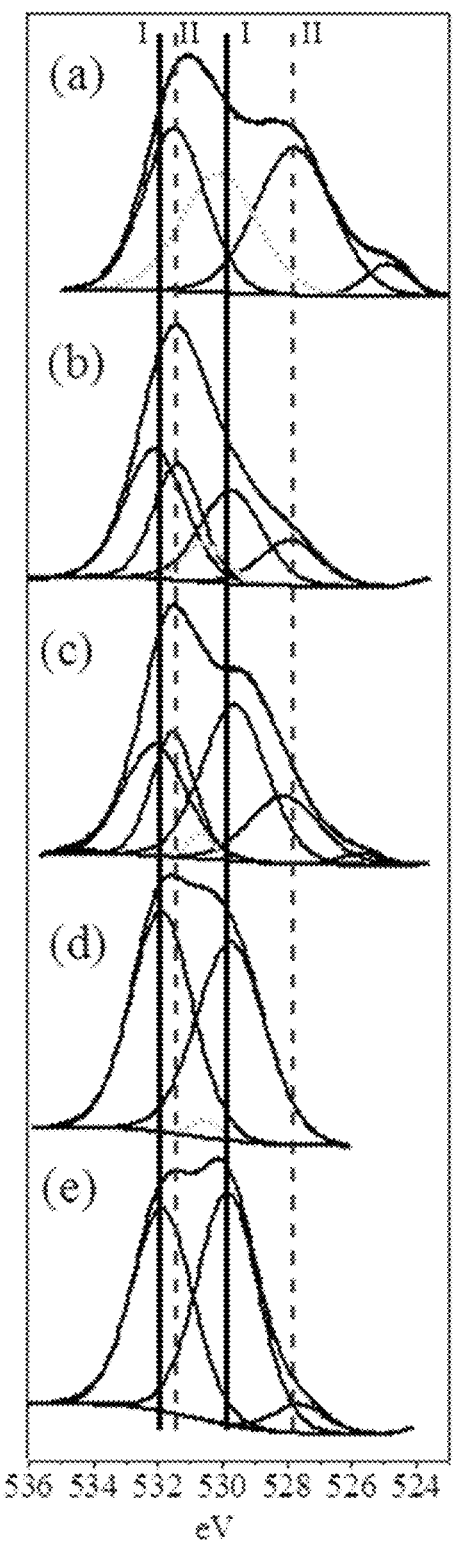
FIG. 15 shows detailed O 1s XPS scan for (a) LSF, (b) 0.1LiFeO$_2$-LSF, (c) LiFeO$_2$-LSF, (d) 2.5LiFeO$_2$-LSF and (e) LiFeO$_2$. Arbitrary solid lines (I) for major peaks characteristic of LiFeO$_2$. Arbitrary dashed lines (II) for major peaks characteristic of LSF. Dashed peaks for intermediate oxygen species.

The Li cation surface enrichment is further examined by detailed analysis of O 1s XPS spectra. FIG. 15 shows the O 1s profiles for as-prepared redox catalysts. Pure $LiFeO_2$ and pure LSF O 1s profiles are also examined as references. As can be seen, two major peaks and one minor peak are identified on $LiFeO_2$. The major peak located at 531.9 eV can be assigned to hydroxide and carbonate species and the other major peak at 529.8 eV can be ascribed to lattice oxygen in $Li_2O$.[45] The minor peak at around 528 eV is attributed to a minor oxygen deficient phase. LSF also shows two similar major peaks at different binding energies than in $LiFeO_2$. The major peak located at 531.5 eV can be assigned to hydroxide and carbonate species, and the peak at 527.8 eV can be assigned to lattice oxygen species from LSF. A minor, low binding energy peak is observable at 525 eV, which is characteristic of this B-site deficient LSF. Both sets of oxygen peaks from $LiFeO_2$ and LSF are visible in $LiFeO_2$-LSF and $0.1LiFeO_2$-LSF. Over half of the oxygen visible in the near surface region of $0.1LiFeO_2$-LSF is similar to those on the surface of $LiFeO_2$, consistent with the enrichment of Li identified from XPS. This indicates that the near surface oxygen species become similar to those in $LiFeO_2$ upon Li addition. This is consistent with the significant selectivity increase observed in $0.1LiFeO_2$-LSF redox catalyst. Higher Li concentration pushes the oxygen peaks closer to those identified in $LiFeO_2$. The major oxygen peaks identifiable on the $2.5LiFeO_2$-LSF are entirely consistent with $LiFeO_2$, which explains the highest selectivity obtained on this sample. As an additional evidence, deconvolution of the Fe 2p peaks leads to phase assignments entirely consistent with O 1s analysis (see supplemental FIG. 13), i.e. the surface compositions of Li promoted LSF are quite similar to those of $LiFeO_2$.

Besides the abovementioned characteristic peaks, the surface enrichment of Li cation has a strong effect on electrophilic surface oxygen species as indicated by the change in intermediate binding energy (B.E.) oxygen species on the redox catalysts. These intermediate B.E. oxygen species are located in the region of 530 eV to 531 eV and they are usually identified as electrophilic surface oxygen species.[46] Such oxygen species have been associated with deep oxidation.[47] On pure $LiFeO_2$, we do not observe this intermediate oxygen species peak. Such peak appears for LSF and but decreases with fraction of the $LiFeO_2$ phase. On pure LSF, the intermediate oxygen peak area is comparable to either of the major peaks. The suppression of such surface oxygen species can explain the increased selectivity for Li promoted redox catalysts.

Figure 16A:
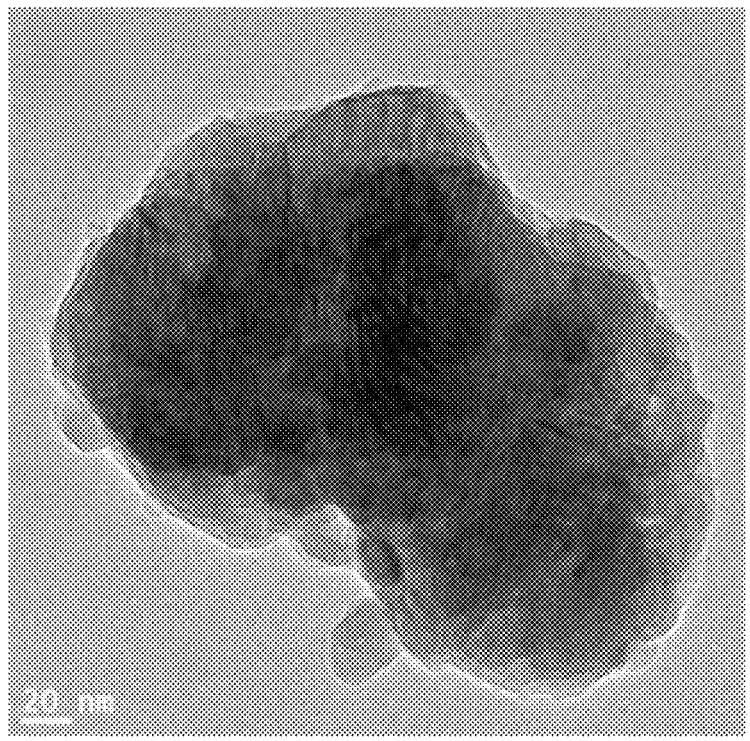
FIGS. 16A-16B show (FIG. 16A) TEM and (FIG. 16B) high resolution TEM micrograph on 2.5LiFeO$_2$-LSF. The effect of Li cation enriched surface on oxygen evolution.
Figure 16B:
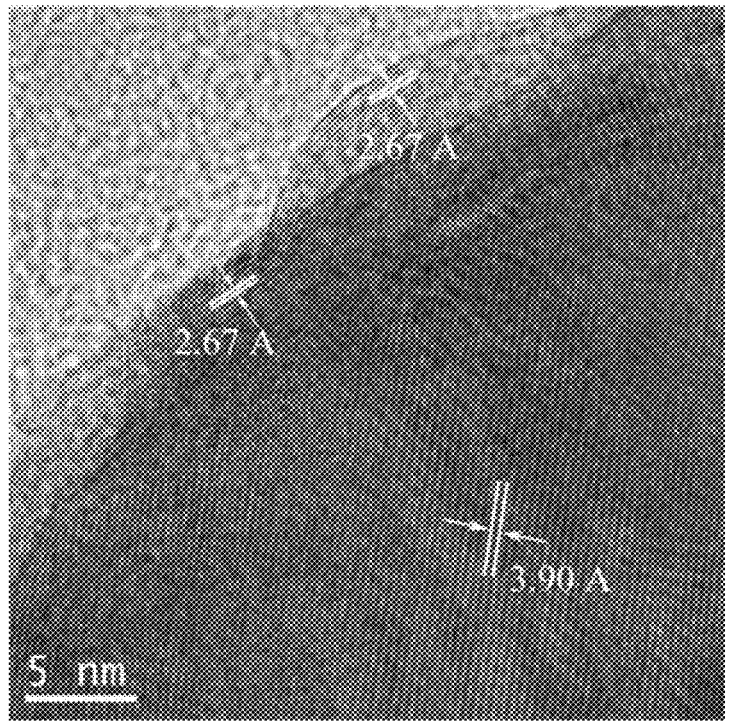

The LSF@$Li_2O$ core-shell structure is further characterized by a high resolution TEM. FIG. 16A shows a typical micrograph of $2.5LiFeO_2$-LSF. A particle size with approximately 100 nm diameter is observed. Higher magnification micrograph further verifies the enrichment of Li cation on the surface. As shown in FIG. 16B, both the shell and core materials are well-crystallized with distinct d-spacings. The shell material has a d-spacing of 2.67 Å, which can be ascribed to the (111) plane of $Li_2O$ (ICDD PDF #: 00-012-0254). The bulk material has a d-spacing of 3.90 Å, which can be assigned to the (101) plane of $La_{0.6}Sr_{1.4}FeO_4$ (ICDD PDF #: 01-072-7578). These results indicate that bulk LSF is covered by a layer of $Li_2O$ with a thickness less than 5 nm. Such a thickness is consistent with XPS observations and can explain the absence of $Li_2O$ phase in XRD characterizations.

Figure 18A:
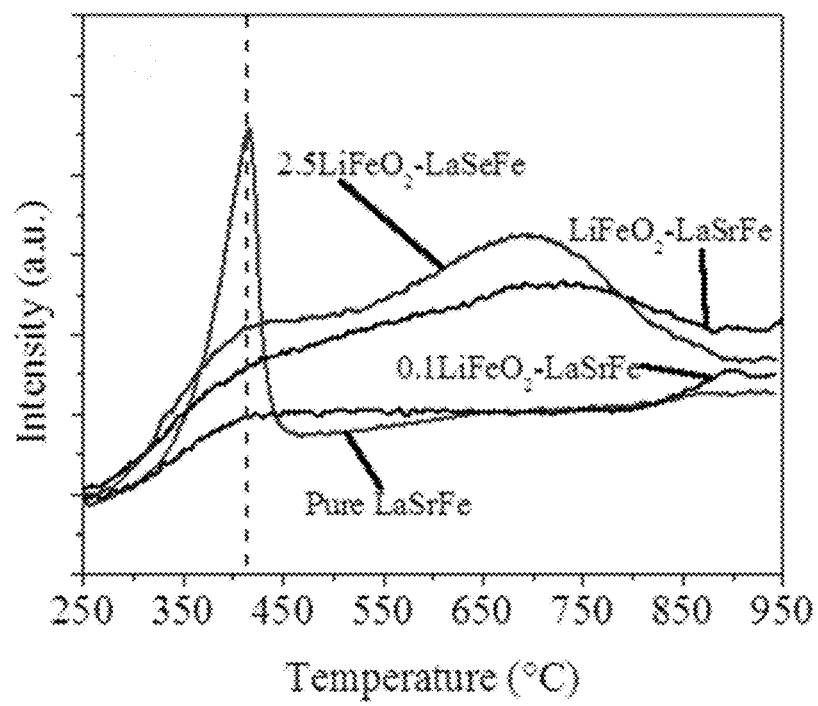
FIGS. 18A-18B show (FIG. 18A) O$_2$-TPD and (FIG. 18B) H$_2$-TPR profiles and characteristic peaks for pure LSF, 0.1LiFeO$_2$-LSF, LiFeO$_2$-LSF and 2.5LiFeO$_2$-LSF. Both temperature ramping rate=5° C./min.

$O_2$-TPD is also performed to characterize relative amounts of chemisorbed and lattice oxygen species. FIG. 18A shows the $O_2$-TPD profiles for each sample. The intensities of the signals are normalized based on LSF content. For pure LSF, there is a significant peak at ca. 410° C., which can be assigned to the chemisorbed alpha-oxygen peak.[29] The high intensity of the alpha-oxygen peak in pure LSF corresponds well with XPS findings and can explain its high selectivity towards complete oxidation. In the cases of all Li promoted sample, the peak intensity significantly declines, forming shoulders stretching from ca. 350 to 450° C. This again confirms that the amount of electrophilic surface oxygen species is significantly reduced due to the effect of Li promoting. While XPS data indicates that Li cation enrichment on catalyst surface decreases the amount of electrophilic surface oxygen species at ambient temperature, TPD result suggests that such an outer layer may serve as a barrier to inhibit outwards diffusion of $O^{2-}$ and its evolution into surface oxygen species.

Figure 17:
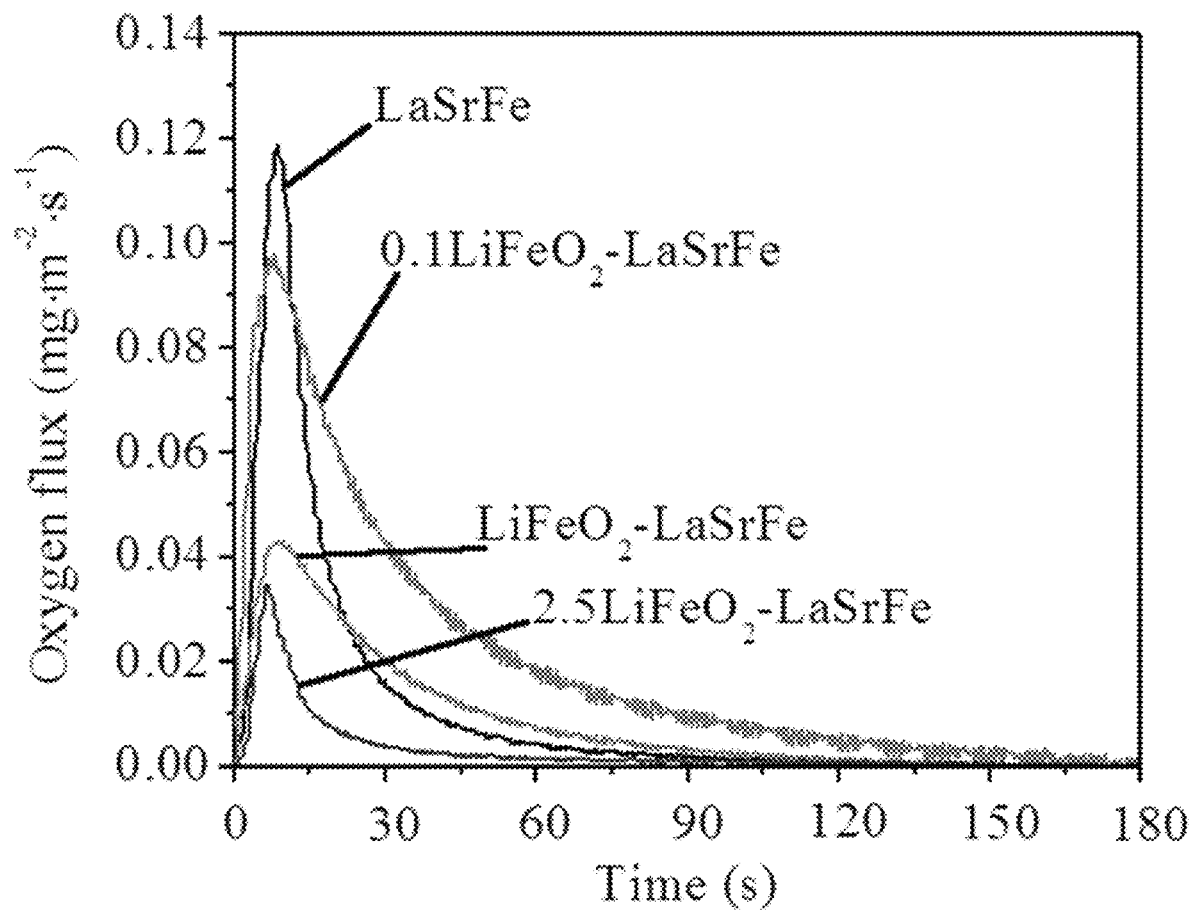
FIG. 17 shows calculated oxygen flux from mass spectroscopy of products on LSF, 0.1LiFeO$_2$-LSF, LiFeO$_2$-LSF and 2.5LiFeO$_2$-LSF as a function of reduction time.
Figure 18B:
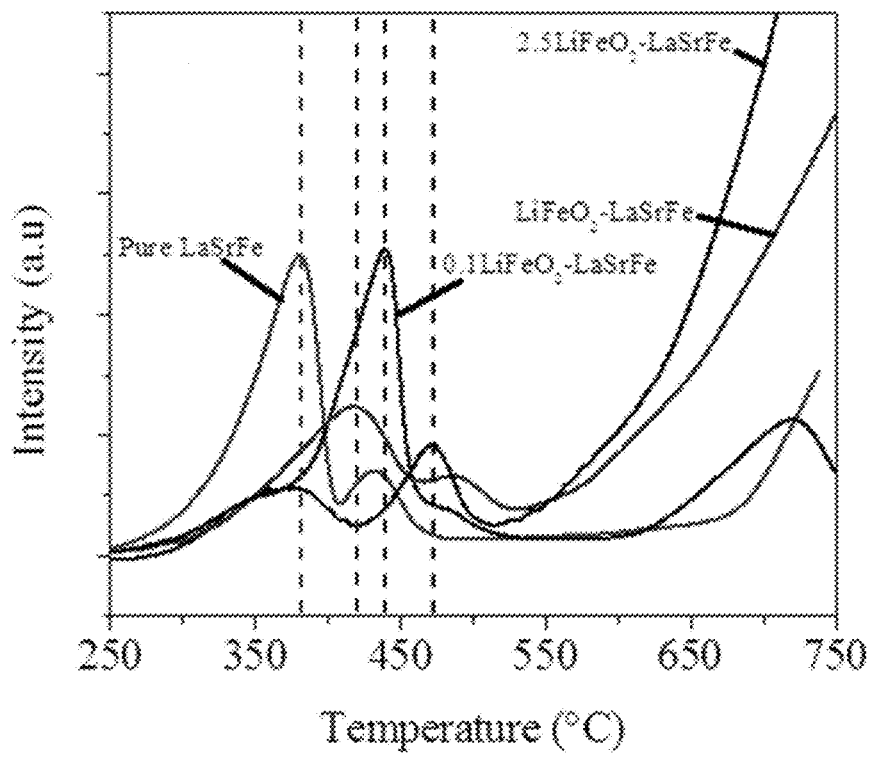

To investigate the reducibility of the redox catalysts, $H_2$-TPR is performed on pure LSF and Li promoted LSF. The intensities of the signals are also normalized based on LSF content. As is shown in FIG. 18B, the TPR experimental profiles present two main reduction peaks at 350-500° C. and above 700° C. The low temperature reduction peaks correspond to changes in iron valence states from $4/3^+$ to $3/2^+$ whereas the high temperature reduction peak should correspond to the formation of metallic iron from $Fe^{2+}$. The positions of the initial reduction peaks follow the sequence LSF<$0.1LiFeO_2$-LSF≈$LiFeO_2$-LSF<$2.5LiFeO_2$-LSF and the peak intensities with LSF≈$0.1LiFeO_2$-LSF>$LiFeO_2$-LSF>$2.5LiFeO_2$-LSF, both with temperature increasing from left to right. These results clearly indicate that addition of Li promoters decreases the reducibility of the LSF phase. The relationship between the reducibility of bulk oxygen and ODH selectivity has been reported by Blasco and Nieto.[48] Lower reducibility generally corresponds to higher ODH selectivity. Since increasing Li promoter amount leads to increased Li enrichment near the surface, decreased redox catalyst reducibility for samples with high Li loading can be explained by the presence of Li cation enriched surface layer which inhibits $O^{2-}$ diffusion from the bulk. Oxygen flux from redox catalysts can be calculated in light of the reactivity data and specific surface area. FIG. 17 shows the oxygen flux for pure LSF and Li promoted LSF. 37.5% ethane (40 ml·min$^{-1}$, balance Ar) is used as reducing gas for a 3 min reduction half-cycle at 700° C. For all samples, the oxygen flux have maximum peaks at about 15 s. The oxygen flux fade out within 2 minutes, indicating a complete consumption of active oxygen. The highest maximum oxygen flux value is observed in pure LSF and it decreases with the addition of Li. Such a maximum oxygen flux value can reflect the bulk $O^{2-}$-conduction rate. It is calculated that unpromoted LSF and 2.5LiFeO$_2$-LSF have a maximum oxygen flux of 0.12 mg·s$^{-1}$·m$^{-2}$ and 0.04 mg·s$^{-1}$·m$^{-2}$, respectively. This further confirms the slowed $O^{2-}$ diffusion rate with Li addition. Compared with the aforementioned TPD results, moderating the $O^{2-}$ diffusion rate to the redox catalyst surface can in turn lead to decreased electrophilic surface oxygen species via oxygen evolution. It is noted that a similar core-shell effect has been reported in MgO/Dy$_2$O$_3$ supported molten alkali metal chloride catalysts.[32] In such catalysts, active intermediate OCl$^-$ diffuses through the LiKCl outerlayer and reacts selectively with ethane. The molten layer can avoid direct contact of ethane with surface electrophilic oxygen species.

Figure 19A:
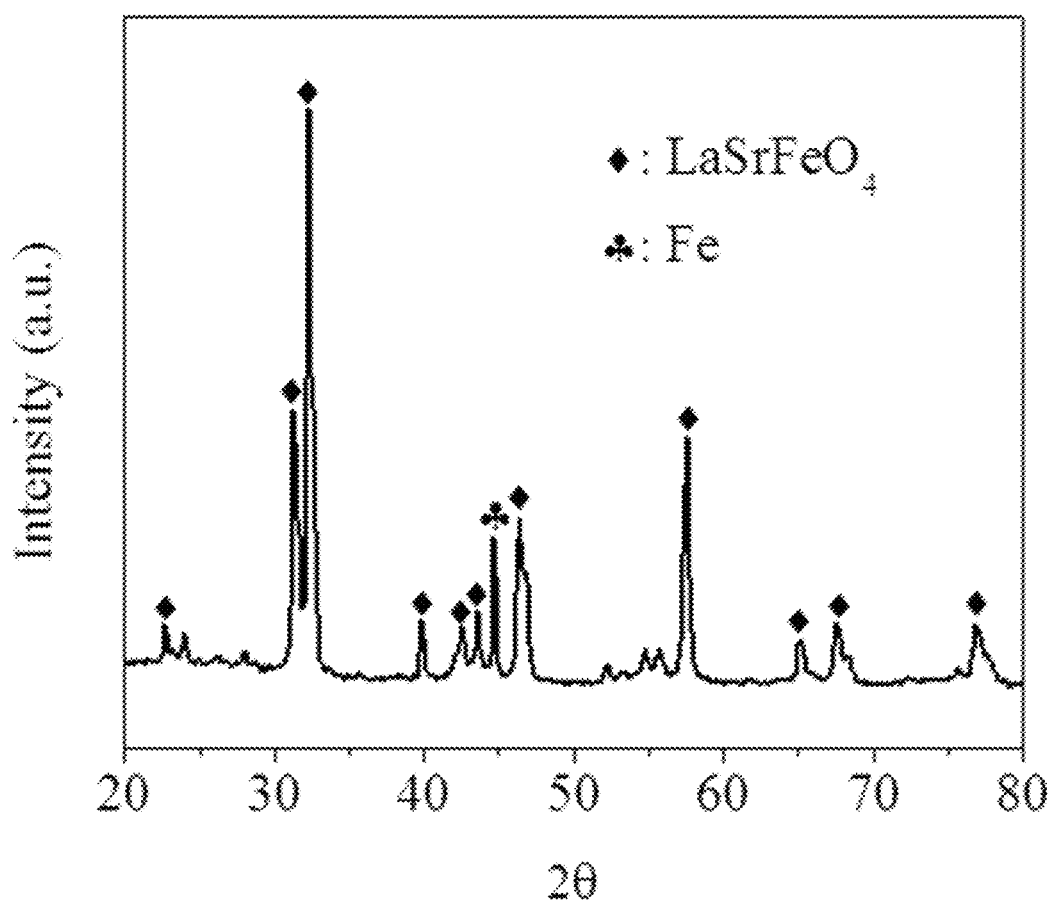
FIGS. 19A-19C show XRD pattern of reduced (FIG. 19A) La$_{0.6}$Sr$_{1.4}$FeO$_4$ (FIG. 19B) LiFeO$_2$-LSF (FIG. 19C) 2.5LiFeO$_2$-LSF. ▲: La$_x$Sr$_{2-x}$FeO$_{4-\delta}$; ♦: Fe.
Figure 19B:
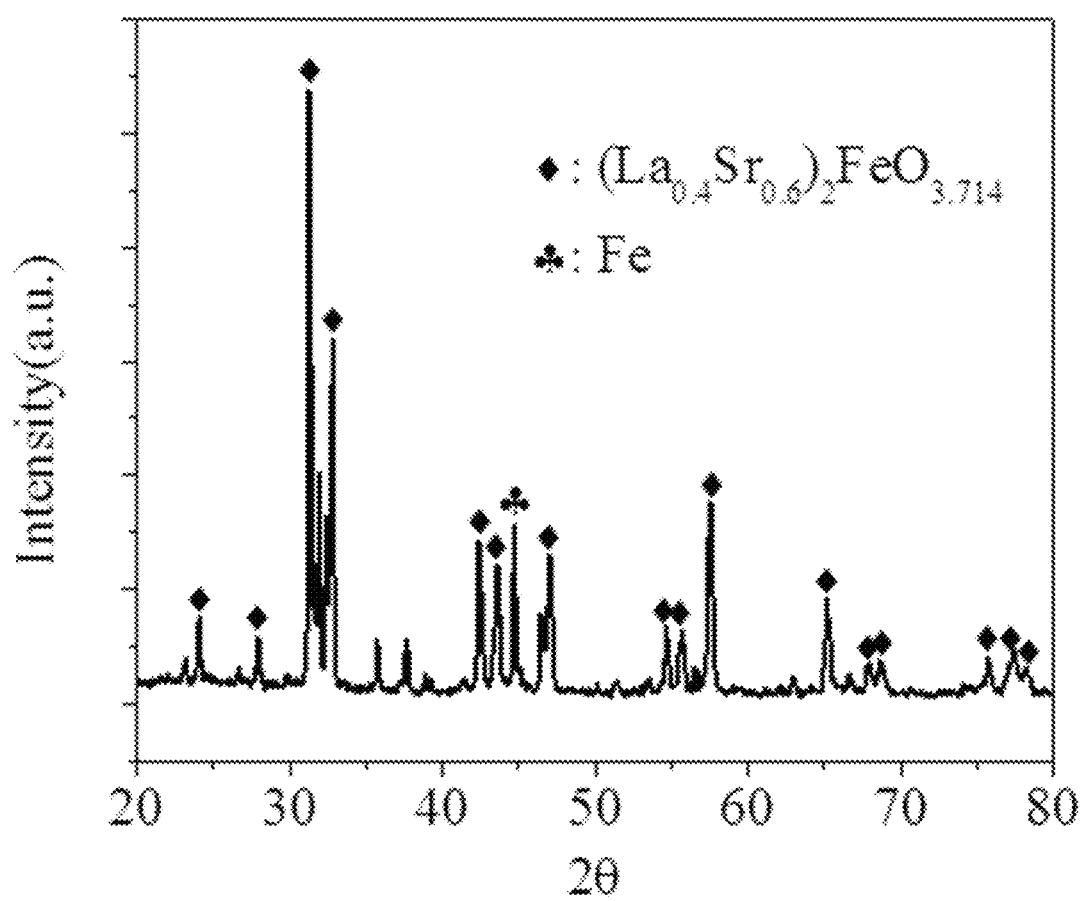
Figure 19C:
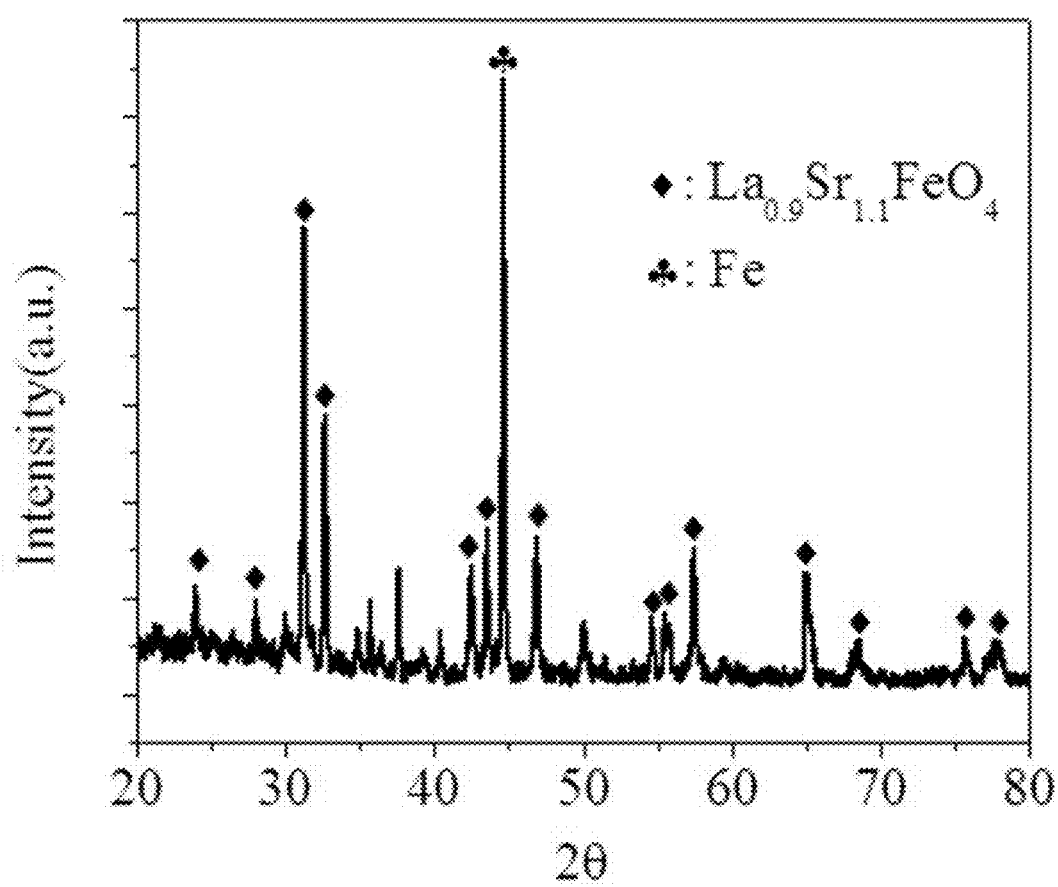

The redox catalysts are reduced in 37.5% ethane (40 ml·min$^{-1}$, balance Ar) for 5 minutes in each reduction half-cycle. FIGS. 19A-19C show the XRD patterns obtained on reduced pure LSF, LiFeO$_2$-LSF and 2.5LiFeO$_2$-LSF. A metallic iron phase appears on all of the reduced samples but the B-site deficient La$_x$Sr$_{2-x}$FeO$_{4-\delta}$ phase still remains. This indicates that reduction under ethane would not fully decompose the LSF structure. It is noted that no Li-containing phase is obtained under XRD. The disappearance of LiFeO$_2$ indicates that such phase is easier to reduce than LSF, forming metallic Fe and a Li phase that is not detected by XRD due to poor crystallinity and small atomic cross section. The LiFeO$_2$ phase is restored when re-oxidized with air.

Figure 20A:
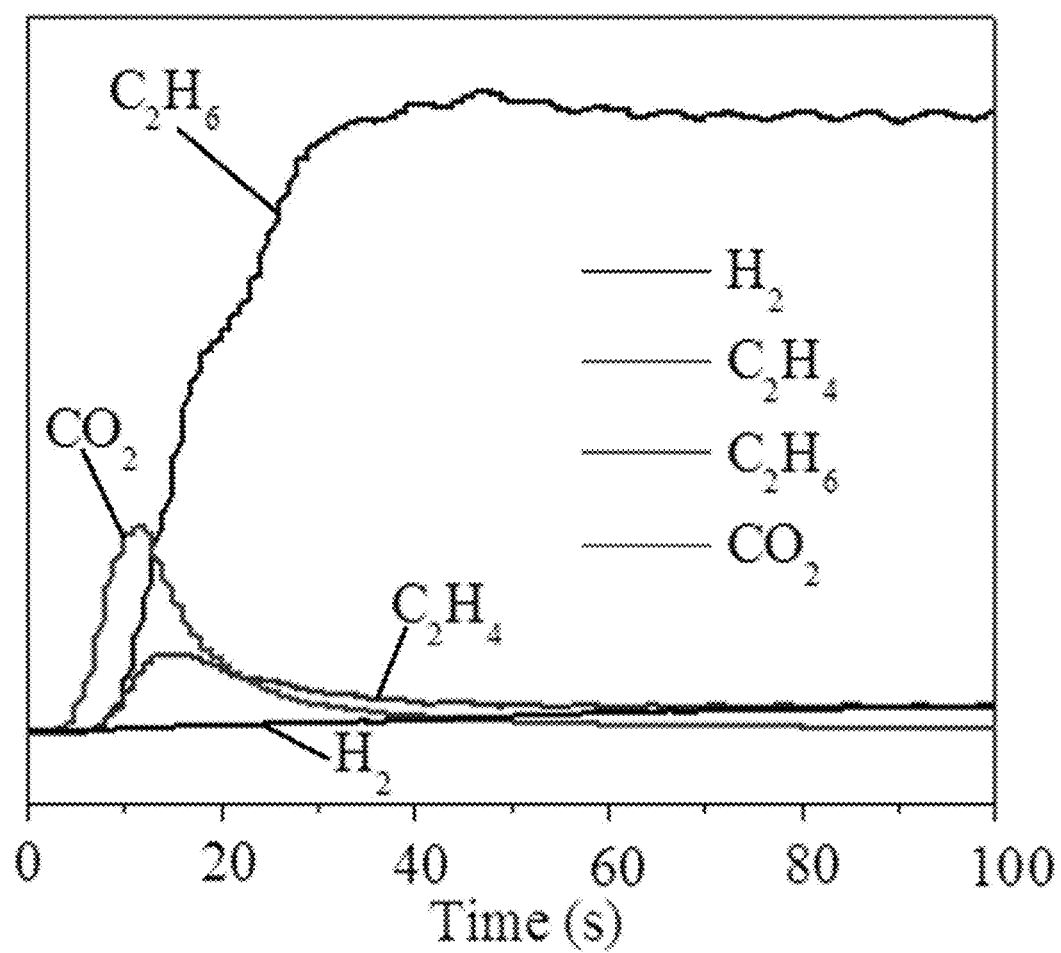
FIGS. 20A-20C show (FIG. 20A) conversion profile for LSF under a 3 min reduction half-cycle.
Figure 20B:
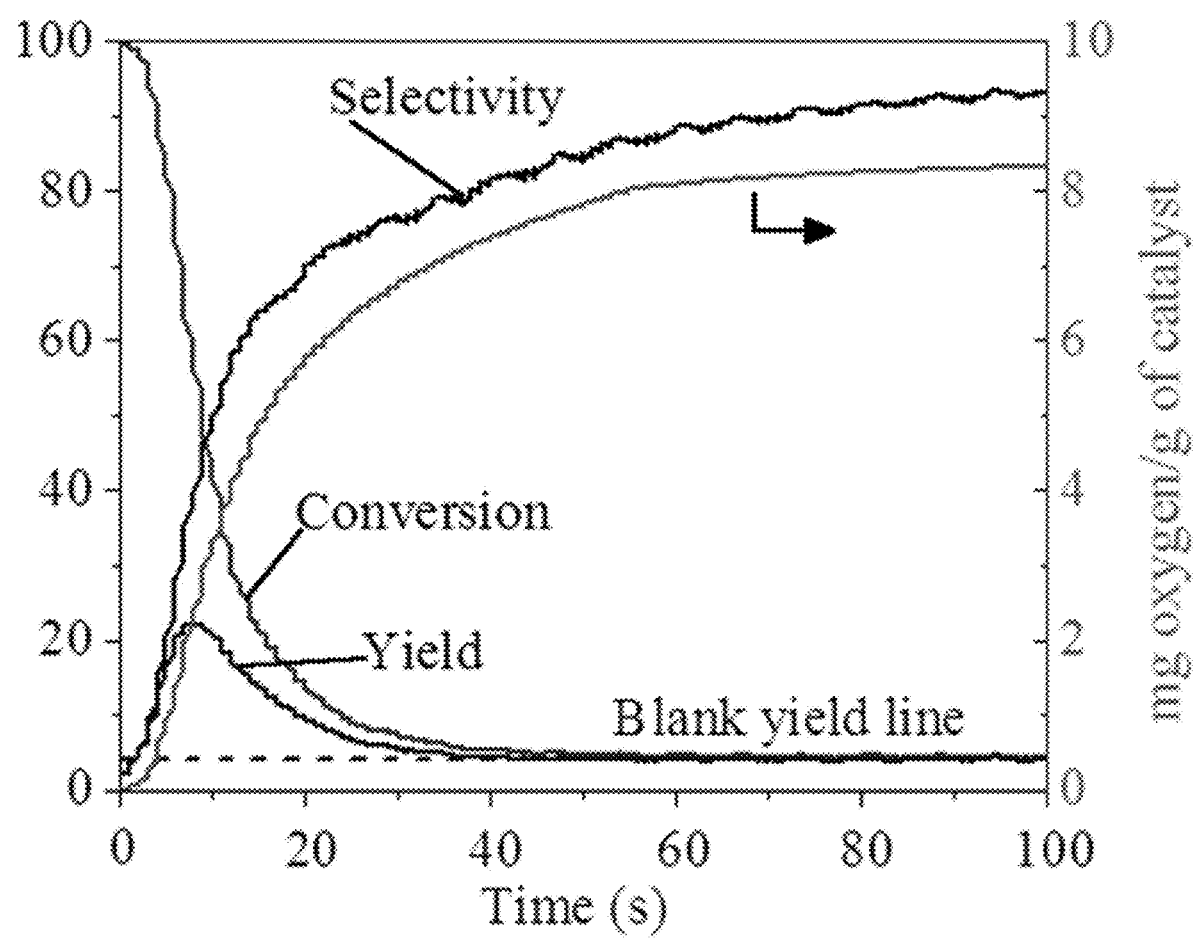
Figure 20C:
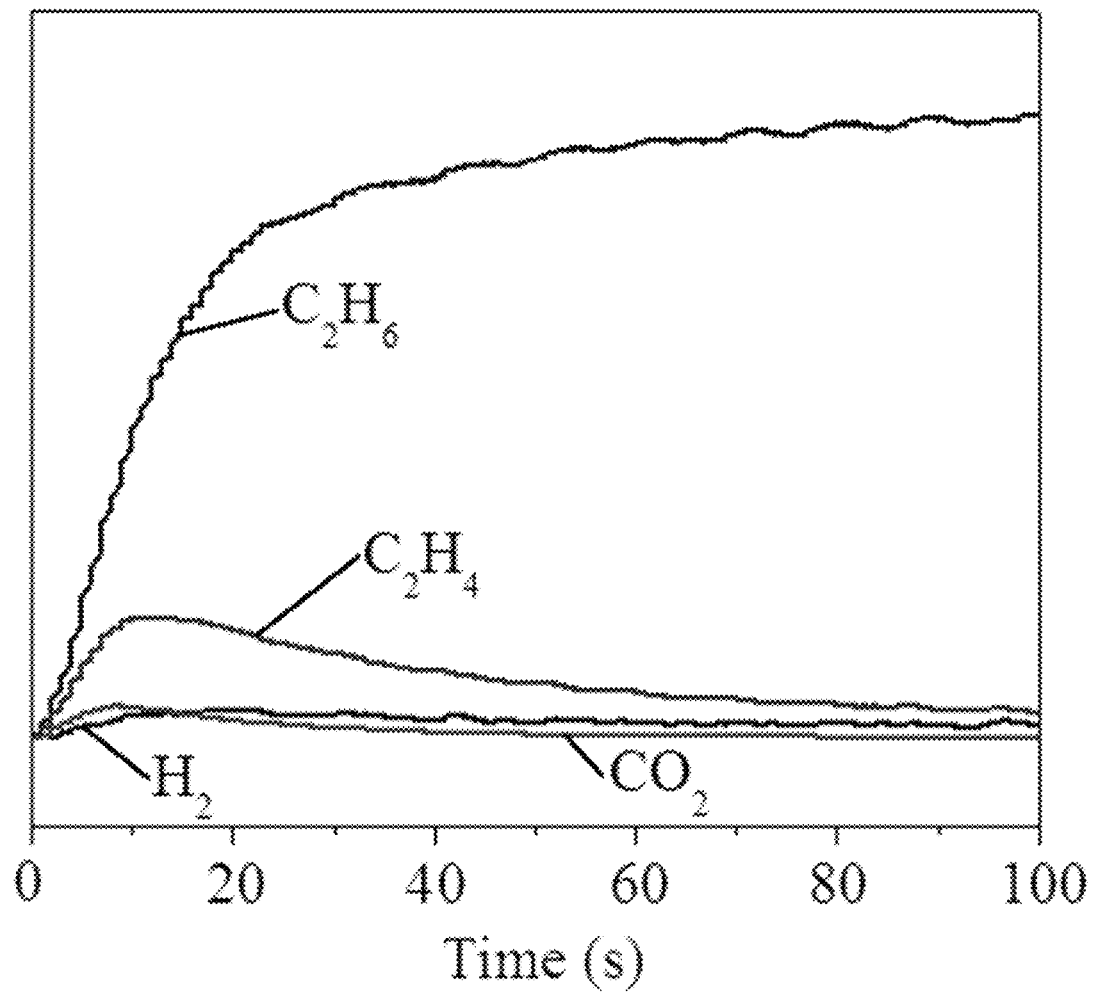

The actual lithium concentrations are examined by using ICP. Table 2 lists the summary of these redox catalysts and their nominal/measured lithium concentrations. The actual lithium concentrations are slightly smaller than the nominal values. This is likely due to some lithium vaporization at the 950° C. sintering temperature. Typical ethane conversion profiles for pure LSF under a continuous flow mode is shown in FIG. 20A. 37.5% ethane (40 ml·min$^{-1}$, balance Ar) is used as reducing gas to react with a fixed bed of redox catalysts for a 3 min reduction half-cycle at 700° C. We observe that C$_2$H$_4$ and CO$_2$ peaks show up within the first minute, i.e. redox catalyst is active at the beginning of the half-cycle. The thermal background becomes dominant as the active oxygen species are consumed. Such a thermal background can be indicated by the similar concentration level of C$_2$H$_4$ and H$_2$ at the end of the reduction half-cycle. FIG. 20B shows the redox catalyst selectivity/conversion/yield and the oxygen consumption with the function of reduction time. Pure LSF shows 160% larger oxygen capacity (0.8 wt %) than 2.5LiFeO$_2$-LSF (0.3 wt %, see results and discussions). Pure LSF is good for ethane combustion into CO$_2$ with a low ethylene yield. The typical ethane conversion profiles for 2.5LiFeO$_2$-LSF shows in FIG. 20C. The redox catalyst performance over time is included in results and discussions.

TABLE 2

Redox catalyst samples and their nominal/actual lithium concentrations

| Sample | Nominal Li concentration (wt %) | Measured Li concentration (wt %) |
|---|---|---|
| LSF | NA | NA |
| 0.1LiFeO$_2$-LSF | 0.21 | 0.15 |
| LiFeO$_2$-LSF | 1.65 | 1.42 |
| 2.5LiFeO$_2$-LSF | 3.08 | 2.52 |

Figure 21:
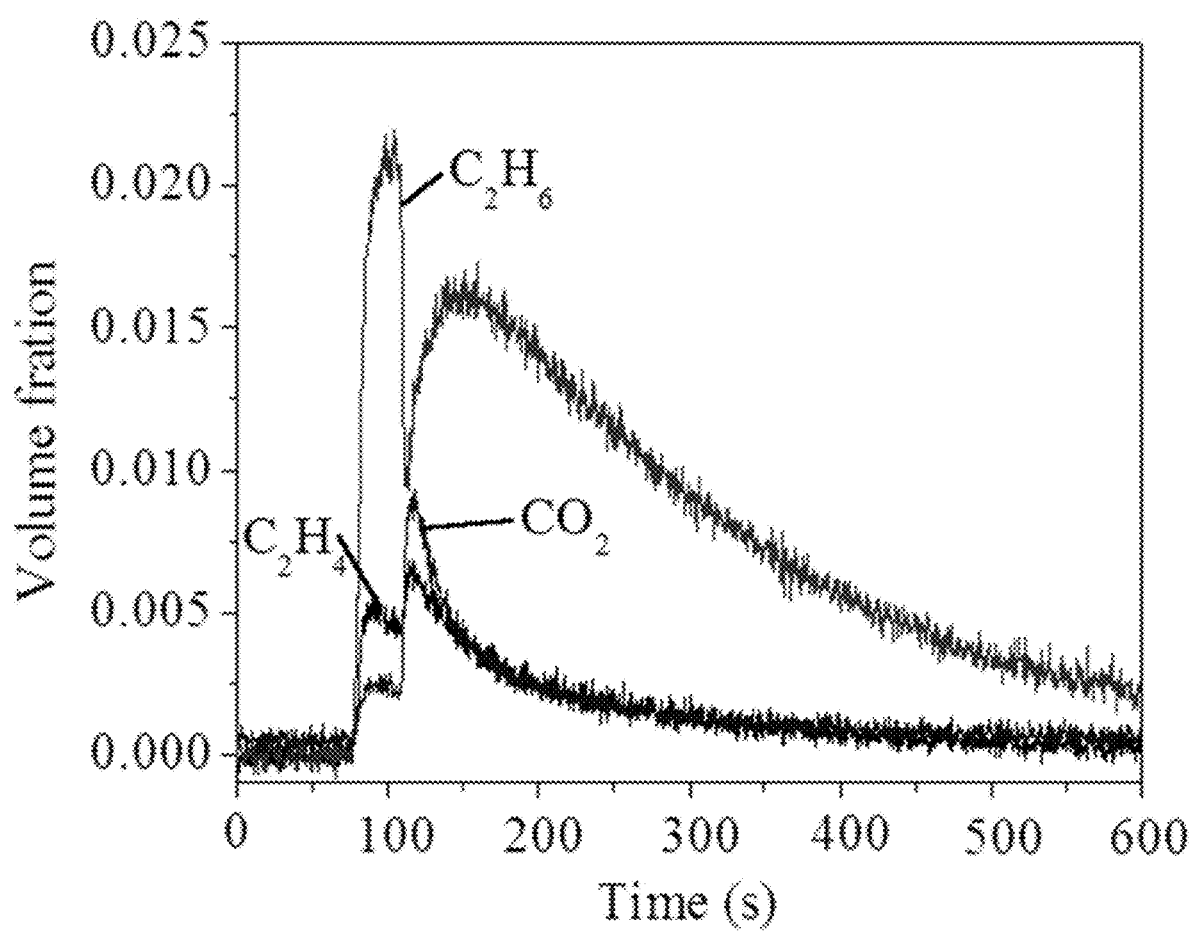
FIG. 21 shows the response to a broadened pulse of ethane combined with a sharp pulse of oxygen on 2.5LiFeO$_2$-LSF at 700° C. at 50 ml·min$^{-1}$ total flow rate.
Figure 22A:
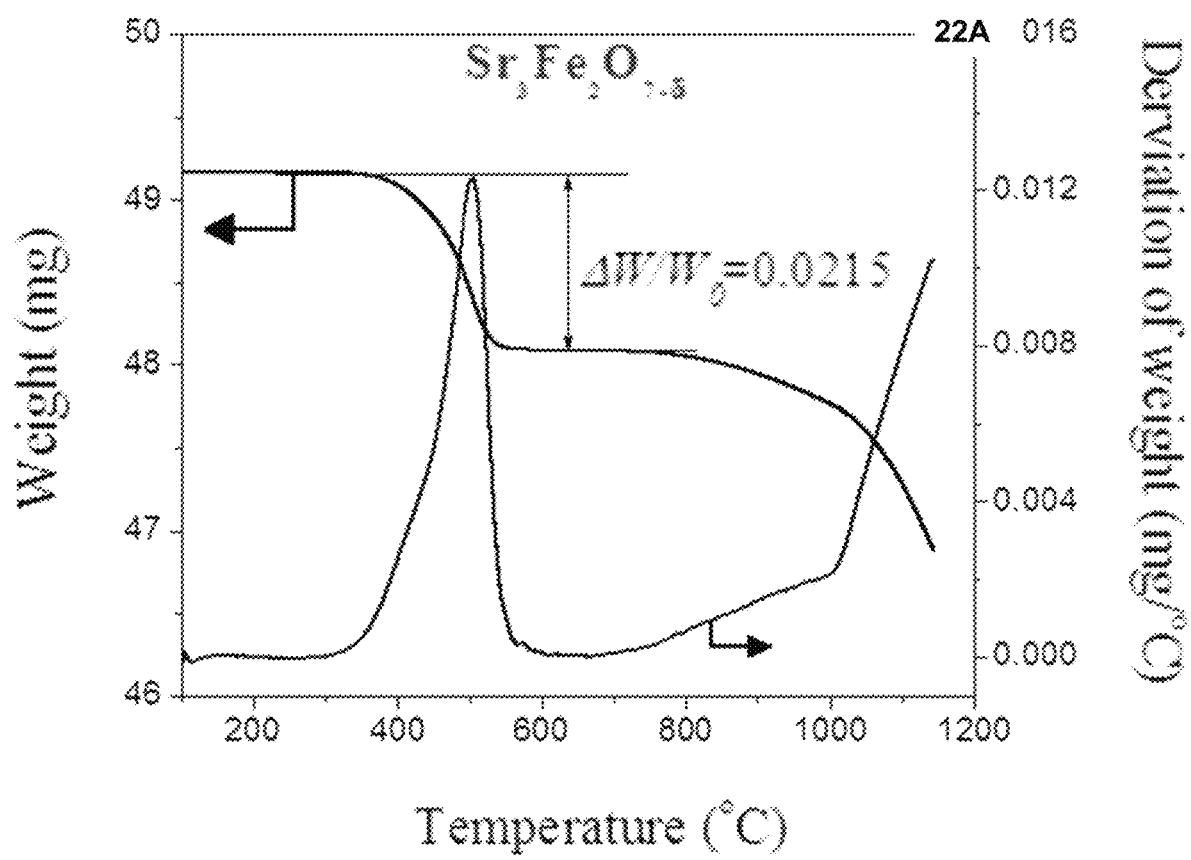
FIGS. 22A-22B show temperature-programmed reduction (TPR) profiles of Sr$_3$Fe$_2$O$_{7-\delta}$ (FIG. 22A) and Na$_2$WO$_4$/Sr$_3$Fe$_2$O$_{7-\delta}$ (FIG. 22B, Na$_2$WO$_4$ loading is 20 wt. %): Total flowrate=100 sccm, y$_{H2}$=0.1, ramping rate=10° C./min.
Figure 22B:
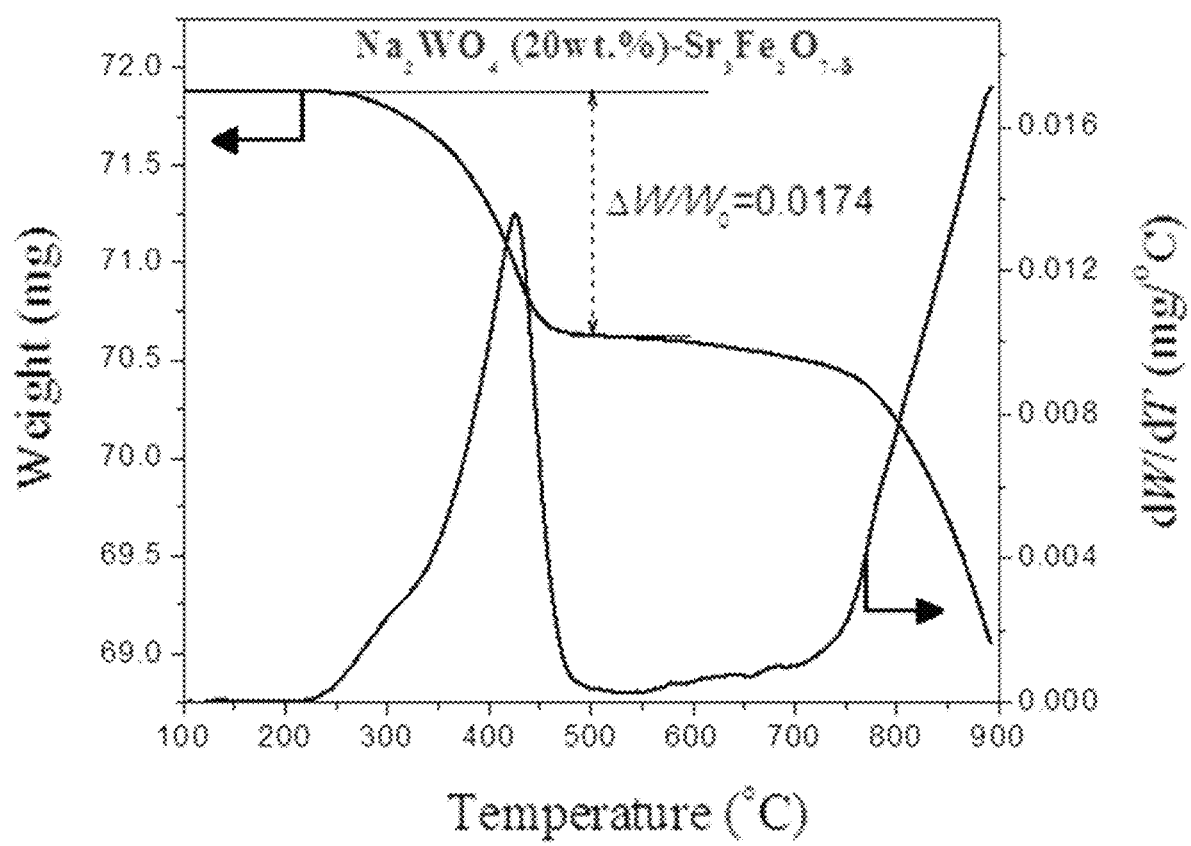
Figure 23A:
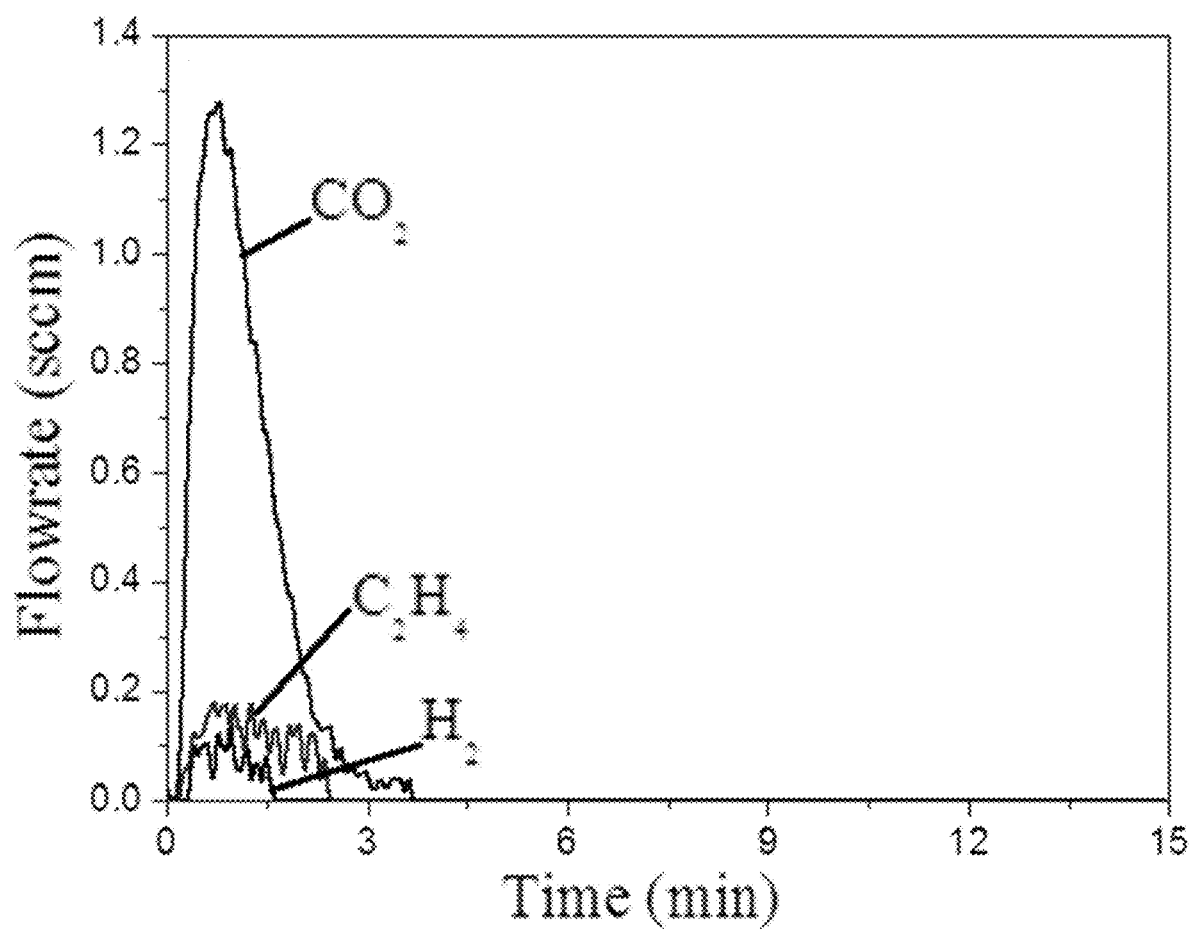
FIGS. 23A-23B show ethane combustion over Sr$_3$Fe$_2$O$_{7-\delta}$ (FIG. 23A) and Na$_2$WO$_4$/Sr$_3$Fe$_2$O$_{7-\delta}$ (FIG. 23B, Na$_2$WO$_4$ loading is 20 wt. %) at 650° C.: Total flowrate=50 sccm, y$_{C2H6,0}$=0.05.
Figure 23B:
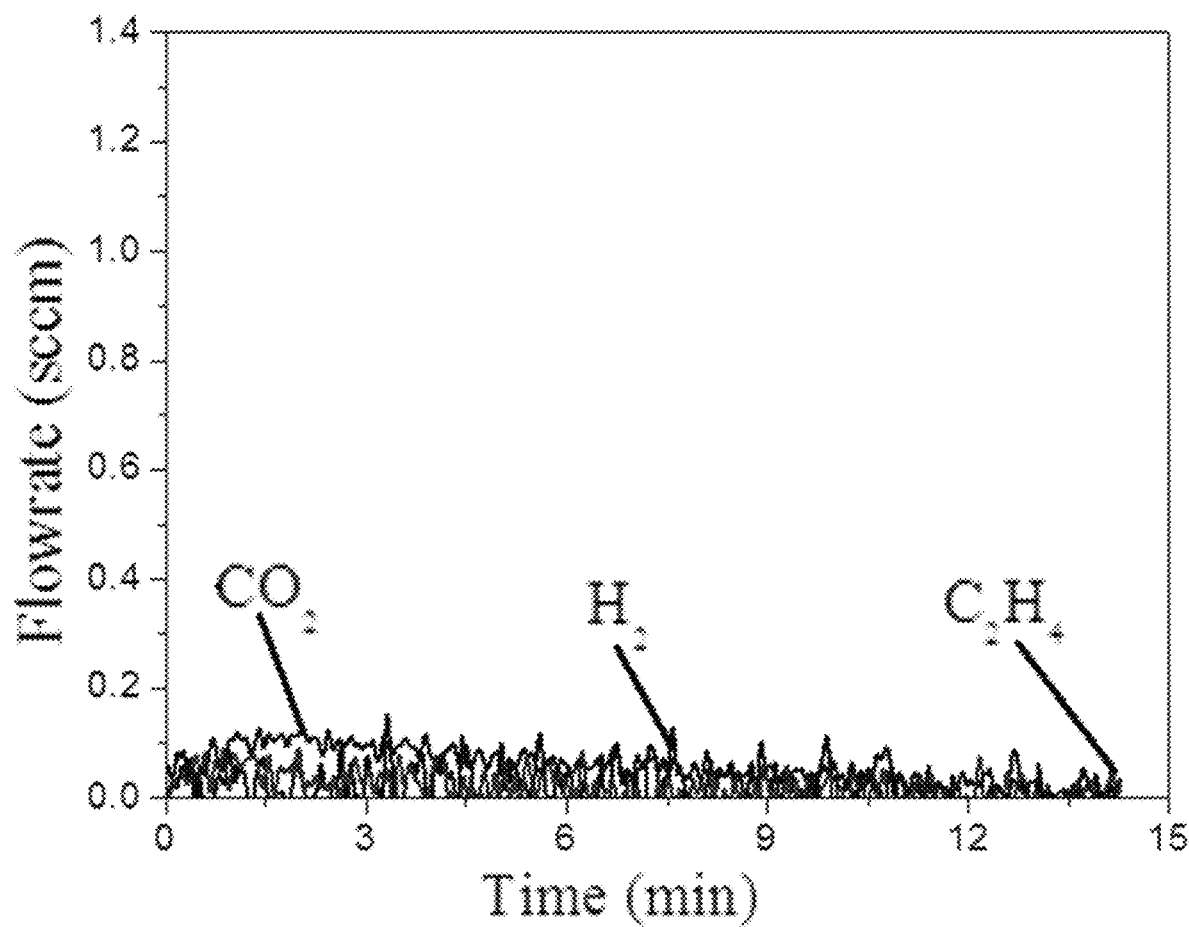
Figure 24A:
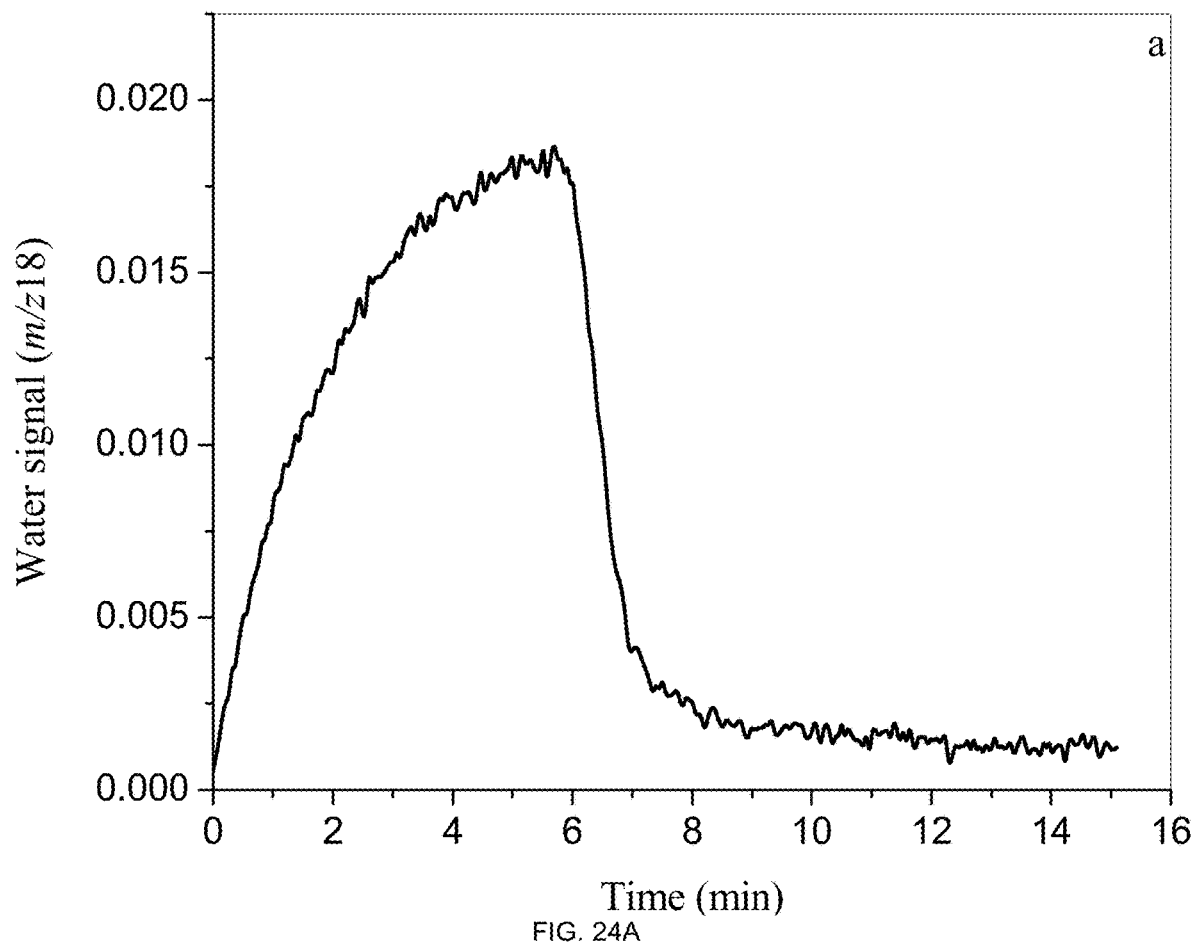
FIGS. 24A-24B show hydrogen combustion over Sr$_3$Fe$_2$O$_{7-\delta}$ (FIG. 24A) and Na$_2$WO$_4$/Sr$_3$Fe$_2$O$_{7-\delta}$ (FIG. 24B, Na$_2$WO$_4$ loading is 20 wt. %) at 650° C.: Total flowrate=50 sccm, y$_{C2H6,0}$=0.05.
Figure 24B:
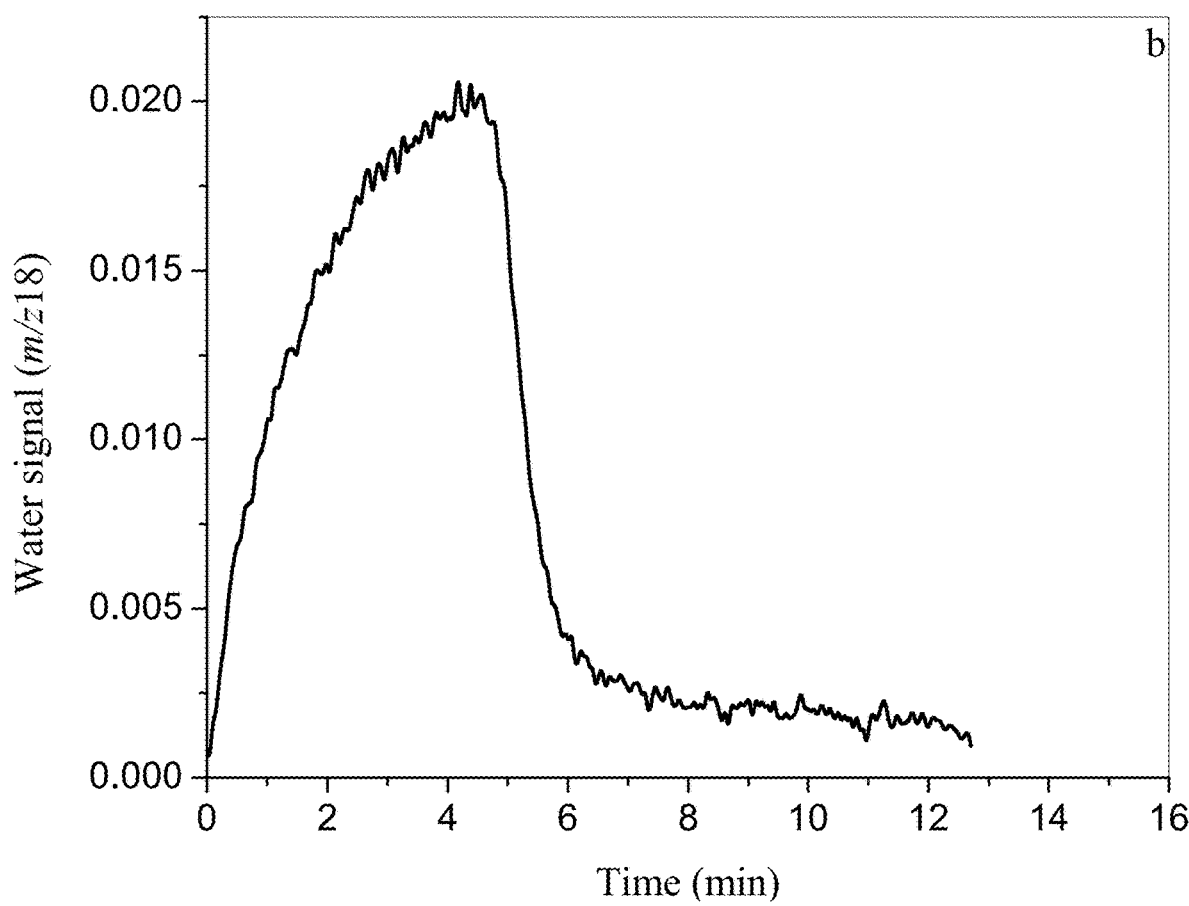
Figure 25:
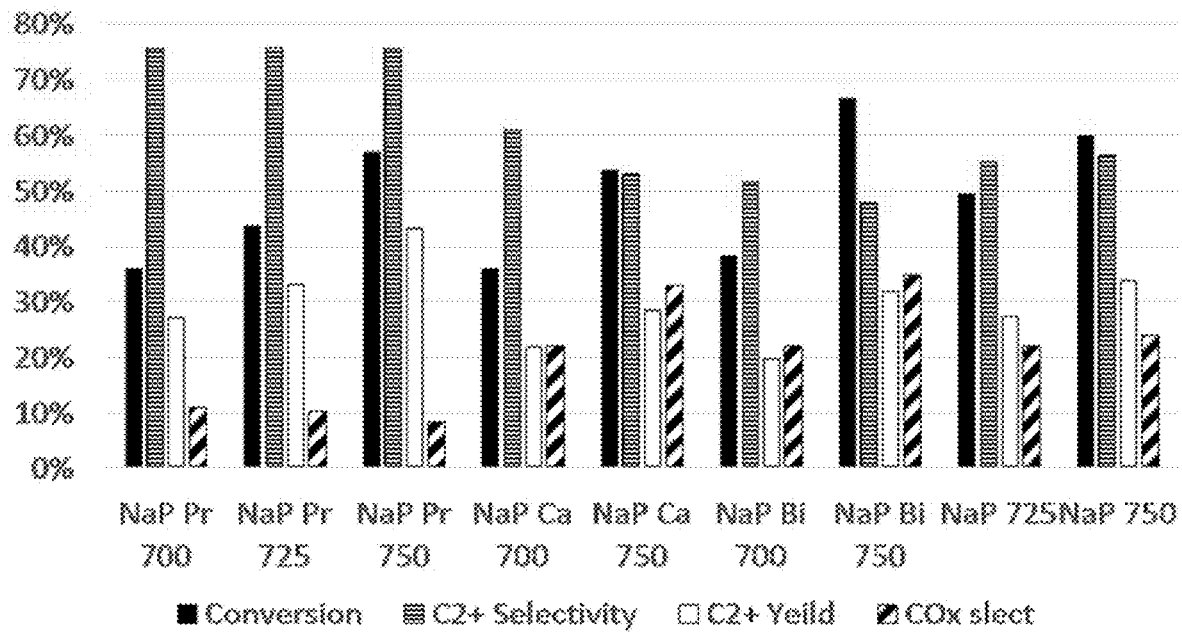
FIG. 25 is a graph of the n-hexane oxi-cracking performance of Mg$_6$MnO$_8$ based mixed oxide redox-catalyst co-doped with sodium pyrophosphate (NaP) and other dopants including Ca, Pr, and Bi.
Figure 26:
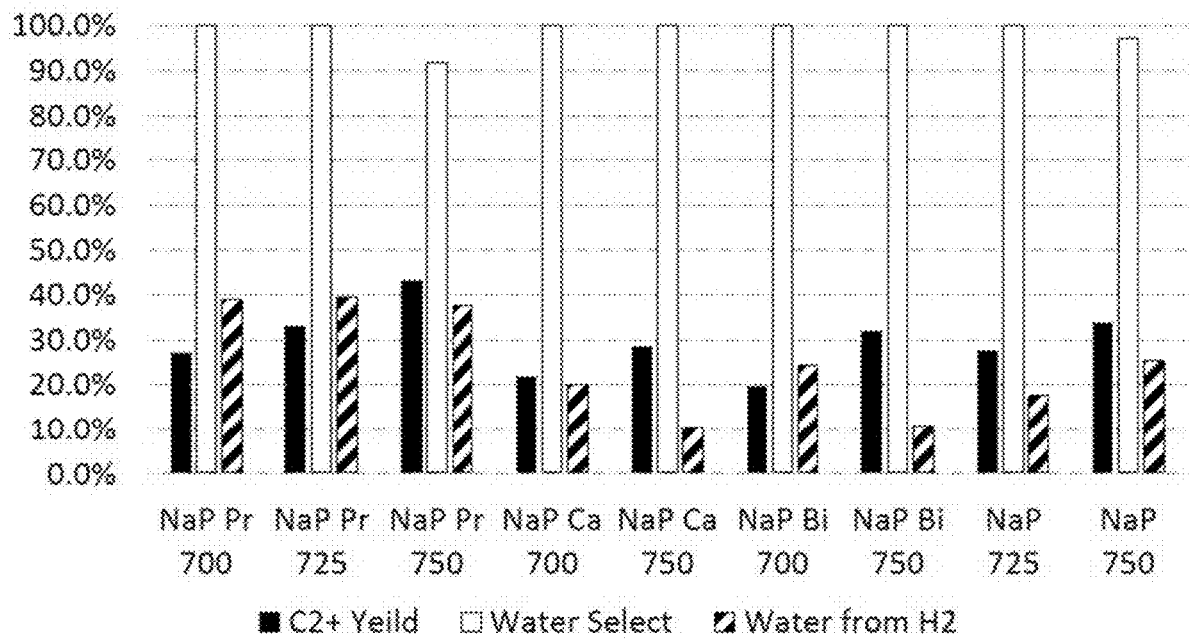
FIG. 26 is a graph of hydrogen conversion performance during n-hexane oxy-cracking over Mg$_6$MnO$_8$ based mixed oxide redox-catalyst co-doped with sodium pyrophosphate (NaP) and other dopants including Ca, Pr, and Bi.
Figure 27:
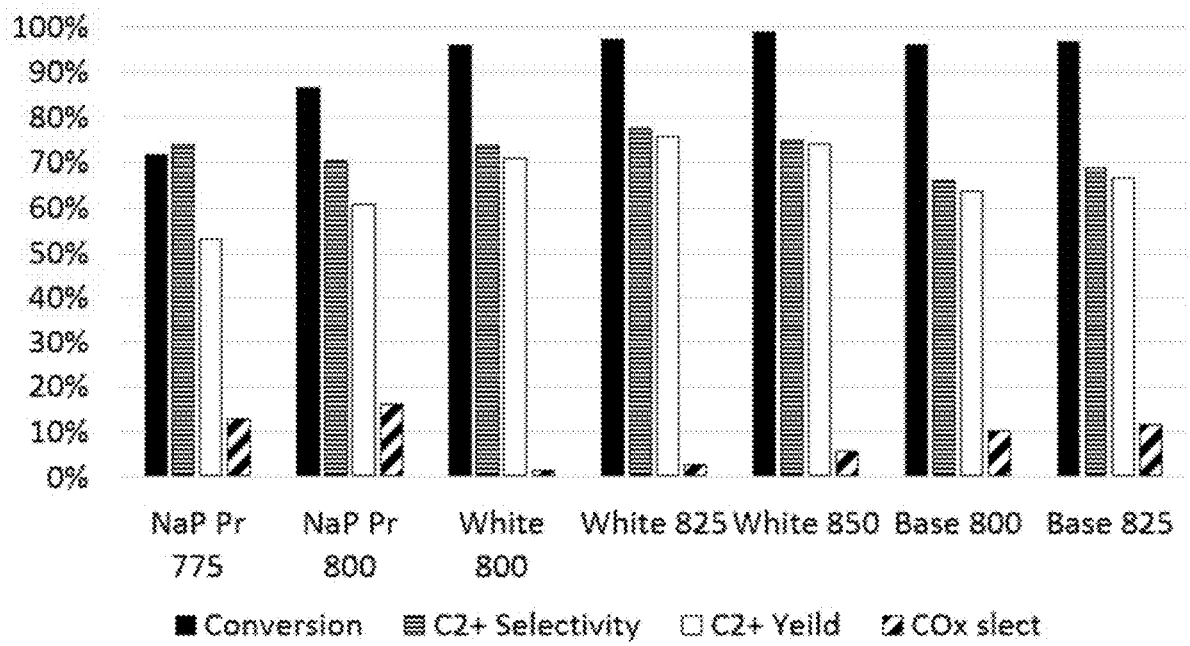
FIG. 27 is a graph of is a graph of the n-hexane oxy-cracking performance of Mg$_6$MnO$_8$ based mixed oxide redox-catalyst alkali only (Base) and doped with sodium pyrophosphate (NaP), vs an ethane ODH catalyst (White).
Figure 28:
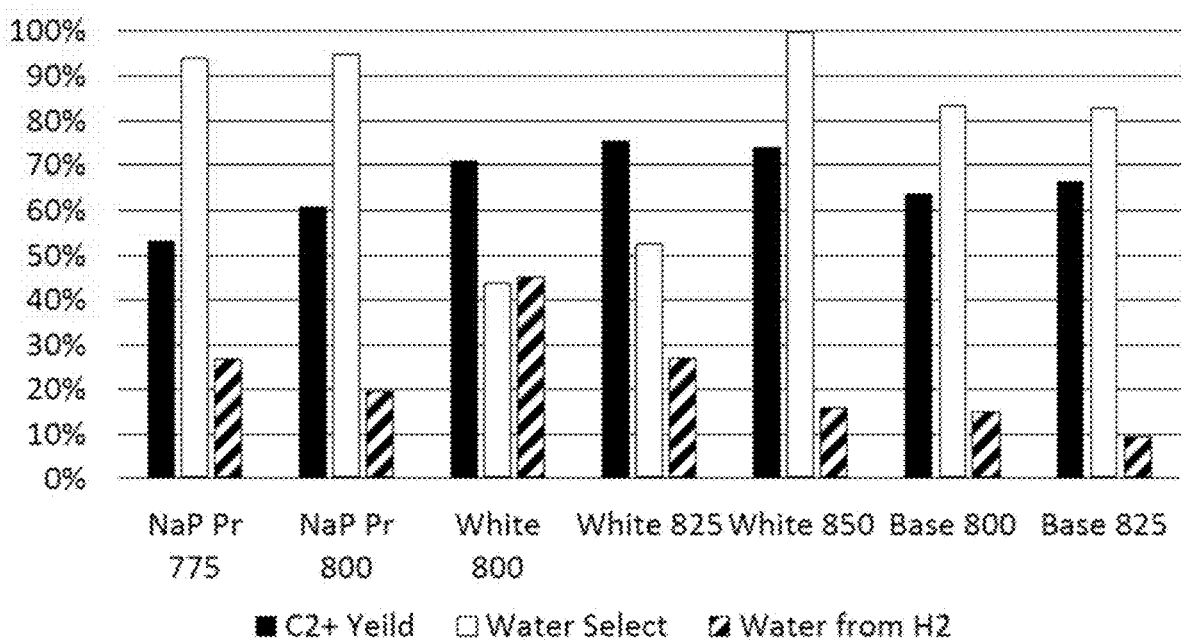
FIG. 28 is a graph of 26 is a graph of hydrogen conversion performance during n-hexane oxy-cracking over Mg$_6$MnO$_8$ mixed oxide redox-catalysts redox-catalyst alkali only (Base) and doped with sodium pyrophosphate (NaP), vs an ethane ODH catalyst (White)

The aforementioned results indicate that regulating the rate of lattice oxygen transport to the redox catalyst surface and inhibiting $O^{2-}$ evolution to electrophilic surface oxygen species can lead to increased redox catalyst selectivity for redox ODH reactions. To further confirm such findings, a broadened ethane pulse coupled with an injection of sharp oxygen pulse is performed. Since gaseous O$_2$ molecule can evolve on the oxide surface via a $O_2^- \to O_2^- \to O_2^{2-} \to O^- \to O^{2-}$ pathway, one would anticipate higher ethane conversion and lower C$_2$H$_4$ selectivity if: 1. $O^{2-}$ conduction is the rate limiting step for ethane oxidation in absence of gaseous oxidant; 2. Electrophilic oxygen species are responsible for CO$_2$ formation. As is shown in FIG. 21, the oxygen pulse causes ethane conversion to increase by nearly 130%. Meanwhile, 40% decrease in ethylene selectivity is observed. These results confirm that the electrophilic oxygen species is primarily responsible for non-selective oxidation and the Li cation enriched surface layer inhibits $O^{2-}$ conduction and evolution to such oxygen species.

Conclusions

The current example investigates Li promoted, B-site deficient iron containing perovskites as redox catalysts for ethane oxidative dehydrogenation under a cyclic redox CL-ODH scheme. The proposed redox scheme allows autothermal ethane dehydrogenation without using gaseous oxygen, rendering a more efficient, environmentally friendly, and safer route for ethylene production. While perovskites without Li promoter exhibit high selectivity towards CO$_2$ formation, addition of Li leads to high ethylene selectivity/yield and good regenerability. Up to 90% ethylene selectivity and 61% conversion are observed. Li-promoted redox catalysts exhibit oxygen carrying capacity up to 0.6 w.t. % with near 100% H$_2$O selectivity, making it potentially suitable for the proposed CL-ODH operations. Mechanistic investigation indicates that selectivity of the redox catalyst can be enhanced by regulating the rate of $O^{2-}$ conduction and evolution through surface enrichment of Li cation on the redox catalyst. This is evidenced by XPS, TEM, O$_2$-TPD and H$_2$-TPR studies. XPS study indicates Li enrichment on the oxide surface, which is confirmed by TEM. Detailed O 1s XPS scans show a decreased amount of electrophilic surface oxygen species with Li promotion. Further investigation with O$_2$-TPD also confirms that Li promoter reduces the non-selective electrophilic oxygen species. Moreover, the presence of Li cation enriched surface layer decreases the reducibility of the redox catalyst. Because CL-ODH reaction involves the oxygen species supplied from bulk lattice oxygen species, it is hypothesized that the presence of Li cation enriched surface increases the resistance of $O^{2-}$ diffusion from the bulk and its subsequent evolution into electrophilic oxygen species on the surface. The non-selective nature of the surface oxygen species and the inhibition effects of Li promoter on $O^{2-}$ diffusion are also confirmed by pulse experiments. Based on such findings, it is concluded that Li promoted La$_x$Sr$_{2-x}$FeO$_{4-\delta}$ can be an effective redox catalyst for ethane ODH in absence of gaseous oxygen.

Example 2

La$_{0.6}$ Sr$_{1.4}$ FeO$_4$ (LSF) was prepared by the modified Pechini method in which stoichiometric amounts of La-, Srand Fe-nitrate precursors are dissolved in water and heated with citric acid to form a sticky gel. The resulting mixture is dried and calcined in air and then impregnated with $LiFeO_2$ in a 2.5:1 molar ratio of $LiFeO_2$:LSF. Subsequent calcination results in a LSF coated with a mixture of $LiFeO_2$/LiOH and/or $Li_2O$. The catalyst thus self assembles into a core-shell structure where the oxygen carrier LSF phase is coated with a $LiFeO_2$/LiOH/$Li_2O$ overlay that promote dehydrogenation and hydrogen oxidation while preventing contact with deep oxidizing species in the core. In the experiments 0.5 g of catalyst were packed into a 1/8" ID quartz U-tube reactor with inert grit placed on both side of the bed to control the gas volume of the heated zone. The U-tube reactor was heated in a tube furnace and 37.5 µL pulses of ethane (diluted in 63.5 µL argon) was pulsed into the rector at a GHSV of 3000 $h^{-1}$ at 650, 675, and 700° C. resulting in higher conversions of ethane and selectivity of ethylene as shown Table 3. The performance was such that over 60% conversion with 90% selectivity was observed at 700° C. where thermal cracking conversion is negligible.

TABLE 3

Conversion of ethane and Selectivity/Yield of ethylene over $LiFeO_2$/LSF from pulse experiments

| Temperature (° C.) | Conversion | Selectivity | Yield |
|---|---|---|---|
| 650 | 32.1% | 95.2% | 30.6% |
| 675 | 48.5% | 94.1% | 45.6% |
| 700 | 60.2% | 90.2% | 54.3% |

Example 3

$Mg_6MnO_8$ doped with sodium and phosphorous was prepared; magnesia powder was impregnated with a solution of a stoichiometric amount of manganese (II) nitrate and sodium pyrophosphate (corresponding to 1.7 wt. % Na) dried at 80° C. and calcimined at 950° C. The prepared catalyst was further doped with Pr so that it constituted a 5 wt. % loading. 10% n-hexane balanced with argon was flown over 0.5 g of the catalyst at 775° C. at 150 SCCM for 20 seconds, with regeneration in oxygen between reduction steps. Product distributions are given in Table 4. A conversion of 71.5% was observed with a yield of olefins and di-olefins 52.8% (carbon basis) vs. a conversion and yield of 55.9% and 44.8% respectively for thermal cracking. The performance was such that, compared to thermal background conversion, it produced higher yields even with the formation of $CO_N$. In spite of a higher conversion to unsaturated hydrocarbons, less hydrogen is observed in the outlet of the oxy-cracking catalyst relative to thermal cracking (Table 5). The amount of water formed shows that a significant portion of the hydrogen is combusted, providing 20% heat to the reaction.

TABLE 4

Product yield oxy-cracking over 10% n-hexane at 775° C. and 150 sccm. % Yield (Carbon Basis)

| | Thermal | Oxy-Cracking |
|---|---|---|
| Methane | 5.2% | 6.0% |
| CO | 0.0% | 0.6% |

TABLE 4-continued

Product yield oxy-cracking over 10% n-hexane at 775° C. and 150 sccm. % Yield (Carbon Basis)

| | Thermal | Oxy-Cracking |
|---|---|---|
| $CO_2$ | 0.0% | 8.5% |
| Ethane | 1.7% | 1.7% |
| Ethylene | 21.7% | 27.8% |
| Acetylene | 0.0% | 0.1% |
| Propane | 0.5% | 0.4% |
| Propylene | 12.9% | 12.2% |
| Butane | 0.1% | 0.1% |
| Butylene | 7.0% | 7.3% |
| 1,3 butadiene | 1.6% | 4.2% |
| Pentene | 1.6% | 1.3% |

TABLE 5

Mol % of hydrogen and water in outlet for thermal cracking and oxy-cracking over 10% n-hexane at 775° C. and 150 sccm. Mol % Hydrogen/Water (argon free basis)

| | Thermal | Oxy-Cracking |
|---|---|---|
| $H_2$ | 8.9% | 1.7% |
| $H_2O$ | 0 | 34.16% |

Example 4

Sodium tungstate/$CaMnO_3$ was prepared by wet impregnation of sodium tungstate onto $CaMnO_3$ prepared by the modified Pechini method as laid out in example A. This catalyst was placed into a quartz U-tube reactor and heated. In separate runs it was contacted with 5% hydrogen and 5% ethane diluted with argon at 650° C. Mass spectroscopy measurements indicate that nearly all hydrogen is consumed for ~20 min. In the ethane experiment no activity was observed, indicating that the oxygen carrier selectively burns hydrogen. A Cr/$Al_2O_3$ non-oxidative dehydrogenation co-catalyst was prepared by impregnation of chrome nitrate onto an alumina support, followed by calcination at 800° C. When contacted with 5% ethane as in the $CaMnO_3$ experiment, it produces hydrogen and ethylene. However, when Cr/$Al_2O_3$ is used as a co-catalyst packed before a bed of $CaMnO_3$, the hydrogen produced by the dehydrogenation catalyst is consumed by the $CaMnO_3$ oxygen carrier with little formation of $CO_x$. The overall lattice oxygen capacity of the catalyst was determined to be over 9 wt. %.

Example 5: N-Hexane Cracking

Catalyst with substantial composition of $Mg_6MnO_8$ were prepared either as in example 6 or by solid state methods. In solid state methods a physical mixture of $MnO_2$ and MgO powered are mixed along with and alkaline containing constituent such as sodium pyrophosphate or sodium hydroxide either dry or in the presence of water which forms a slurry. The resulting mixture is calcined at 800-1000° C. Additional dopants such as calcium nitrate, praseodymium nitrate, and Bi nitrate are added by impregnating the calcined redox catalyst with an aqueous solution of the dopant, followed by drying and calcining again. For each characterization run 10% n-hexane, balanced with argon, was flown over 0.5 g of the catalyst at 700-825° C. at 150 SCCM for 20 seconds in a 1/4" O.D. u-tube, with regeneration in dilute oxygen between reduction steps. The conversion, carbon selectivity and hydrogen selectivity are reported in FIGS. 25-28. The results show that dopants may be used to tune the system towards higher thermal output (by hydrogen and carbon selectivity to water and $CO_x$ respectively) or higher selectivity to olefins.

Example 6: Li and K Co-Promoted LaSrFe

Synthetic procedure: In synthesis of Li and K co-promoted LaSrFe, nitric precursors of K, Li, La, Sr and Fe were added together and dissolved into water, forming one solution. Citric acid is then added to the solution at a 3:1 molar ratio to metal ions. The solution is kept stirring at 50° C. for 0.5 h to form a chelating solution. Ethylene glycol is then added to the solution to promote gel formation. The molar ratio between ethylene glycol and citric acid is 2:1. The solution is kept at 80° C. under stirring until a viscous gel formed. The gel is dried overnight at 130° C. in a convection oven. The sample is then calcined in a tube furnace at 950° C. for 12 h under continuous air flow.

Reactivity testing: Both transient pulse mode and continuous flow mode are used to test the reactivity performance of redox catalysts. The reaction temperature is 700° C. 0.5 g of the redox catalysts are placed in a fixed-bed quartz U-tube reactor (I.D.=⅛ inches). Inert silicon carbide are loaded on both sides of the U-tubes to reduce the void volume for thermal conversion of ethane. Transient pulse experiments are conducted to obtain the conversion/selectivity/yield of a redox catalyst. In transient pulse experiments, pulses of 37.5% $C_2H_6$ (100 μL, balance Ar) are injected into the U-tube reactor using 25 ml·min$^{-1}$ helium as carrier gas at 700° C. The regular space velocity is 3000 h$^{-1}$. Continuous flow experiments are used to obtain the oxygen capacity of a redox catalyst. Continuous flow experiment, a reduction step is conducted first, with a feedstock of 15 mL min$^{-1}$ ethane and 25 mL min$^{-1}$ Ar. An oxidation step is conducted in a following step using 10% oxygen (5 mL min$^{-1}$, balance Ar). Each reduction and oxidation step is performed for 5 min, with 5 min of Ar purging in between.

All products formed are monitored by a downstream quadruple mass spectrometer (QMS, MKS Cirrus II). They are quantified by integrating characteristic peaks of each species obtained from quadruple mass spectrometer. $C_2H_4$ formation is calculated by deducting the contribution of $C_2H_6$ to the mass 26 peak calculated by the characteristic ratio of mass 30 to mass 26 before calculating $C_2H_4$ concentration from mass 26. From QMS and GC observation, there are only three major components in the product stream: unreacted $C_2H_6$, $C_2H_4$ and $CO_2$. The molar ratio of ethylene and $CO_2$ product formation to redox catalyst active oxygen consumption are stoichiometrically estimated to be 1/1 and 1/3.5, respectively. The oxygen capacity of redox catalysts are calculated by using such an oxygen mass balance.

Figure 29:
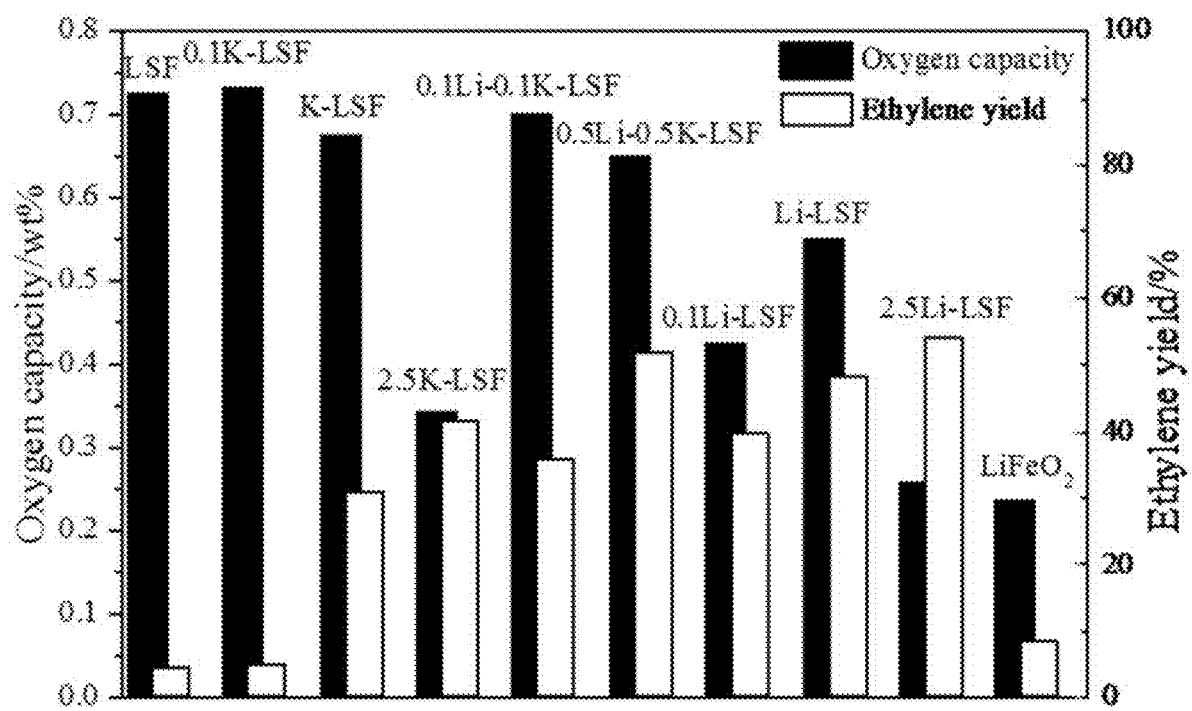
FIG. 29 is a graph of the oxygen capacity and ethylene yield of unpromoted LaSrFe, 0.1K—LaSrFe, K—LaSrFe, 2.5K—LaSrFe, 0.1Li—0.1K—LaSrFe and 0.5Li—0.5K—LaSrFe at 700° C.
Figure 30:
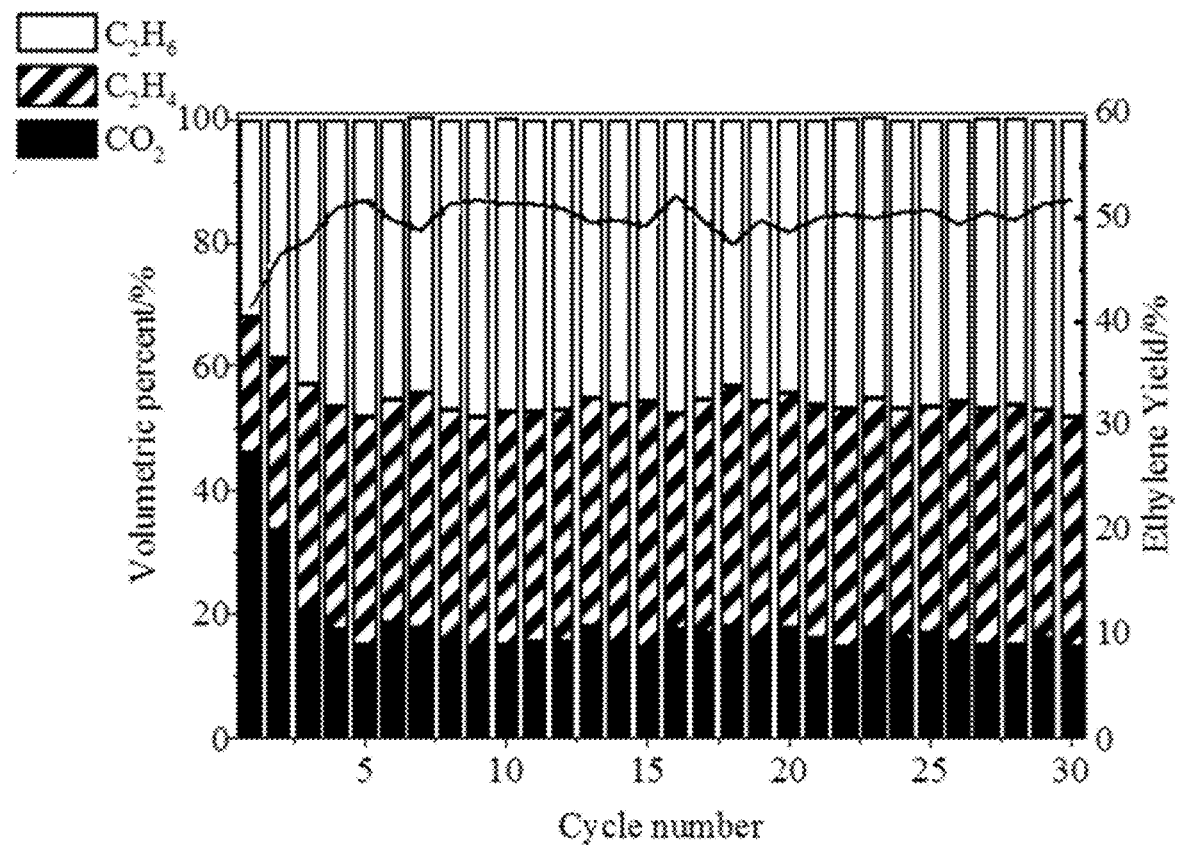
FIG. 30 is a graph of the product species distributions and ethylene yields obtained on 0.5K-0.5Li—LaSrFe for cycle number from 1 to 30 and temperature=700° C.

As is shown in FIG. 29, Li promoted LaSrFe can achieve good ODH conversion and selectivity. However, its oxygen capacity decreases quickly with Li promotion. On the other hand, K promoted LaSrFe can somewhat maintain the oxygen capacity, however, the conversion/selectivity/yield is not as satisfactory as Li promoted LaSrFe. Li and K co-promoted LaSrFe takes advantage of high oxygen capacity of K—LaSrFe and good ODH selectivity of Li—LaSrFe. The resulting catalyst (0.5K-0.5Li—LaSrFe) can achieve up to 86% ethylene selectivity and 60% ethane conversion while maintain an oxygen capacity over 0.6 wt %. The stability of this redox catalyst is also proved by running 30 redox cycles (FIG. 30). The conversion/selectivity/yields of Li and K co-promoted LaSrFe with various Li and K doping levels are tabulated in Table 6.

TABLE 6

Conversion/selectivity/yields for Li and K co-promoted LaSrFe

| | Ethane conversion | Ethylene selectivity | Ethylene yield |
|---|---|---|---|
| 0.1Li-0.1K-LaSrFe | 75% | 45% | 34% |
| 0.5Li-0.1K-LaSrFe | 52% | 64% | 33% |
| 0.5Li-0.5K-LaSrFe (space velocity = 1500 h$^{-1}$) | 60% | 86% | 52% |
| Li-0.5K-LaSrFe | 90% | 19% | 17% |

Figure 31A:
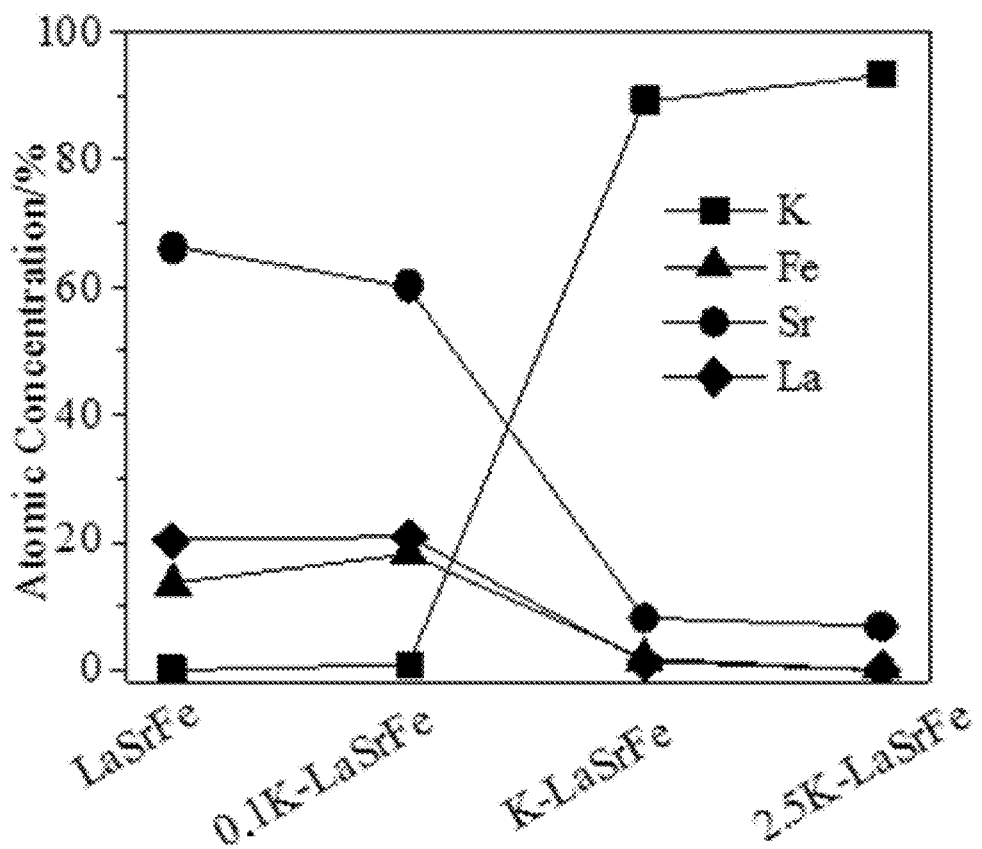
FIGS. 31A-31B are graphs of the near surface cation concentrations of as-prepared redox catalysts as determined by x-ray photoelectron spectroscopy (XPS) (FIG. 31A); and the ratios between near surface K concentration to bulk K concentration (FIG. 31B) for as-prepared redox catalysts (the dashed line in FIG. 31B is for ratio of 1).
Figure 31B:
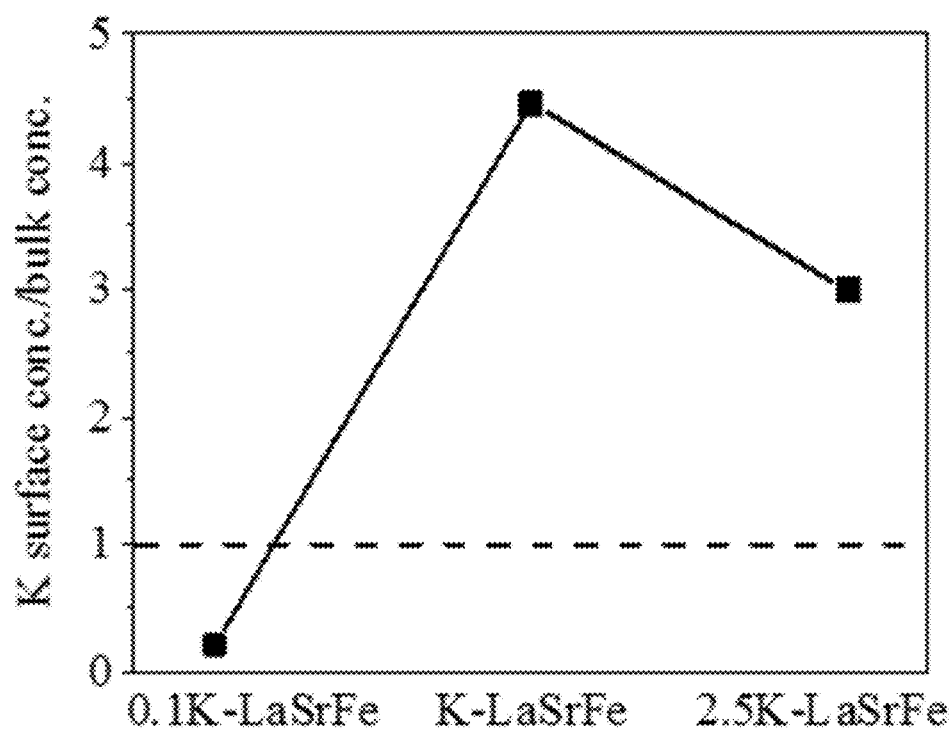
Figure 32A:
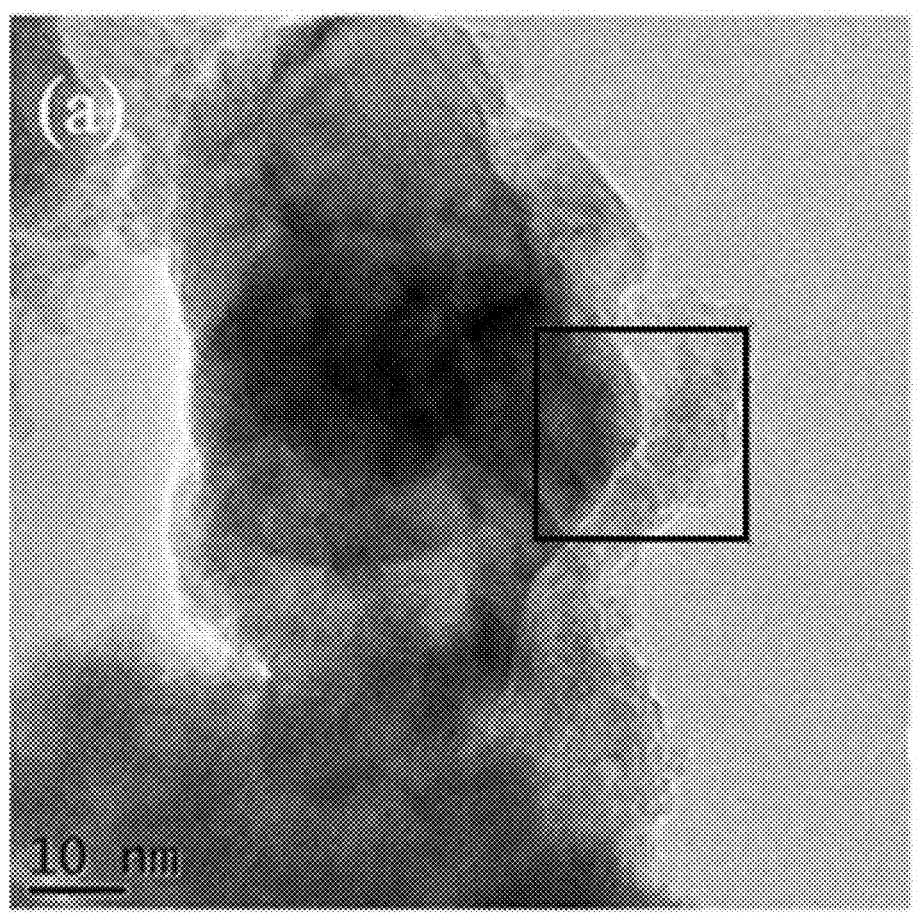
FIGS. 32A-32B are transmission electron micrographs of 0.5K—LaSrFe.
Figure 32B:
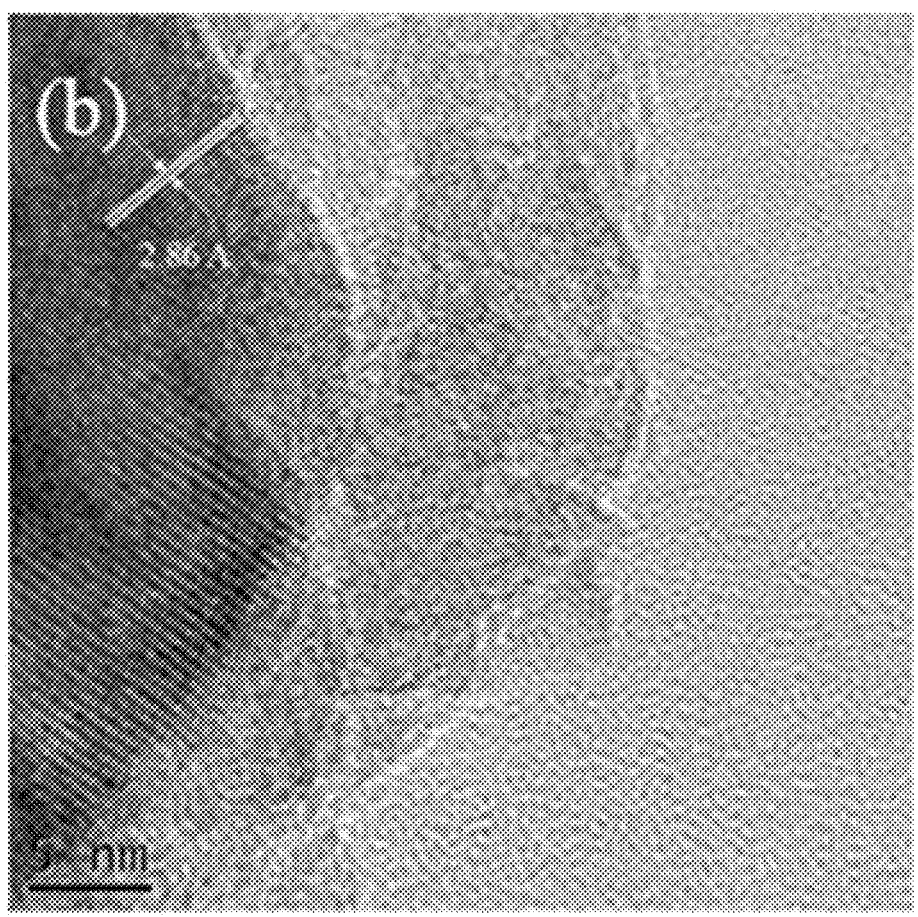

As Li is difficult to detect under XPS, K promoted LaSrFe is characterized instead as a model compound. XPS characterization shows that K cation is selectively enriched on the surface of the redox catalysts (FIGS. 31A-31B), forming a core-shell structure. It is determined from TEM that the core material is LaSrFe and the shell material is probably amorphous K-containing phase such as $K_2O$ (FIGS. 32A-32B).

Main Findings:
a. Sodium tungstate doping has little effect on oxygen capacity;
b. Sodium tungstate doping suppresses ethane combustion;
c. Sodium tungstate doping has little effect on hydrogen combustion;
d. Strontium ferrite is a promising SHC catalyst.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

REFERENCES (1) Gartner, C. A.; van Veen, A. C.; Lercher, J. A. *Chem Cat Chem* 2013, 5, 3196-3217.
(2) Bhasin, M. M.; McCain, J. H.; Vora, B. V.; Imai, T.; Pujado, P. R. *Appl. Catal. Gen.* 2001, 221, 397-419.
(3) Le Bars, J.; Auroux, A.; Forissier, M.; Vedrine, J. C. *J. Catal.* 1996, 162, 250-259.
(4) Mamedov, E. A.; Corberan, V. C. *Appl. Catal. Gen.* 1995, 127, 1-40.
(5) Christodoulakis, A.; Heracleous, E.; Lemonidou, A. A.; Boghosian, S. *J. Catal.* 2006, 242, 16-25.
(6) Chen, K.; Xie, S.; Bell, A. T.; Iglesia, E. *J. Catal.* 2001, 198, 232-242.
(7) Wu, Z.; Schwartz, V.; Li, M.; Rondinone, A. J.; Overbury, S. H. *J. Phys. Chem. Lett.* 2012, 3, 1517-1522.
(8) Au, C. T.; Zhou, X. P.; Wan, H. L. *Catal. Lett.* 1996, 40, 101-104.
(9) Huff, M.; Schmidt, L. D. *J. Phys. Chem.* 1993, 97, 11815-11822.
(10) Yokoyama, C.; Bharadwaj, S. S.; Schmidt, L. D. *Catal. Lett.* 1996, 38, 181-188.
(11) Skoufa, Z.; Heracleous, E.; Lemonidou, A. A. *Catal. Today* 2012, 192, 169-176.

(12) Heracleous, E.; Lemonidou, A. A. *J. Catal.* 2006, 237, 175-189.
(13) Contractor, R. M.; Bergna, H. E.; Horowitz, H. S.; Blackstone, C. M.; Malone, B.; Torardi, C. C.; Griffiths, B.; Chowdhry, U.; Sleight, A. W. *Catal. Today* 1987, 1, 49-58.
(14) Ballarini, N.; Cavani, F.; Cericola, A.; Cortelli, C.; Ferrari, M.; Trifiro, F.; Capannelli, G.; Comite, A.; Catani, R.; Cornaro, U. *Catal. Today* 2004, 91, 99-104.
(15) Li, F.; Fan, L.-S. *Energy Environ. Sci.* 2008, 1, 248-267.
(16) Fan, L.-S. *Chemical looping systems for fossil energy conversions.* Columbus, Ohio: John Wiley & Sons, 2011.
(17) Contractor, R. M. *Chem. Eng. Sci.* 1999, 54, 5627-5632.
(18) Al-Ghamdi, S. A.; Hossain, M. M.; de Lasa, H. I. *Ind. Eng. Chem. Res.* 2013, 52, 5235-5244.
(19) Al-Ghamdi, S.; Volpe, M.; Hossain, M. M.; de Lasa, H. *Appl. Catal. Gen.* 2013, 450, 120-130.
(20) Bakare, I. A.; Mohamed, S. A.; Al-Ghamdi, S.; Razzak, S. A.; Hossain, M. M.; de Lasa, H. I. *Chem. Eng. J.* 2015, 278, 207-216.
(21) Elbadawi, A. H.; Ba-Shammakh, M. S.; Al-Ghamdi, S.; Razzak, S. A.; Hossain, M. M. *Chem. Eng. J.* 2016, 284, 448-457.
(22) Li, F.; Kim, H. R.; Sridhar, D.; Wang, F.; Zeng, L.; Chen, J.; Fan, L.-S. *Energy Fuels* 2009, 23, 4182-4189.
(23) Cho, P.; Mattisson, T.; Lyngfelt, A. *Fuel* 2004, 83, 1215-1225.
(24) Johansson, M.; Mattisson, T.; Lyngfelt, A. *Chem. Eng. Res. Des.* 2006, 84, 807-818.
(25) Shafiefarhood, A.; Galinsky, N.; Huang, Y.; Chen, Y.; Li, F. *Chem Cat Chem* 2014, 6, 790-799.
(26) Neal, L. M.; Shafiefarhood, A.; Li, F. *ACS Catal.* 2014, 4, 3560-3569.
(27) Mudu, F.; Arstad, B.; Bakken, E.; Fjellvag, H.; Olsbye, U. *J. Catal.* 2010, 275, 25-33.
(28) Slagtern, Ase; Olsbye, U. *Appl. Catal. Gen.* 1994, 110, 99-108.
(29) Dai, H. X.; Ng, C. F.; Au, C. T. *J. Catal.* 2000, 189, 52-62.
(30) Conway, S. J.; Lunsford, J. H. *J. Catal.* 1991, 131, 513-522.
(31) Ito, T.; Wang, J.; Lin, C. H.; Lunsford, J. H. *J. Am. Chem. Soc.* 1985, 107, 5062-5068.
(32) Gartner, C. A.; Van Veen, A. C.; Lercher, J. A. *J. Am. Chem. Soc.* 2014, 136, 12691-12701.
(33) Kumar, C. P.; Gaab, S.; Miller, T. E.; Lercher, J. A. *Top. Catal.* 2008, 50, 156-167.
(34) Teraoka, Y.; Zhang, H.-M.; Yamazoe, N. *Chem. Lett.* 1985, 14, 1367-1370.
(35) Neal, L. M.; Yusuf, S.; Sofranko, J. A.; Li, F. *Energy Technol.* 2016.
(36) Shafiefarhood, A.; Hamill, J. C.; Neal, L. M.; Li, F. *Phys. Chem. Chem. Phys.* 2015, 17, 31297-31307.
(37) Hu, Y. H.; Ruckenstein, E. *J. Phys. Chem. B* 1998, 102, 230-233.
(38) Hu, Y. H.; Ruckenstein, E. *J. Phys. Chem. B* 1997, 101, 7563-7565.
(39) Ozkan, U.; Gill, R. C.; Smith, M. R. *J. Catal.* 1989, 116, 171-183.
(40) Galinsky, N.; Mishra, A.; Zhang, J.; Li, F. *Appl. Energy* 2015.
(41) Fujihara, S.; Nakata, T.; Kozuka, H.; Yoko, T. *J. Solid State Chem.* 1995, 115, 456-463.
(42) Neal, L.; Shafiefarhood, A.; Li, F. *Appl. Energy* 2015, 157, 391-398.
(43) Galinsky, N. L.; Huang, Y.; Shafiefarhood, A.; Li, F. *ACS Sustain. Chem. Eng.* 2013, 1, 364-373.
(44) Wachs, I. E.; Routray, K. *ACS Catal.* 2012, 2, 1235-1246.
(45) Tanaka, S.; Taniguchi, M.; Tanigawa, H. *J. Nucl. Mater.* 2000, 283, 1405-1408.
(46) Kim, Y.; Schlegl, H.; Kim, K.; Irvine, J. T. S.; Kim, J. H. *Appl. Surf. Sci.* 2014, 288, 695-701.
(47) Merino, N. A.; Barbero, B. P.; Eloy, P.; Cadus, L. E. *Appl. Surf. Sci.* 2006, 253, 1489-1493.
(48) Blasco, T.; Nieto, J. L. *Appl. Catal. Gen.* 1997, 157, 117-142.

We claim:

1. A core-shell redox catalyst for cyclic redox based oxidative dehydrogenation or oxidative cracking of a paraffin comprising an oxygen carrier core of a perovskite having an outer shell,
wherein
(a) the perovskite comprises $La_{0.6}Sr_{1.4}FeO_4$ and the outer shell comprises $LiFeO_2$;
(b) the perovskite comprises $Sr_3Fe_2O_7$ and the outer shell comprises sodium tungstate;
(c) the perovskite comprises $Sr_3Fe_2O_7$ and the outer shell comprises $LiFeO_2$; or
(d) the perovskite comprises $La_{0.6}Sr_{1.4}FeO_4$ and the outer shell comprises sodium tungstate;
wherein the outer shell and the oxygen carrier are present at a molar ratio of about 0.5 to 2.5.

2. The redox catalyst of claim 1, wherein the redox catalyst is a nanoparticle having a diameter of about 50 nm to 500 nm.

3. The redox catalyst of claim 1, wherein the outer shell has an average thickness of about 10 nm or less.

4. The redox catalyst of claim 1, wherein the perovskite is $La_{0.6}Sr_{1.4}FeO_4$ and the outer shell is $LiFeO_2$.

5. A method for oxidative cracking of paraffins, the method comprising:
contacting the paraffins having from 2 to 7 carbon atoms with the redox catalyst according to claim 1 under temperature of 600-800° C. to convert the paraffins to water and olefins, diolefins, or a combination thereof.

* * * * *